United States Patent
Ahmad et al.

(10) Patent No.: US 12,421,230 B2
(45) Date of Patent: Sep. 23, 2025

(54) TRICYCLIC HETEROARYL COMPOUNDS USEFUL AS IRAK4 INHIBITORS

(71) Applicant: BRISTOL-MYERS SQUIBB COMPANY, Princeton, NJ (US)

(72) Inventors: Saleem Ahmad, Wall, NJ (US); Lidet A. Negash, Plainsboro, NJ (US)

(73) Assignee: Bristol-Myers Squibb Company, Princeton, NJ (US)

(*) Notice: Subject to any disclaimer, the term of this patent is extended or adjusted under 35 U.S.C. 154(b) by 604 days.

(21) Appl. No.: 17/792,837

(22) PCT Filed: Feb. 2, 2021

(86) PCT No.: PCT/US2021/016126
§ 371 (c)(1),
(2) Date: Jul. 14, 2022

(87) PCT Pub. No.: WO2021/158498
PCT Pub. Date: Aug. 12, 2021

(65) Prior Publication Data
US 2023/0114683 A1   Apr. 13, 2023

Related U.S. Application Data

(60) Provisional application No. 62/969,406, filed on Feb. 3, 2020.

(51) Int. Cl.
C07D 471/04 (2006.01)
C07D 471/14 (2006.01)

(52) U.S. Cl.
CPC ......... *C07D 471/04* (2013.01); *C07D 471/14* (2013.01)

(58) Field of Classification Search
CPC .......................... C07D 471/04; C07D 471/14
See application file for complete search history.

(56) References Cited

U.S. PATENT DOCUMENTS

| | | | |
|---|---|---|---|
| 4,952,584 A | 8/1990 | Thompson et al. | |
| 8,084,620 B2 | 12/2011 | Liu et al. | |
| 8,575,153 B2 | 11/2013 | Kitamura et al. | |
| 8,586,751 B2 | 11/2013 | De Lucca et al. | |
| 9,663,467 B2 | 5/2017 | Moslin et al. | |
| 9,714,234 B2 | 7/2017 | Ko et al. | |
| 2005/0272753 A1 | 12/2005 | Nagashima et al. | |
| 2006/0148800 A1 | 7/2006 | Stadtmueller et al. | |
| 2009/0082329 A1 | 3/2009 | Halley et al. | |
| 2011/0230467 A1 | 9/2011 | Shirakami et al. | |
| 2014/0073637 A1 | 3/2014 | N'Guyen et al. | |

FOREIGN PATENT DOCUMENTS

| | | |
|---|---|---|
| EP | 2532656 A1 | 12/2012 |
| GB | 2388596 A1 | 11/2003 |
| WO | 02102800 A1 | 12/2002 |
| WO | 03/013523 A1 | 3/2003 |
| WO | 2004065378 A1 | 8/2004 |
| WO | 2005007646 A1 | 1/2005 |
| WO | 2005075468 A2 | 8/2005 |
| WO | 2008148889 A1 | 12/2008 |
| WO | 2009046416 A1 | 4/2009 |
| WO | 2011053701 A1 | 5/2011 |
| WO | 2012149567 A1 | 11/2012 |
| WO | 2013106612 A1 | 7/2013 |
| WO | 2013106614 A1 | 7/2013 |
| WO | 2013106641 A1 | 7/2013 |
| WO | 2014074657 A1 | 5/2014 |
| WO | 2014074660 A1 | 5/2014 |
| WO | 2014074675 A1 | 5/2014 |
| WO | 2015088564 A1 | 6/2015 |
| WO | 2015103453 A1 | 7/2015 |

(Continued)

OTHER PUBLICATIONS

Das, U.N. (Journal of Inflammation Research, 2010:3, pp. 143-170).*
Hartung, H., et al., "What do we know about the mechanism of action of disease-modifying treatments in MS?" J. Neurol., vol. 251(suppl. 5), pp. V/12-V/29 (2004).*
Wang et al., J. Immunol. 2007, 179, pp. 5958-5965, See Introduction.*
Buckley et al., "IRAK-4 inhibitors. Part 1: A series of amides:", Bioorganic & Medicinal Chemistry Letters, vol. 18 pp. 3211-3214 (2008).

(Continued)

*Primary Examiner* — Alicia L Otton
(74) *Attorney, Agent, or Firm* — Gary Greenblatt

(57) ABSTRACT

Disclosed are compounds of Formulas (I) or (II) or a salt thereof, wherein X, $R_1$, $R_2$, $R_3$, and n are defined herein. Also disclosed are methods of using such compounds as modulators of IRAK4, and pharmaceutical compositions comprising such compounds. These compounds are useful in treating, preventing, or slowing inflammatory and autoimmune diseases, or in the treatment of cancer.

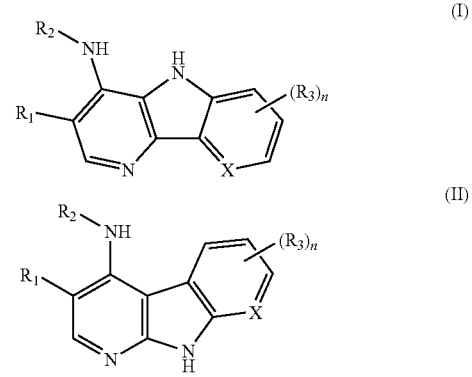

9 Claims, No Drawings
Specification includes a Sequence Listing.

(56) References Cited

FOREIGN PATENT DOCUMENTS

WO 2016210037 A1 12/2016
WO 18060174 A1 4/2018
WO 2018178041 A1 10/2018

OTHER PUBLICATIONS

Buckley et al., "IRAK-4 inhibitors. Part II: A structure-based assessment of imidazo[1,2-a]pyridine binding", Bioorganic Medicinal Chem Letters, vol. 18(11) pp. 3291-3295 (2008).
Buckley, et al., "IRAK-4 inhibitors. Part III: A series of imidazo[1,2-a]pyridines", Bioorganic Medicinal Chem Letters, vol. 18(11) pp. 36-56 (2008).
Gorlitzer, et al, "Pyrido[3,2-b]indol-4-yl-amine—Synthese und Prufung auf Wirksamkeit gegen Malaria 4, 5", Pharmazie, 2004, 59, 243-250.
Hynes et al., Annual Reports in Medicinal Chemistry, vol. 49, pp. 117-133.
International Preliminary Report on Patentability for PCT/US2021/016126, issued Jul. 28, 2022.
Seganish, W. Michael, "Inhibitors of interleukin-1 receptor-associated kinase 4 (IRAK4): a patent review (2012-2015)", Expert Opinion on Therapeutic Patents, vol. 26, No. 8, pp. 917-932 (2016).

\* cited by examiner

SEQUENCE LISTING

<160> NUMBER OF SEQ ID NOS: 1

<210> SEQ ID NO 1
<211> LENGTH: 16
<212> TYPE: PRT
<213> ORGANISM: Homo sapiens
<220> FEATURE:
<221> NAME/KEY: misc_feature
<223> OTHER INFORMATION: Flourescent tag attached to amino acid 1

<400> SEQUENCE: 1

Ile Pro Thr Ser Pro Ile Thr Thr Thr Tyr Phe Phe Phe Lys Lys Lys
1               5                   10                  15

TRICYCLIC HETEROARYL COMPOUNDS USEFUL AS IRAK4 INHIBITORS

CROSS REFERENCE

This application is a 371 application of International Patent Application No. PCT/US2021/016126, filed Feb. 2, 2021, which claims the benefit of U.S. Provisional Application Ser. No. 62/969,406, filed Feb. 3, 2020, the content of each is hereby fully incorporated herein in its entirety.

DESCRIPTION

The present invention generally relates to tricyclic heteroaryl compounds useful as kinase inhibitors, including the modulation of IRAK-4. Provided herein are tricyclic heteroaryl compounds, compositions comprising such compounds, and methods of their use. The invention further pertains to pharmaceutical compositions containing at least one compound according to the invention that are useful for the treatment of conditions related to kinase modulation and methods of inhibiting the activity of kinases, including IRAK-4 in a mammal.

Toll/IL-1 receptor family members are important regulators of inflammation and host resistance. The Toll like receptor (TLR) family recognizes molecular patterns derived from infectious organisms including bacteria, fungi, parasites, and viruses (reviewed in Kawai, T. et al., *Nature Immunol.*, 11:373-384 (2010)). Ligand binding to the receptor induces dimerization and recruitment of adaptor molecules to a conserved cytoplasmic motif in the receptor termed the Toll/IL-1 receptor (TIR) domain. With the exception of TLR3, all TLRs recruit the adaptor molecule MyD88. The IL-1 receptor family also contains a cytoplasmic TIR motif and recruits MyD88 upon ligand binding (reviewed in Sims, J. E. et al., *Nature Rev. Immunol.*, 10:89-102 (2010)).

Members of the IRAK family of serine/threonine kinases are recruited to the receptor via interactions with MyD88. The family consists of four members. Several lines of evidence indicate that IRAK4 plays a critical and non-redundant role in initiating signaling via MyD88 dependent TLRs and IL-1R family members. Structural data confirms that IRAK4 directly interacts with MyD88 and subsequently recruits either IRAK1 or IRAK2 to the receptor complex to facilitate downstream signaling (Lin, S. et al., *Nature*, 465: 885-890 (2010)). IRAK4 directly phosphorylates IRAK1 to facilitate downstream signaling to the E3 ubiquitin ligase TRAF6, resulting in activation of the serine/threonine kinase TAK1 with subsequent activation of the NFκB pathway and MAPK cascade (Flannery, S. et al., *Biochem. Pharmacol.*, 80:1981-1991 (2010)). A subset of human patients was identified who lack IRAK4 expression (Picard, C. et al., *Science*, 299:2076-2079 (2003)). Cells from these patients fail to respond to all TLR agonists with the exception of TLR3 as well as to members of the IL-1 family including IL-10 and IL-18 (Ku, C. et al., *J. Exp. Med.*, 204:2407-2422 (2007)). Deletion of IRAK4 in mice results in a severe block in IL-1, IL-18 and all TLR dependent responses with the exception of TLR3 (Suzuki, N. et al., *Nature*, 416:750-754 (2002)). In contrast, deletion of either IRAK1 (Thomas, J. A. et al., *J. Immunol.*, 163:978-984 (1999); Swantek, J. L. et al., *J. Immunol.*, 164:4301-4306 (2000) or IRAK2 (Wan, Y. et al., *J. Biol. Chem.*, 284:10367-10375 (2009)) results in partial loss of signaling. Furthermore, IRAK4 is the only member of the IRAK family whose kinase activity has been shown to be required for initiation of signaling. Replacement of wild type IRAK4 in the mouse genome with a kinase inactive mutant (KDKI) impairs signaling via all MyD88 dependent receptors including IL-1, IL-18 and all TLRs with the exception of TLR3 (Koziczak-Holbro, M. et al., *J. Biol. Chem.*, 282:13552-13560 (2007); Kawagoe, T. et al., *J. Exp. Med.*, 204:1013-1024 (2007); and Fraczek, J. et al., *J. Biol. Chem.*, 283:31697-31705 (2008)).

As compared to wild type animals, IRAK4 KDKI mice show greatly reduced disease severity in mouse models of multiple sclerosis (Staschke, K. A. et al., *J. Immunol.*, 183:568-577 (2009)), rheumatoid arthritis (Koziczak-Holbro, M. et al., *Arthritis Rheum.*, 60:1661-1671 (2009)), atherosclerosis (Kim, T. W. et al., *J. Immunol.*, 186:2871-2880 (2011) and Rekhter, M. et al., *Biochem. Biophys. Res. Comm.*, 367:642-648 (2008)), and myocardial infarction (Maekawa, Y. et al., *Circulation*, 120:1401-1414 (2009)). As described, IRAK4 inhibitors will block all MyD88 dependent signaling. MyD88 dependent TLRs have been shown to contribute to the pathogenesis of multiple sclerosis, rheumatoid arthritis, cardiovascular disease, metabolic syndrome, sepsis, systemic lupus erythematosus, inflammatory bowel diseases including Crohn's disease and ulcerative colitis, autoimmune uveitis, asthma, allergy, type I diabetes, and allograft rejection (Keogh, B. et al., *Trends Pharmacol. Sci.*, 32:435-442 (2011); Mann, D. L., *Circ. Res.*, 108:1133-1145 (2011); Horton, C. G. et al., *Mediators Inflamm.*, Article ID 498980 (2010), doi:10.1155/2010/498980; Goldstein, D. R. et al., *J. Heart Lung Transplant.*, 24:1721-1729 (2005); and Cario, E., *Inflamm. Bowel Dis.*, 16:1583-1597 (2010)). Oncogenically active MyD88 mutations in diffuse large B cell lymphomas have been identified that are sensitive to IRAK4 inhibition (Ngo, V. N. et al., *Nature*, 470:115-121 (2011)). Whole genome sequencing also identified mutations in MyD88 associated with chronic lymphatic leukemia suggesting that IRAK4 inhibitors may also have utility in treating leukemias (Puente, X. S. et al., *Nature*, 475:101-105 (2011)).

In addition to blocking TLR signaling, IRAK4 inhibitors will also block signaling by members of the IL-1 family. Neutralization of IL-1 has been shown to be efficacious in multiple diseases including gout; gouty arthritis; type 2 diabetes; auto-inflammatory diseases including Cryopyrin-Associated Periodic Syndromes (CAPS), TNF Receptor Associated Periodic Syndrome (TRAPS), Familial Mediterranean Fever (FMF), adult onset stills; systemic onset juvenile idiopathic arthritis; stroke; Graft-versus-Host Disease (GVHD); smoldering multiple myeloma; recurrent pericarditis; osteoarthritis; emphysema (Dinarello, C. A., *Eur. J. Immunol.*, 41:1203-1217 (2011) and Couillin, I. et al., *J. Immunol.*, 183:8195-8202 (2009)). In a mouse model of Alzheimer's disease, blockade of IL-1 receptor improved cognitive defects, attenuated tau pathology and reduced oligomeric forms of amyloid-β (Kitazawa, M. et al., *J. Immunol.*, 187:6539-6549 (2011)). IL-1 has also been shown to be a critical link to adaptive immunity, driving differentiation of the TH17 effector T cell subset (Chung, Y. et al., *Immunity*, 30:576-587 (2009)). Therefore, IRAK4 inhibitors are predicted to have efficacy in TH17 associated diseases including multiple sclerosis, psoriasis, inflammatory bowel diseases, autoimmune uveitis, and rheumatoid arthritis (Wilke, C. M. et al., *Trends Immunol.*, 32:603-661 (2011)).

In view of the conditions that may benefit by treatment involving modulation of protein kinases, it is immediately apparent that new compounds capable of modulating protein kinases such as IRAK-4 and methods of using these compounds could provide substantial therapeutic benefits to a wide variety of patients.

SUMMARY OF THE INVENTION

The present invention relates to a new class of tricyclic heteroaryl compounds found to be effective inhibitors of protein kinases including IRAK-4. These compounds are provided to be useful as pharmaceuticals with desirable stability, bioavailability, therapeutic index, and toxicity values that are important to their drugability.

The present invention provides compounds of Formula (I) and Formula (II) that are useful as inhibitors of IRAK-4, and are useful for the treatment of proliferative diseases, allergic diseases, autoimmune diseases and inflammatory diseases, or stereoisomers, tautomers, pharmaceutically acceptable salts, solvates or prodrugs thereof.

The present invention also provides pharmaceutical compositions comprising a pharmaceutically acceptable carrier and at least one of the compounds of the present invention or stereoisomers, tautomers, pharmaceutically acceptable salts, solvates, or prodrugs thereof.

The present invention also provides a method for inhibition of IRAK-4 comprising administering to a host in need of such treatment a therapeutically effective amount of at least one of the compounds of the present invention or stereoisomers, tautomers, pharmaceutically acceptable salts, solvates, or prodrugs thereof.

The present invention also provides a method for treating proliferative, metabolic, allergic, autoimmune and inflammatory diseases, comprising administering to a host in need of such treatment a therapeutically effective amount of at least one of the compounds of the present invention or stereoisomers, tautomers, pharmaceutically acceptable salts, solvates, or prodrugs thereof.

One embodiment provides a method for treating inflammatory and autoimmune diseases. Particular, inflammatory and autoimmune diseases include, but are not limited to, Crohn's disease, ulcerative colitis, asthma, graft versus host disease, allograft rejection, chronic obstructive pulmonary disease, Graves' disease, rheumatoid arthritis, systemic lupus erythematosus, lupus nephritis, cutaneous lupus, psoriasis, cryopyrin-associated periodic syndromes (CAPS), TNF receptor associated periodic syndrome (TRAPS), familial Mediterranean fever (FMF), adult onset stills, systemic onset juvenile idiopathic arthritis, multiple sclerosis, neuropathic pain, gout, and gouty arthritis.

One embodiment provides a method for treating gout and gouty arthritis.

An alternate embodiment is a method for treating metabolic diseases, including type 2 diabetes and atherosclerosis.

One embodiment provides a method for treating cancer comprising administering to a host in need of such treatment a therapeutically effective amount of at least one of the compounds of the present invention or stereoisomers, tautomers, pharmaceutically acceptable salts, solvates, or prodrugs thereof.

The present invention also provides the compounds of the present invention or stereoisomers, tautomers, pharmaceutically acceptable salts, solvates, or prodrugs thereof, for use in therapy.

The present invention also provides the use of the compounds of the present invention or stereoisomers, tautomers, pharmaceutically acceptable salts, solvates, or prodrugs thereof, for the manufacture of a medicament for the treatment of cancer.

The present invention also provides a compound of Formula (I) or Formula (II), or a pharmaceutical composition in a kit with instructions for using the compound or composition.

The present invention also provides processes and intermediates for making the compounds of the present invention or stereoisomers, tautomers, pharmaceutically acceptable salts, solvates, or prodrugs thereof.

These and other features of the invention will be set forth in the expanded form as the disclosure continues.

DETAILED DESCRIPTION

The first aspect of the present invention provides at least one compound of Formula (I) or Formula (II):

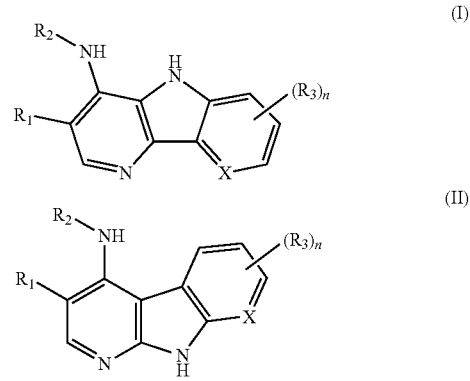

or a salt thereof, wherein:

X is $CR_{3a}$ or N;

$R_1$ is:
(i) —C(O)$NR_xR_{1a}$; or
(ii) pyrazolyl, imidazolyl, isoxazolyl, oxazolyl, oxadiazolyl, triazolyl, or thiadiazolyl, each substituted with zero to 2 $R_{1b}$;

$R_{1a}$ is:
(i) $C_{1-6}$ alkyl substituted with zero to 6 $R_w$; or
(ii) —$(CR_xR_x)_{0-3}R_{1c}$;

each $R_w$ is independently F, Cl, —CN, —OH, —OCH$_3$, —$NR_xR_x$, —$NR_xC(O)(C_{1-3}$ alkyl), —$NR_xC(O)(C_{3-6}$ cycloalkyl), or $C_{3-6}$ cycloalkyl;

each $R_{1b}$ is independently —$CR_xR_x(C_{3-6}$ cycloalkyl), tetrahydrofuranyl, pyrrolidinyl, tetrahydropyranyl, piperidinyl, piperazinyl, morpholinyl, or $C_{1-6}$ alkyl substituted with zero to 6 $R_w$;

$R_{1c}$ is $C_{3-6}$ cycloalkyl, oxetanyl, pyrrolidinyl, piperidinyl, piperazinyl, morpholinyl, tetrahydropyranyl, dioxidotetrahydrothiophenyl, dioxidothiomorpholinyl, isoxazolyl, oxazolyl, thiazolyl, oxadiazolyl, triazolyl, or tetrazolyl, each substituted with zero to 3 substituents independently selected from F, Cl, —CN, —OH, —$NR_xR_x$, $C_{1-3}$ alkyl, $C_{1-3}$ fluoroalkyl, $C_{1-3}$ hydroxyalkyl, —$NR_xC(O)(C_{1-3}$ alkyl), —$NR_xC(O)O(C_{1-3}$ alkyl), and —$S(O)_2(C_{1-2}$ alkyl);

$R_2$ is:
(i) hydrogen;
(ii) $C_{1-6}$ alkyl substituted with zero to 4 substituents independently selected from F, $C_1$, —OH, —CN, $C_{3-6}$ cycloalkyl, and dimethoxyphenyl; or
(ii) a cyclic group selected from $C_{3-6}$ cycloalkyl, oxetanyl, tetrahydrofuranyl, tetrahydropyranyl, piperidinyl, pyrazolyl, and thiazolyl, wherein said cyclic group is substituted with zero to 3 substituents independently selected from F, Cl, —OH, —CN, $C_{1-2}$ alkyl, $C_{1-2}$ fluoroalkyl, $C_{1-2}$ hydroxyalkyl, and —$S(O)_2(C_{1-2}$ alkyl);

R$_3$ is —CN, —C(O)NR$_x$R$_x$, or a cyclic group selected from phenyl, pyrazolyl, imidazolyl, triazolyl, pyridinyl, pyridinonyl, and pyrimidinyl, each cyclic group substituted with zero to 3 substituents selected from F, Cl, —OH, —CN, C$_{1-2}$ alkyl, —CF$_3$, and —CH$_2$OH;

R$_{1a}$ is hydrogen or R$_3$;

each R$_x$ is hydrogen or —CH$_3$; and n is zero, 1, or 2.

In one embodiment, a compound of Formula (I) or a salt thereof is provided.

In one embodiment, a compound of Formula (II) or a salt thereof is provided.

In one embodiment, a compound of Formula (I) or a salt thereof is provided wherein X is CR$_{3a}$. Compounds of this embodiment have the structure of Formula (Ia):

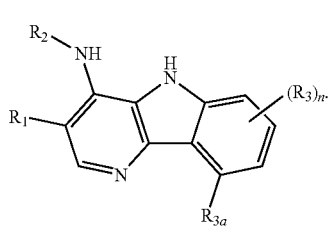

(Ia)

Included in this embodiment are compounds in which R$_{3a}$ is hydrogen. Also included in this embodiment are compounds in which R$_{3a}$ is R$_3$.

In one embodiment, a compound of Formula (I) or a salt thereof is provided wherein X is N. Compounds of this embodiment have the structure of Formula (Ib):

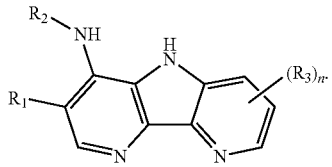

(Ib)

In one embodiment, a compound of Formula (II) or a salt thereof is provided wherein X is CR$_{3a}$. Compounds of this embodiment have the structure of Formula (IIa):

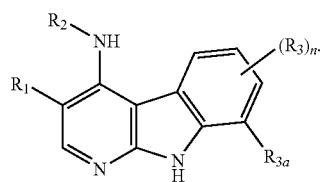

(IIa)

Included in this embodiment are compounds in which R$_{3a}$ is hydrogen. Also included in this embodiment are compounds in which R$_{3a}$ is R$_3$.

In one embodiment, a compound of Formula (II) or a salt thereof is provided wherein X is N. Compounds of this embodiment have the structure of Formula (IIb):

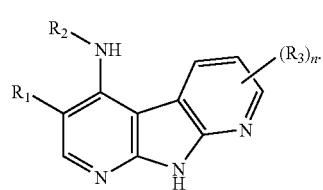

(IIb)

In one embodiment, a compound of Formula (I) or a salt thereof is provided having the structure of Formula (Ic):

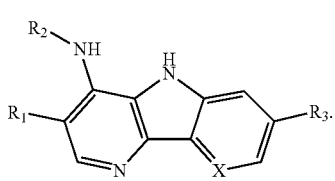

(Ic)

In one embodiment, a compound of Formula (Ic) or a salt thereof is provided wherein X is CR$_{3a}$. Compounds of this embodiment have the structure of Formula (Id):

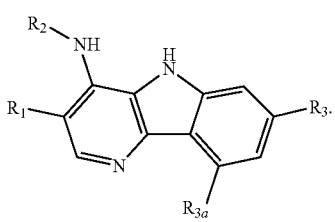

(Id)

In one embodiment, a compound of Formula (Ic) or a salt thereof is provided wherein X is CR$_{3a}$ and R$_{3a}$ is hydrogen. Compounds of this embodiment have the structure of Formula (Ie):

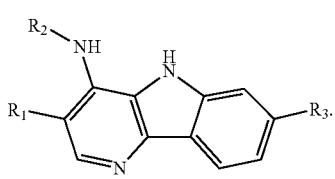

(Ie)

In one embodiment, a compound of Formula (Ic) or a salt thereof is provided wherein X is N. Compounds of this embodiment have the structure of Formula (If):

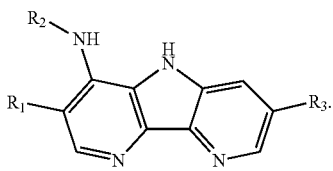
(If)

In one embodiment, a compound of Formula (II) or a salt thereof is provided having the structure of Formula (IIc):

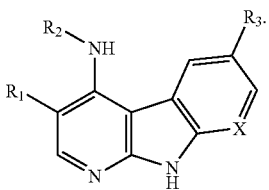
(IIc)

In one embodiment, a compound of Formula (IIc) or a salt thereof is provided wherein X is $CR_{3a}$. Compounds of this embodiment have the structure of Formula (IId):

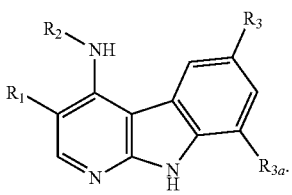
(IId)

In one embodiment, a compound of Formula (IIc) or a salt thereof is provided wherein X is $CR_{3a}$ and $R_{3a}$ is hydrogen. Compounds of this embodiment have the structure of Formula (IIe):

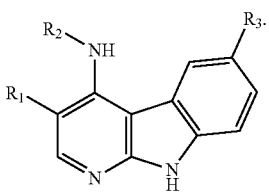
(IIe)

In one embodiment, a compound of Formula (IIc) or a salt thereof is provided wherein X is N. Compounds of this embodiment have the structure of Formula (IIf):

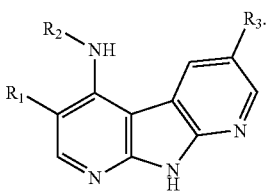
(IIf)

In one embodiment, a compound of Formula (I) or Formula (II), or salt thereof is provided wherein X is CH.

In one embodiment, a compound of Formula (I) or Formula (II) or salt thereof is provided wherein $R_1$ is —C(O)$NR_xR_{1a}$. Included in this embodiment are compounds in which $R_1$ is —C(O)$NHR_{1a}$.

In one embodiment, a compound of Formula (I) or Formula (II) or salt thereof is provided wherein $R_1$ is —C(O)$NR_xR_{1a}$; and $R_{1a}$ is $C_{1-6}$ alkyl substituted with zero to 6 $R_w$. Included in this embodiment are compounds in which $R_{1a}$ is —$CH_2CH_2CH_3$, —$CH_2CH(CH_3)_2$, —$CH_2CH_2CH(CH_3)_2$, —$CH_2CH_2CHF_2$, —$CH_2CH_2CF_3$, —$CH_2CH_2C(CH_3)_2F$, —$CH_2CH_2CH(CH_3)OH$, —$CH_2C(CH_3)_2CH_2OH$, —$CH_2CH_2C(CH_3)_2OH$, —$CH_2CHFCH(CH_3)OH$, —$CH_2CHFC(CH_3)_2OH$, —$CH_2CH_2OCH_3$, —$CH_2CH_2C(CH_3)_2NH_2$, —$CH_2CF_2CH_2NH_2$, or —$CH_2CH_2C(CH_3)_2NHC(O)CH_3$.

In one embodiment, a compound of Formula (I) or Formula (II), or salt thereof is provided wherein $R_1$ is —C(O)$NR_xR_{1a}$; and $R_{1a}$ is —$(CR_xR_x)_{0-3}R_{1c}$. Included in this embodiment are compounds in which $R_{1a}$ is —$(CH_2)_{0-3}R_{1c}$. Also included in this embodiment are compounds in which $R_{1a}$ is —CH(cyclopropyl)$CH_2CH_2OH$, —$CH_2CH_2C(CH_3)_2NHC(O)$(cyclopropyl), $R_{1c}$, —$CH_2R_{1c}$, or —$CH_2CH_2R_{1c}$. Additionally, included in this embodiment are compounds in which $R_{1c}$ is cyclopropyl, cyclobutyl, oxetanyl, pyrrolidinyl, piperidinyl, morpholinyl, tetrahydropyranyl, dioxidotetrahydrothiophenyl, dioxidothiomorpholinyl, isoxazolyl, oxazolyl, thiazolyl, triazolyl, or tetrazolyl, each substituted with zero to 3 substituents independently selected from F, —OH, —$NH_2$, —$CH_3$, —$CH_2OH$, —C($CH_3$)$_2OH$, —NHC(O)$CH_3$, —NHC(O)O$CH_3$, and —S(O)$_2CH_3$.

In one embodiment, a compound of Formula (I) or Formula (II) or salt thereof is provided wherein $R_1$ is pyrazolyl, imidazolyl, isoxazolyl, oxazolyl, oxadiazolyl, triazolyl, or thiadiazolyl, each substituted with zero to 2 $R_{1b}$. Included in this embodiment are compounds in which $R_1$ is isoxazolyl, oxazolyl, oxadiazolyl, or triazolyl, each substituted with zero to 1 $R_{1b}$. Also included in this embodiment are compounds in which $R_1$ is isoxazolyl, oxadiazolyl, or triazolyl, each substituted with $R_{1b}$.

In one embodiment, a compound of Formula (I) or Formula (II), or salt thereof is provided wherein $R_2$ is: (i) hydrogen; or (ii) $C_{1-6}$ alkyl substituted with zero to 4 substituents independently selected from F, Cl, —OH, —CN, $C_{3-6}$ cycloalkyl, and dimethoxyphenyl. Included in this embodiment are compounds in which $R_2$ is hydrogen, —$CH_2CH_3$—CH($CH_3$)$_2$, —CH($CH_3$)$CH_2CH_3$, —$CH_2CHF_2$, —$CH_2CF_3$, —CH($CH_3$)$CH_2OH$, —$CH_2$(cyclopropyl), —CH($CH_3$)(cyclopropyl), or —$CH_2$(dimethoxyphenyl). In one embodiment, a compound of Formula (I) or Formula (II), or salt thereof is provided wherein $R_2$ is a cyclic group selected from $C_{3-6}$ cycloalkyl, oxetanyl, tetrahydrofuranyl, tetrahydropyranyl, piperidinyl, pyrazolyl, and thiazolyl, wherein said cyclic group is substituted with zero to 3 substituents independently selected from F, Cl, —OH, —CN, $C_{1-2}$ alkyl, $C_{1-2}$ fluoroalkyl, $C_{1-2}$ hydroxyalkyl, and —S(O)$_2$($C_{1-2}$ alkyl). Included in this embodiment are compounds in which $R_2$ is cyclopropyl, cyclobutyl, difluorocyclobutyl, oxetanyl, tetrahydrofuranyl, (methylsulfonyl)piperidinyl, thiazolyl, or (difluoroethyl)pyrazolyl.

In one embodiment, a compound of Formula (I) or Formula (II), or salt thereof is provided wherein $R_3$ is —CN, —C(O)$NR_xR_x$, or a cyclic group selected from phenyl, pyrazolyl, imidazolyl, pyridinyl, pyridinonyl, and pyrimidinyl, each cyclic group substituted with zero to 3 substituents selected from F, Cl, —OH, —CN, $C_{1-2}$ alkyl, —$CF_3$, and —$CH_2OH$. Included in this embodiment are compounds in which $R_3$ is —CN, —C(O)$NH_2$, pyrazolyl, or pyridinonyl.

In one embodiment, a compound of Formula (I) or Formula (II), or salt thereof is provided wherein $R_3$ is —CN or —C(O)$NR_xR_x$. Included in this embodiment are compounds in which $R_3$ is —CN or —C(O)$NHR_x$. Also included in this embodiment are compounds in which $R_3$ is —CN or —C(O)$NH_2$. Additionally, included in this embodiment are compounds in which $R_3$ is —CN.

In one embodiment, a compound of Formula (I) or Formula (II), or salt thereof is provided wherein $R_3$ is a cyclic group selected from phenyl, pyrazolyl, imidazolyl, pyridinyl, pyridinonyl, and pyrimidinyl, each cyclic group substituted with zero to 3 substituents selected from F, Cl, —OH, —CN, $C_{1-2}$ alkyl, —$CF_3$, and —$CH_2OH$. Included in this embodiment are compounds in which a cyclic group selected from pyrazolyl, imidazolyl, pyridinyl, pyridinonyl, and pyrimidinyl, each cyclic group substituted with zero to 2 substituents selected from F, Cl, —OH, —CN, $C_{1-2}$ alkyl, —$CF_3$, and —$CH_2OH$. Also included in this embodiment are compounds in which $R_3$ is pyrazolyl or pyridinonyl.

In one embodiment, a compound of Formula (Ic) or Formula (IIe) is provided or a salt thereof, wherein: X is CH or N; $R_1$ is: (i) —C(O)$NR_xR_{1a}$; or (ii) isoxazolyl, oxadiazolyl, or triazolyl, each substituted with $R_{1b}$; $R_{1a}$ is —$CH_2CH_2CH_3$, —$CH_2CH(CH_3)_2$, —$CH_2CH_2CH(CH_3)_2$, —$CH_2CH_2CHF_2$, —$CH_2CH_2CF_3$, —$CH_2CH_2C(CH_3)_2F$, —$CH_2CH_2CH(CH_3)OH$, —$CH_2C(CH_3)_2CH_2OH$, —$CH_2CH_2C(CH_3)_2OH$, —$CH_2CHFCH(CH_3)OH$, —$CH_2CHFC(CH_3)_2OH$, —$CH_2CH_2OCH_3$, —$CH_2CH_2C(CH_3)_2NH_2$, —$CH_2CF_2CH_2NH_2$, —$CH_2CH_2C(CH_3)_2NHC(O)CH_3$, —CH(cyclopropyl)$CH_2CH_2OH$, —$CH_2CH_2C(CH_3)_2NHC(O)$(cyclopropyl), Rio, —$CH_2R_{1c}$, or —$CH_2CH_2R_{1c}$; $R_{1b}$ is —$CH_2CH_2CH_3$, —$CH_2CH(CH_3)_2$, —$CH_2CH_2CH(CH_3)_2$, —$CH_2$(cyclopropyl), tetrahydropyranyl, piperidinyl, or morpholinyl; $R_{1c}$ is cyclopropyl, cyclobutyl, oxetanyl, pyrrolidinyl, piperidinyl, morpholinyl, tetrahydropyranyl, dioxidotetrahydrothiophenyl, dioxidothiomorpholinyl, isoxazolyl, oxazolyl, thiazolyl, triazolyl, or tetrazolyl, each substituted with zero to 3 substituents independently selected from F, —OH, —$NH_2$, —$CH_3$, —$CH_2OH$, —C($CH_3)_2OH$, —NHC(O)$CH_3$, —NHC(O)$OCH_3$, and —S(O)$_2CH_3$; $R_2$ is hydrogen, —$CH_2CH_3$, —CH($CH_3)_2$, —CH($CH_3)CH_2CH_3$, —$CH_2CHF_2$, —$CH_2CF_3$, —CH($CH_3)CH_2OH$, —$CH_2$(cyclopropyl), —CH($CH_3$)(cyclopropyl), —$CH_2$(dimethoxyphenyl), cyclopropyl, cyclobutyl, difluorocyclobutyl, oxetanyl, tetrahydrofuranyl, (methyl sulfonyl)piperidinyl, thiazolyl, or (difluoroethyl)pyrazolyl; and $R_3$ is —CN, —C(O)$NH_2$, pyrazolyl, or pyridinonyl.

In one embodiment, a compound of Formula (I) or Formula (II), or salt thereof is provided wherein $R_2$ is —CH($CH_3)_2$; and $R_3$ is —CN.

In one embodiment, a compound of Formula (I) or Formula (II), or salt thereof is provided wherein X is CH; $R_2$ is —CH($CH_3)_2$; and $R_3$ is —CN.

In one embodiment, a compound of Formula (I) or salt thereof is provided wherein X is CH; $R_2$ is —CH($CH_3)_2$; and $R_3$ is —CN.

In one embodiment, a compound of Formula (II) or salt thereof is provided wherein X is CH; $R_2$ is —CH($CH_3)_2$; and $R_3$ is —CN.

In one embodiment, a compound of Formula (Ic) or salt thereof is provided wherein X is CH; $R_2$ is —CH($CH_3)_2$; and $R_3$ is —CN.

In one embodiment, a compound of Formula (IIc) or salt thereof is provided wherein X is CH; $R_2$ is —CH($CH_3)_2$; and $R_3$ is —CN.

In one embodiment, a compound of Formula (Ie) or salt thereof is provided wherein $R_2$ is —CH($CH_3)_2$; and $R_3$ is —CN.

In one embodiment, a compound of Formula (IIe) or salt thereof is provided wherein $R_2$ is —CH($CH_3)_2$; and $R_3$ is —CN.

In one embodiment, a compound of Formula (I) or Formula (II), or salt thereof is provided wherein $R_1$ is —C(O)$NHR_{1a}$; and $R_{1a}$ is —$CH_2CH_2CH_3$, —$CH_2CH(CH_3)_2$, —$CH_2CH_2CH(CH_3)_2$, —$CH_2CH_2CHF_2$, —$CH_2CH_2CF_3$, —$CH_2CH_2C(CH_3)_2F$, —$CH_2CH_2CH(CH_3)OH$, —$CH_2C(CH_3)_2CH_2OH$, —$CH_2CH_2C(CH_3)_2OH$, —$CH_2CHFCH(CH_3)OH$, —$CH_2CHFC(CH_3)_2OH$, or —$CH_2CH_2OCH_3$. Included in this embodiment are compounds in which $R_{1a}$ is —$CH_2CH_2C(CH_3)_2F$, —$CH_2CH_2CH(CH_3)OH$, —$CH_2C(CH_3)_2CH_2OH$, —$CH_2CH_2C(CH_3)_2OH$, —$CH_2CHFCH(CH_3)OH$, or —$CH_2CHFC(CH_3)_2OH$.

In one embodiment, a compound of Formula (I) or Formula (II), or salt thereof is provided wherein $R_1$ is —C(O)$NHR_{1a}$; $R_{1a}$ is —$CH_2CH_2CH_3$, —$CH_2CH(CH_3)_2$, —$CH_2CH_2CH(CH_3)_2$, —$CH_2CH_2CHF_2$, —$CH_2CH_2CF_3$, —$CH_2CH_2C(CH_3)_2F$, —$CH_2CH_2CH(CH_3)OH$, —$CH_2C(CH_3)_2CH_2OH$, —$CH_2CH_2C(CH_3)_2OH$, —$CH_2CHFCH(CH_3)OH$, —$CH_2CHFC(CH_3)_2OH$, or —$CH_2CH_2OCH_3$; $R_2$ is —CH($CH_3)_2$; and $R_3$ is —CN. Included in this embodiment are compounds in which X is CH.

In one embodiment, a compound of Formula (Ic) or Formula (IIc), or salt thereof is provided wherein $R_1$ is —C(O)$NHR_{1a}$; $R_{1a}$ is —$CH_2CH_2CH_3$, —$CH_2CH(CH_3)_2$, —$CH_2CH_2CH(CH_3)_2$, —$CH_2CH_2CHF_2$, —$CH_2CH_2CF_3$, —$CH_2CH_2C(CH_3)_2F$, —$CH_2CH_2CH(CH_3)OH$, —$CH_2C(CH_3)_2CH_2OH$, —$CH_2CH_2C(CH_3)_2OH$, —$CH_2CHFCH(CH_3)OH$, —$CH_2CHFC(CH_3)_2OH$, or —$CH_2CH_2OCH_3$; $R_2$ is —CH($CH_3)_2$; and $R_3$ is —CN. Included in this embodiment are compounds in which X is CH.

One embodiment provides a compound of Formula (I) or a salt thereof, wherein said compound is: (R)-7-cyano-N-(2-fluoro-3-hydroxy-3-methylbutyl)-4-(isopropylamino)-5H-pyrido[3,2-b]indole-3-carboxamide (1); (R)-7-cyano-4-(ethylamino)-N-(2-fluoro-3-hydroxy-3-methylbutyl)-5H-pyrido[3,2-b]indole-3-carboxamide (2); (R)-7-cyano-4-((3,3-difluorocyclobutyl)amino)-N-(2-fluoro-3-hydroxy-3-methylbutyl)-5H-pyrido[3,2-b]indole-3-carboxamide (3); (R)-7-cyano-4-(cyclobutylamino)-N-(2-fluoro-3-hydroxy-3-methylbutyl)-5H-pyrido[3,2-b]indole-3-carboxamide (4); 7-cyano-N-(3-hydroxy-3-methylbutyl)-4-(isopropylamino)-5H-pyrido[3,2-b]indole-3-carboxamide (5); 7-cyano-4-(isopropylamino)-N-(tetrahydro-2H-pyran-3-yl)-5H-pyrido[3,2-b]indole-3-carboxamide (6); 7-cyano-N-((3-(hydroxymethyl) oxetan-3-yl)methyl)-4-(isopropylamino)-5H-pyrido[3,2-b]indole-3-carboxamide (7); 7-cyano-N-((1-(hydroxymethyl)cyclopropyl)methyl)-4-(isopropylamino)-5H-pyrido[3,2-b]indole-3-carboxamide (8); 7-cyano-N-(3-hydroxy-2,2-dimethylpropyl)-4-(isopropylamino)-5H-pyrido[3,2-b]indole-3-carboxamide (9); 7-cyano-N-((1R,4R)-4-hydroxycyclohexyl)-4-(isopropylamino)-5H-pyrido[3,2-b]indole-3-carboxamide (10); 7-cyano-4-(isopropylamino)-N-(tetrahydro-2H-pyran-4-yl)-5H-pyrido[3,2-b]indole-3-carboxamide (11); N-((1R,4R)-4-aminocyclohexyl)-7-cyano-4-(isopropylamino)-5H-pyrido[3,2-b]indole-3-carboxamide (12); N-((1R,4R)-4-acetamidocyclohexyl)-7-cyano-4-(isopropylamino)-5H-pyrido[3,2-b]indole-3-carboxamide (13); 7-cyano-4-(isopropylamino)-N-(oxazol-4-ylmethyl)-5H-pyrido[3,2-b]

indole-3-carboxamide (14); 7-cyano-4-(isopropylamino)-N-((3-methylisoxazol-5-yl)methyl)-5H-pyrido[3,2-b]indole-3-carboxamide (15); 7-cyano-N-(1-cyclopropyl-3-hydroxypropyl)-4-(isopropylamino)-5H-pyrido[3,2-b]indole-3-carboxamide (16); 7-cyano-4-(isopropylamino)-N-(2-methoxyethyl)-5H-pyrido[3,2-b]indole-3-carboxamide (17); 7-cyano-4-(isopropylamino)-N-(thiazol-2-ylmethyl)-5H-pyrido[3,2-b]indole-3-carboxamide (18); 7-cyano (isopropylamino)-N-(piperidin-4-yl)-5H-pyrido[3,2-b]indole-3-carboxamide (19); N-((1H-1,2,4-triazol-5-yl)methyl)-7-cyano-4-(isopropylamino)-5H-pyrido[3,2-b] indole carboxamide (20); 7-cyano-N-isopentyl-4-(isopropylamino)-5H-pyrido[3,2-b] indole carboxamide (21); (R)-7-cyano-N-(2-fluoro-3-hydroxy-3-methylbutyl)-4-(oxetan ylamino)-5H-pyrido[3,2-b]indole-3-carboxamide (22); (R)-7-cyano-4-((1-(2,2-difluoroethyl)-1H-pyrazol-4-yl)amino)-N-(2-fluoro-3-hydroxy-3-methylbutyl)-5H-pyrido[3,2-b]indole-3-carboxamide (23); 7-cyano-N-((1s,3s)-3-hydroxycyclobutyl)-4-(isopropylamino)-5H-pyrido[3,2-b]indole-3-carboxamide (24); 7-cyano-N-(3-hydroxybutyl)-4-(isopropylamino)-5H-pyrido[3,2-b]indole-3-carboxamide (25); (R)-7-cyano-N-(3-hydroxy-3-methylbutyl)-4-((tetrahydrofuran-3-yl)amino)-5H-pyrido[3,2-b] indole-3-carboxamide (26); 7-cyano-4-(isopropylamino)-N-(3,3,3-trifluoropropyl)-5H-pyrido[3,2-b]indole-3-carboxamide (27); (S)-7-cyano-N-(3-hydroxy-3-methylbutyl)-4-((tetrahydrofuran-3-yl)amino)-5H-pyrido[3,2-b]indole-3-carboxamide (28); (S)-7-cyano-4-((1-cyclopropylethyl)amino)-N-(3-hydroxy-3-methylbutyl)-5H-pyrido[3,2-b]indole-3-carboxamide (29); (S)-7-cyano-N-(3-hydroxy-3-methylbutyl)-4-((1-hydroxypropan-2-yl) amino)-5H-pyrido[3,2-b]indole-3-carboxamide (30); 7-cyano-N-(3,3-difluoropropyl)-4-(isopropylamino)-5H-pyrido[3,2-b]indole-3-carboxamide (31); (R)-4-(sec-butylamino)-7-cyano-N-(3-hydroxy-3-methylbutyl)-5H-pyrido[3,2-b]indole-3-carboxamide (32); 7-cyano-4-((cyclopropylmethyl)amino)-N-(3-hydroxy-3-methylbutyl)-5H-pyrido[3,2-b] indole-3-carboxamide (33); 7-cyano-N-(2-cyclopropylethyl)-4-(isopropylamino)-5H-pyrido[3,2-b]indole-3-carboxamide (34); 7-cyano-4-(isopropylamino)-N-(2-morpholinoethyl)-5H-pyrido[3,2-b]indole-3-carboxamide (35); 7-cyano-4-((2,2-difluoroethyl)amino)-N-(3-hydroxy-3-methylbutyl)-5H-pyrido[3,2-b]indole-3-carboxamide (36); 7-cyano-N-(3-hydroxy-3-methylbutyl)-4-((2,2,2-trifluoroethyl) amino)-5H-pyrido[3,2-b]indole-3-carboxamide (37); 7-cyano-N-(3-fluoro-3-methylbutyl)-4-(isopropylamino)-5H-pyrido[3,2-b]indole-3-carboxamide (38); 7-cyano-N-((1R,3R)-3-(2-hydroxypropan-2-yl)cyclobutyl)-4-(isopropylamino)-5H-pyrido[3,2-b] indole-3-carboxamide (39); 4-(tert-butylamino)-7-cyano-N-(3-hydroxy-3-methylbutyl)-5H-pyrido[3,2-b]indole-3-carboxamide (40); 7-cyano-N-(3-hydroxy-3-methylbutyl) (oxetan-3-ylamino)-5H-pyrido[3,2-b]indole-3-carboxamide (41); 7-cyano-4-(oxetan ylamino)-N-(3,3,3-trifluoropropyl)-5H-pyrido[3,2-b]indole-3-carboxamide (42); 7-cyano-N-(2-(3,3-difluoro-1-hydroxycyclobutyl)ethyl)-4-(isopropylamino)-5H-pyrido[3,2-b]indole-3-carboxamide (43); 7-cyano-4-(cyclopropylamino)-N-((1R,3R)-3-(2-hydroxypropan-2-yl)cyclobutyl)-5H-pyrido[3,2-b]indole-3-carboxamide (44); 7-cyano (cyclopropylamino)-N-((1R,3R)-3-hydroxycyclobutyl)-5H-pyrido[3,2-b]indole carboxamide (45); 7-cyano-4-(cyclopropylamino)-N-(3-hydroxy-3-methylbutyl)-5H-pyrido[3,2-b]indole-3-carboxamide (46); N-((1R,3R)-3-aminocyclobutyl)-7-cyano (isopropylamino)-5H-pyrido[3,2-b]indole-3-carboxamide (47); N3-(3-hydroxy-3-methylbutyl)-4-(isopropylamino)-5H-pyrido[3,2-b]indole-3,7-dicarboxamide (48); N-((1R,3R)-3-acetamidocyclobutyl)-7-cyano-4-(isopropylamino)-5H-pyrido[3,2-b]indole-3-carboxamide (49); methyl ((1R,3R)-3-(7-cyano-4-(isopropylamino)-5H-pyrido[3,2-b] indole-3-carboxamido)cyclobutyl)carbamate (50); N-(3-amino-2,2-difluoropropyl)-7-cyano-4-(isopropylamino)-5H-pyrido[3,2-b]indole-3-carboxamide (51); N-(3-amino-3-methylbutyl)-7-cyano-4-(isopropylamino)-5H-pyrido[3,2-b]indole-3-carboxamide (52); 7-cyano-4-(isopropylamino)-N-(2-(pyrrolidin-3-yl)ethyl)-5H-pyrido[3,2-b]indole-3-carboxamide (53); 4-amino-7-cyano-N-(3-hydroxy-3-methylbutyl)-5H-pyrido[3,2-b] indole-3-carboxamide (54); 7-cyano-4-(ethylamino)-N-(2-(piperidin-3-yl)ethyl)-5H-pyrido[3,2-b]indole-3-carboxamide (55); 7-cyano-4-((3,4-dimethoxybenzyl)amino)-N-(3-hydroxy-3-methylbutyl)-5H-pyrido[3,2-b]indole-3-carboxamide (56); 7-cyano-4-(ethylamino)-N-(2-(pyrrolidin-2-yl)ethyl)-5H-pyrido[3,2-b]indole-3-carboxamide (57); 7-cyano-4-(ethylamino)-N-(2-(piperidin-2-yl)ethyl)-5H-pyrido[3,2-b]indole-3-carboxamide (58); 7-cyano-N-(3-(cyclopropanecarboxamido)-3-methylbutyl)-4-(isopropylamino)-5H-pyrido[3,2-b]indole-3-carboxamide (59); N-(3-acetamido-3-methylbutyl)-7-cyano-4-(isopropylamino)-5H-pyrido[3,2-b]indole-3-carboxamide (60); 7-cyano-N-((1,1-dioxidotetrahydrothiophen-3-yl)methyl)-4-(isopropylamino)-5H-pyrido[3,2-b]indole-3-carboxamide (61); 7-cyano-N-(2-(1,1-dioxidothiomorpholino) ethyl)-4-(isopropylamino)-5H-pyrido[3,2-b]indole-3-carboxamide (62); 7-cyano-4-(isopropylamino)-N-(1-(methylsulfonyl)piperidin-4-yl)-5H-pyrido[3,2-b]indole-3-carboxamide (63); (R)-7-cyano-N-(2-fluoro-3-hydroxy-3-methylbutyl)-4-((1-(methylsulfonyl)piperidin-4-yl)amino)-5H-pyrido[3,2-b]indole-3-carboxamide (64); N-(2-(1H-tetrazol-5-yl)ethyl)-7-cyano-4-(isopropylamino)-5H-pyrido[3,2-b]indole-3-carboxamide (65); (R)—N-(2-fluoro-3-hydroxy-3-methylbutyl)-4-(isopropylamino)-7-(thiazol-5-yl)-5H-pyrido[3,2-b]indole carboxamide (66); (R)—N-(2-fluoro-3-hydroxy-3-methylbutyl)-4-(isopropylamino)-7-(1H-pyrazol-4-yl)-5H-pyrido[3,2-b]indole-3-carboxamide (67); (R)—N-(2-fluoro-3-hydroxy methylbutyl)-4-(isopropylamino)-7-(6-oxo-1,6-dihydropyridin-3-yl)-5H-pyrido[3,2-b]indole-3-carboxamide (68); (R)-7-cyano-N-(2-fluoro-3-hydroxy-3-methylbutyl) (isopropylamino)-5H-pyrrolo[3,2-b:4,5-b'] dipyridine-3-carboxamide (69); 3-(5-isobutyl-1H-1,2,4-triazol-3-yl)-4-(isopropylamino)-5H-pyrido[3,2-b] indole-7-carbonitrile, TFA (70); 4-(isopropylamino)-3-(5-propyl-1H-1,2,4-triazol-3-yl)-5H-pyrido[3,2-b]indole carbonitrile (71); 4-(isopropylamino)-3-(3-propyl-1,2,4-oxadiazol-5-yl)-5H-pyrido[3,2-b]indole-7-carbonitrile (72); 3-(1-isopentyl-1H-1,2,3-triazol-4-yl)-4-(isopropylamino)-5H-pyrido[3,2-b]indole-7-carbonitrile (73); 3-(1-(cyclopropylmethyl)-1H-1,2,3-triazol-4-yl)-4-(isopropylamino)-5H-pyrido[3,2-b] indole-7-carbonitrile (74); 4-(isopropylamino)-3-(1-(piperidin-4-yl)-1H-1,2,3-triazol-4-yl)-5H-pyrido[3,2-b]indole-7-carbonitrile (75); 4-(isopropylamino)-3-(3-(piperidin-4-yl) isoxazol-5-yl)-5H-pyrido[3,2-b]indole-7-carbonitrile (76); 4-(isopropylamino)-3-(3-(tetrahydro-2H-pyran-4-yl)isoxazol-5-yl)-5H-pyrido[3,2-b]indole-7-carbonitrile (77); 4-(isopropylamino)-3-(3-(morpholin-2-yl) isoxazol-5-yl)-5H-pyrido[3,2-b]indole-7-carbonitrile (78); 4-(isopropylamino)-3-(3-(piperidin-3-yl) isoxazol-5-yl)-5H-pyrido[3,2-b]indole-7-carbonitrile (79); 4-(isopropylamino)-3-(3-(piperidin-2-yl)isoxazol-5-yl)-5H-pyrido[3,2-b]indole-7-carbonitrile (80); (R)-6-cyano-N-(2-fluoro-3-hydroxy-3-methylbutyl)-4-(isopropylamino)-9H-pyrido[2,3-b]indole-3-carboxamide (81); or 6-cyano-N-(2-cyclopropylethyl)-4-(isopropylamino)-9H-pyrido[2,3-b] indole-3-carboxamide (82).

One embodiment provides compounds of the Formula (I) having IRAK4 $IC_{50}$ values of ≤0.6 µM.

One embodiment provides compounds of the Formula (I) having IRAK4 $IC_{50}$ values of ≤0.1 µM.

One embodiment provides compounds of the Formula (I) having IRAK4 $IC_{50}$ values of ≤0.05 µM.

One embodiment provides compounds of the Formula (I) having IRAK4 $IC_{50}$ values of ≤0.025 µM.

One embodiment provides compounds of the Formula (I) having IRAK4 $IC_{50}$ values of ≤0.015 µM.

One embodiment provides compounds of the Formula (I) having IRAK4 $IC_{50}$ values of ≤0.01 µM.

One embodiment provides compounds of the Formula (II) having IRAK4 $IC_{50}$ values of ≤0.6 µM.

One embodiment provides compounds of the Formula (II) having IRAK4 $IC_{50}$ values of ≤0.1 µM.

One embodiment provides compounds of the Formula (II) having IRAK4 $IC_{50}$ values of ≤0.05 µM.

One embodiment provides compounds of the Formula (II) having IRAK4 $IC_{50}$ values of ≤0.025 µM.

One embodiment provides compounds of the Formula (II) having IRAK4 $IC_{50}$ values of ≤0.015 µM.

One embodiment provides compounds of the Formula (II) having IRAK4 $IC_{50}$ values of ≤0.01 µM.

Definitions

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

As used herein, the phase "compounds" refers to at least one compound. For example, a compound of Formula (I) includes a compound of Formula (I) and two or more compounds of Formula (I).

Unless otherwise indicated, any heteroatom with unsatisfied valences is assumed to have hydrogen atoms sufficient to satisfy the valences.

The definitions set forth herein take precedence over definitions set forth in any patent, patent application, and/or patent application publication incorporated herein by reference.

Listed below are definitions of various terms used to describe the present invention. These definitions apply to the terms as they are used throughout the specification (unless they are otherwise limited in specific instances) either individually or as part of a larger group.

Throughout the specification, groups and substituents thereof may be chosen by one skilled in the field to provide stable moieties and compounds.

In accordance with a convention used in the art,

is used in structural formulas herein to depict the bond that is the point of attachment of the moiety or substituent to the core or backbone structure.

The terms "halo" and "halogen," as used herein, refer to F, Cl, Br, and I.

The term "cyano" refers to the group —CN.
The term "amino" refers to the group —NH$_2$.
The term "oxo" refers to the group =O.

The term "alkyl" as used herein, refers to both branched and straight-chain saturated aliphatic hydrocarbon groups containing, for example, from 1 to 12 carbon atoms, from 1 to 6 carbon atoms, and from 1 to 4 carbon atoms. Examples of alkyl groups include, but are not limited to, methyl (Me), ethyl (Et), propyl (e.g., n-propyl and i-propyl), butyl (e.g., n-butyl, i-butyl, sec-butyl, and t-butyl), and pentyl (e.g., n-pentyl, isopentyl, neopentyl), n-hexyl, 2-methylpentyl, 2-ethylbutyl, 3-methylpentyl, and 4-methylpentyl. When numbers appear in a subscript after the symbol "C", the subscript defines with more specificity the number of carbon atoms that a particular group may contain. For example, "$C_{1-6}$ alkyl" denotes straight and branched chain alkyl groups with one to six carbon atoms.

The term "fluoroalkyl" as used herein is intended to include both branched and straight-chain saturated aliphatic hydrocarbon groups substituted with one or more fluorine atoms. For example, "$C_{1-4}$ fluoroalkyl" is intended to include $C_1$, $C_2$, $C_3$, and $C_4$ alkyl groups substituted with one or more fluorine atoms. Representative examples of fluoroalkyl groups include, but are not limited to, —CF$_3$ and —CH$_2$CF$_3$.

The term "hydroxyalkyl" includes both branched and straight chain saturated alkyl groups substituted with one or more hydroxyl groups. For example, "hydroxyalkyl" includes —CH$_2$OH, —CH$_2$CH$_2$OH, and $C_{1-4}$ hydroxyalkyl.

The term "cycloalkyl," as used herein, refers to a group derived from a non-aromatic monocyclic or polycyclic hydrocarbon molecule by removal of one hydrogen atom from a saturated ring carbon atom. Representative examples of cycloalkyl groups include, but are not limited to, cyclopropyl, cyclopentyl, and cyclohexyl. When numbers appear in a subscript after the symbol "C", the subscript defines with more specificity the number of carbon atoms that a particular cycloalkyl group may contain. For example, "$C_{3-6}$ cycloalkyl" denotes cycloalkyl groups with three to six carbon atoms.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds of Formula (I) and Formula (II) can be provided as amorphous solids or crystalline solids. Lyophilization can be employed to provide the compounds of Formula (I) and Formula (II) as amorphous solids.

It should further be understood that solvates (e.g., hydrates) of the compounds of Formula (I) and Formula (II) are also within the scope of the present invention. The term "solvate" means a physical association of a compound of Formula (I) or a compound of Formula (II) with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, isopropanolates, acetonitrile solvates, and ethyl acetate solvates. Methods of solvation are known in the art.

Various forms of prodrugs are well known in the art and are described in Rautio, J. et al., *Nature Review Drug Discovery*, 17, 559-587 (2018).

In addition, compounds of Formula (I) and Formula (II), subsequent to their preparation, can be isolated and purified to obtain a composition containing an amount by weight equal to or greater than 99% of a compound of Formula (I) and Formula (II), respectively ("substantially pure"), which is then used or formulated as described herein. Such "substantially pure" compounds of Formula (I) and "substantially pure" compounds of Formula (II) are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to act as an inhibitor to IRAK4; or effective to treat or prevent autoimmune and/or inflammatory disease states, such as multiple sclerosis and rheumatoid arthritis; or effective to treat cancer.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

The compounds of the present invention are intended to include all isotopes of atoms occurring in the present compounds. Isotopes include those atoms having the same atomic number but different mass numbers. By way of general example and without limitation, isotopes of hydrogen include deuterium (D) and tritium (T). Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed. For example, methyl (—CH$_3$) also includes deuterated methyl groups such as —CD$_3$.

Utility

The compounds of the invention modulate kinase activity, including the modulation of IRAK-4. Other types of kinase activity that may be modulated by the compounds of the instant invention include, but are not limited to, the Pelle/IRAK family and mutants thereof.

Accordingly, compounds of Formula (I) and Formula (II) have utility in treating conditions associated with the modulation of kinase activity, and particularly the selective inhibition of IRAK-4 activity or the inhibition of IRAK and other Pelle family kinases. Such conditions include TLR/IL-1family receptor associated diseases in which cytokine levels are modulated as a consequence of intracellular signaling. Moreover, the compounds of Formula (I) and Formula (II) have advantageous selectivity for IRAK-4 activity, preferably from at least 20 fold to over 1,000 fold more selective.

As used herein, the terms "treating" or "treatment" encompass the treatment of a disease state in a mammal, particularly in a human, and include: (a) preventing or delaying the occurrence of the disease state in a mammal, in particular, when such mammal is predisposed to the disease state but has not yet been diagnosed as having it; (b) inhibiting the disease state, i.e., arresting its development; and/or (c) achieving a full or partial reduction of the symptoms or disease state, and/or alleviating, ameliorating, lessening, or curing the disease or disorder and/or its symptoms.

In view of their activity as selective inhibitors IRAK-4, compounds of Formula (I) and Formula (II) are useful in treating TLR/IL-1 family receptor associated diseases, but not limited to, inflammatory diseases such as Crohn's disease, ulcerative colitis, asthma, graft versus host disease, allograft rejection, chronic obstructive pulmonary disease; autoimmune diseases such as Graves' disease, rheumatoid arthritis, systemic lupus erythematosus, psoriasis; auto-inflammatory diseases including CAPS, TRAPS, FMF, adult onset stills, systemic onset juvenile idiopathic arthritis, gout, gouty arthritis; metabolic diseases including type 2 diabetes, atherosclerosis, myocardial infarction; destructive bone disorders such as bone resorption disease, osteoarthritis, osteoporosis, multiple myeloma-related bone disorder; proliferative disorders such as acute myelogenous leukemia, chronic myelogenous leukemia; angiogenic disorders such as angiogenic disorders including solid tumors, ocular neovasculization, and infantile haemangiomas; infectious diseases such as sepsis, septic shock, and Shigellosis; neurodegenerative diseases such as Alzheimer's disease, Parkinson's disease, cerebral ischemias or neurodegenerative disease caused by traumatic injury, oncologic and viral diseases such as metastatic melanoma, Kaposi's sarcoma, multiple myeloma, and HIV infection and CMV retinitis, AIDS, respectively.

More particularly, the specific conditions or diseases that may be treated with the inventive compounds include, without limitation, pancreatitis (acute or chronic), asthma, allergies, adult respiratory distress syndrome, chronic obstructive pulmonary disease, glomerulonephritis, rheumatoid arthritis, systemic lupus erythematosus, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, graft vs. host disease, inflammatory reaction induced by endotoxin, tuberculosis, atherosclerosis, muscle degeneration, cachexia, psoriatic arthritis, Reiter's syndrome, gout, traumatic arthritis, rubella arthritis, acute synovitis, pancreatic β-cell disease; diseases characterized by massive neutrophil infiltration; rheumatoid spondylitis, gouty arthritis and other arthritic conditions, cerebral malaria, chronic pulmonary inflammatory disease, silicosis, pulmonary sarcoidosis, bone resorption disease, allograft rejections, fever and myalgias due to infection, cachexia secondary to infection, keloid formation, scar tissue formation, ulcerative colitis, pyresis, influenza, osteoporosis, osteoarthritis, acute myelogenous leukemia, chronic myelogenous leukemia, metastatic melanoma, Kaposi's sarcoma, multiple myeloma, sepsis, septic shock, and Shigellosis; Alzheimer's disease, Parkinson's disease, cerebral ischemias or neurodegenerative disease caused by traumatic injury; angiogenic disorders including solid tumors, ocular neovasculization, and infantile haemangiomas; viral diseases including acute hepatitis infection (including hepatitis A, hepatitis B and hepatitis C), HIV infection and CMV retinitis, AIDS, ARC or malignancy, and herpes; stroke, myocardial ischemia, ischemia in stroke heart attacks, organ hypoxia, vascular hyperplasia, cardiac and renal reperfusion injury, thrombosis, cardiac hypertrophy, thrombin-induced platelet aggregation, endotoxemia and/or toxic shock syndrome, conditions associated with prostaglandin endoperoxidase syndase-2, and pemphigus vulgaris. Preferred methods of treatment are those wherein the condition is selected from Crohn's disease, ulcerative colitis, allograft rejection, rheumatoid arthritis, psoriasis, ankylosing spondylitis, psoriatic arthritis, and pemphigus vulgaris. Alternatively preferred methods of treatment are those wherein the condition is selected from ischemia reperfusion injury, including cerebral ischemia reperfusions injury arising from stroke and cardiac ischemia reperfusion injury arising from myocardial infarction. Another preferred method of treatment is one in which the condition is multiple myeloma.

In one embodiment, the compounds of Formula (I) and Formula (II) are useful in treating cancer, including Waldenstrom's Macroglobulinemia (WM), diffuse large B cell lymphoma (DLBCL), chronic lymphocytic leukemia (CLL), cutaneous diffuse large B cell lymphoma, and primary CNS lymphoma.

In addition, the kinase inhibitors of the present invention inhibit the expression of inducible pro-inflammatory proteins such as prostaglandin endoperoxide synthase-2 (PGHS-2), also referred to as cyclooxygenase-2 (COX-2), IL-1, IL-6, IL-18, chemokines. Accordingly, additional IRAK-4-associated conditions include edema, analgesia, fever and pain, such as neuromuscular pain, headache, pain caused by cancer, dental pain and arthritis pain. The inventive compounds also may be used to treat veterinary viral infections, such as lentivirus infections, including, but not limited to equine infectious anemia virus; or retrovirus infections, including feline immunodeficiency virus, bovine immunodeficiency virus, and canine immunodeficiency virus.

When the terms "IRAK-4-associated condition" or "IRAK-4-associated disease or disorder" are used herein, each is intended to encompass all of the conditions identified above as if repeated at length, as well as any other condition that is affected by IRAK-4 kinase activity.

The present invention thus provides methods for treating such conditions, comprising administering to a subject in need thereof a therapeutically-effective amount of at least one compound of Formula (I) or Formula (II) or a salt thereof "Therapeutically effective amount" is intended to include an amount of a compound of the present invention that is effective when administered alone or in combination to inhibit IRAK-4 and/or treat diseases.

The methods of treating IRAK-4 kinase-associated conditions may comprise administering compounds of Formula (I) alone, compounds of Formula (II) alone, or in combination with each other and/or other suitable therapeutic agents useful in treating such conditions. Accordingly, "therapeutically effective amount" is also intended to include an amount of the combination of compounds claimed that is effective to inhibit IRAK-4 and/or treat diseases associated with IRAK-4.

Exemplary of such other therapeutic agents include corticosteroids, rolipram, calphostin, cytokine-suppressive anti-inflammatory drugs (CSAIDs), Interleukin-10, glucocorticoids, salicylates, nitric oxide, and other immunosuppressants; nuclear translocation inhibitors, such as deoxyspergualin (DSG); non-steroidal anti-inflammatory drugs (NSAIDs) such as ibuprofen, celecoxib and rofecoxib; steroids such as prednisone or dexamethasone; antiviral agents such as abacavir; antiproliferative agents such as methotrexate, leflunomide, FK506 (tacrolimus, PROGRAF®); anti-malarials such as hydroxychloroquine; cytotoxic drugs such as azathiprine and cyclophosphamide; TNF-α inhibitors such as tenidap, anti-TNF antibodies or soluble TNF receptor, and rapamycin (sirolimus or RAPAMUNE®) or derivatives thereof.

The above other therapeutic agents, when employed in combination with the compounds of the present invention, may be used, for example, in those amounts indicated in the Physicians' Desk Reference (PDR) or as otherwise determined by one of ordinary skill in the art. In the methods of the present invention, such other therapeutic agent(s) may be administered prior to, simultaneously with, or following the administration of the inventive compounds. The present invention also provides pharmaceutical compositions capable of treating IRAK-4 kinase-associated conditions, including TLR and IL-1 family receptor mediated diseases as described above.

The inventive compositions may contain other therapeutic agents as described above and may be formulated, for example, by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulation.

Accordingly, the present invention further includes compositions comprising one or more compounds of Formula (I) and/or Formula (II) and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include without limitation the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences*, 17th Edition (1985), which is incorporated herein by reference in its entirety.

Compounds in accordance with Formula (I) can be administered by any means suitable for the condition to be treated, which can depend on the need for site-specific treatment or quantity of Formula (I) compound to be delivered.

Compounds in accordance with Formula (II) can be administered by any means suitable for the condition to be treated, which can depend on the need for site-specific treatment or quantity of Formula (II) compound to be delivered.

Also embraced within this invention is a class of pharmaceutical compositions comprising a compound of Formula (II) and/or a compound of Formula (II), and one or more non-toxic, pharmaceutically-acceptable carriers and/or diluents and/or adjuvants (collectively referred to herein as "carrier" materials) and, if desired, other active ingredients. The compounds of Formula (I) and Formula (II) may be administered by any suitable route, preferably in the form of a pharmaceutical composition adapted to such a route, and in a dose effective for the treatment intended. The compounds and compositions of the present invention may, for example, be administered orally, mucosally, or parentally including intravascularly, intravenously, intraperitoneally, subcutaneously, intramuscularly, and intrasternally in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g. magnesium stearate and a disintegrating agent such as crospovidone. The carrier mixture may be filled into a gelatin capsule or compressed as a tablet. The pharmaceutical composition may be administered as an oral dosage form or an infusion, for example.

For oral administration, the pharmaceutical composition may be in the form of, for example, a tablet, capsule, liquid capsule, suspension, or liquid. The pharmaceutical composition is preferably made in the form of a dosage unit containing a particular amount of the active ingredient. For example, the pharmaceutical composition may be provided as a tablet or capsule comprising an amount of active ingredient in the range of from about 0.1 to 1000 mg, preferably from about 0.25 to 250 mg, and more preferably from about 0.5 to 100 mg. A suitable daily dose for a human or other mammal may vary widely depending on the condition of the patient and other factors, but, can be determined using routine methods.

Any pharmaceutical composition contemplated herein can, for example, be delivered orally via any acceptable and suitable oral preparations. Exemplary oral preparations, include, but are not limited to, for example, tablets, troches, lozenges, aqueous and oily suspensions, dispersible powders or granules, emulsions, hard and soft capsules, liquid capsules, syrups, and elixirs. Pharmaceutical compositions intended for oral administration can be prepared according to any methods known in the art for manufacturing pharmaceutical compositions intended for oral administration. In order to provide pharmaceutically palatable preparations, a pharmaceutical composition in accordance with the invention can contain at least one agent selected from sweetening agents, flavoring agents, coloring agents, demulcents, antioxidants, and preserving agents.

A tablet can, for example, be prepared by admixing at least one compound of Formula (I) and/or Formula (II) with at least one non-toxic pharmaceutically acceptable excipient suitable for the manufacture of tablets. Exemplary excipients include, but are not limited to, for example, inert diluents, such as, for example, calcium carbonate, sodium carbonate, lactose, calcium phosphate, and sodium phosphate; granulating and disintegrating agents, such as, for example, microcrystalline cellulose, sodium crosscarmellose, corn starch, and alginic acid; binding agents, such as, for example, starch, gelatin, polyvinyl-pyrrolidone, and acacia; and lubricating agents, such as, for example, magnesium stearate, stearic acid, and talc. Additionally, a tablet can either be uncoated, or coated by known techniques to either mask the bad taste of an unpleasant tasting drug, or delay disintegration and absorption of the active ingredient in the gastrointestinal tract thereby sustaining the effects of the active ingredient for a longer period. Exemplary water soluble taste masking materials, include, but are not limited to, hydroxypropyl-methylcellulose and hydroxypropyl-cellulose. Exemplary time delay materials, include, but are not limited to, ethyl cellulose and cellulose acetate butyrate.

Hard gelatin capsules can, for example, be prepared by mixing at least one compound of Formula (I) and/or Formula (II) with at least one inert solid diluent, such as, for example, calcium carbonate; calcium phosphate; and kaolin.

Soft gelatin capsules can, for example, be prepared by mixing at least one compound of Formula (I) and/or Formula (II) with at least one water soluble carrier, such as, for example, polyethylene glycol; and at least one oil medium, such as, for example, peanut oil, liquid paraffin, and olive oil.

An aqueous suspension can be prepared, for example, by admixing at least one compound of Formula (I) and/or Formula (II) with at least one excipient suitable for the manufacture of an aqueous suspension. Exemplary excipients suitable for the manufacture of an aqueous suspension, include, but are not limited to, for example, suspending agents, such as, for example, sodium carboxymethylcellulose, methylcellulose, hydroxypropylmethyl-cellulose, sodium alginate, alginic acid, polyvinyl-pyrrolidone, gum tragacanth, and gum acacia; dispersing or wetting agents, such as, for example, a naturally-occurring phosphatide, e.g., lecithin; condensation products of alkylene oxide with fatty acids, such as, for example, polyoxyethylene stearate; condensation products of ethylene oxide with long chain aliphatic alcohols, such as, for example heptadecaethyleneoxycetanol; condensation products of ethylene oxide with partial esters derived from fatty acids and hexitol, such as, for example, polyoxyethylene sorbitol monooleate; and condensation products of ethylene oxide with partial esters derived from fatty acids and hexitol anhydrides, such as, for example, polyethylene sorbitan monooleate. An aqueous suspension can also contain at least one preservative, such as, for example, ethyl and n-propyl p-hydroxybenzoate; at least one coloring agent; at least one flavoring agent; and/or at least one sweetening agent, including but not limited to, for example, sucrose, saccharin, and aspartame.

Oily suspensions can, for example, be prepared by suspending at least one compound of Formula (I) and/or Formula (II) in either a vegetable oil, such as, for example, arachis oil; olive oil; sesame oil; and coconut oil; or in mineral oil, such as, for example, liquid paraffin. An oily suspension can also contain at least one thickening agent, such as, for example, beeswax; hard paraffin; and cetyl alcohol. In order to provide a palatable oily suspension, at least one of the sweetening agents already described hereinabove, and/or at least one flavoring agent can be added to the oily suspension. An oily suspension can further contain at least one preservative, including, but not limited to, for example, an anti-oxidant, such as, for example, butylated hydroxyanisol, and alpha-tocopherol.

Dispersible powders and granules can, for example, be prepared by admixing at least one compound of Formula (I) and/or Formula (II) with at least one dispersing and/or wetting agent; at least one suspending agent; and/or at least one preservative. Suitable dispersing agents, wetting agents, and suspending agents are as already described above. Exemplary preservatives include, but are not limited to, for example, anti-oxidants, e.g., ascorbic acid. In addition, dispersible powders and granules can also contain at least one excipient, including, but not limited to, for example, sweetening agents; flavoring agents; and coloring agents.

An emulsion of at least one compound of Formula (I) and/or Formula (II) thereof can, for example, be prepared as an oil-in-water emulsion. The oily phase of the emulsions comprising compounds of Formula (I) and/or Formula (II) may be constituted from known ingredients in a known manner. The oil phase can be provided by, but is not limited to, for example, a vegetable oil, such as, for example, olive oil and *arachis* oil; a mineral oil, such as, for example, liquid paraffin; and mixtures thereof. While the phase may comprise merely an emulsifier, it may comprise a mixture of at least one emulsifier with a fat or an oil or with both a fat and an oil. Suitable emulsifying agents include, but are not limited to, for example, naturally-occurring phosphatides, e.g., soy bean lecithin; esters or partial esters derived from fatty acids and hexitol anhydrides, such as, for example, sorbitan monooleate; and condensation products of partial esters with ethylene oxide, such as, for example, polyoxyethylene sorbitan monooleate. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. An emulsion can also contain a sweetening agent, a flavoring agent, a preservative, and/or an antioxidant. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The compounds of Formula (I) and/or Formula (II) can, for example, also be delivered intravenously, subcutaneously, and/or intramuscularly via any pharmaceutically acceptable and suitable injectable form. Exemplary injectable forms include, but are not limited to, for example, sterile aqueous solutions comprising acceptable vehicles and solvents, such as, for example, water, Ringer's solution, and isotonic sodium chloride solution; sterile oil-in-water microemulsions; and aqueous or oleaginous suspensions.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e. Captisol), cosolvent solubilization (i.e. propylene glycol) or micellar solubilization (i.e. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

A sterile injectable oil-in-water microemulsion can, for example, be prepared by 1) dissolving at least one compound of Formula (I) and/or Formula (II) in an oily phase, such as, for example, a mixture of soybean oil and lecithin; 2) combining the Formula (I) and/or Formula (II) containing oil phase with a water and glycerol mixture; and 3) processing the combination to form a microemulsion.

A sterile aqueous or oleaginous suspension can be prepared in accordance with methods already known in the art. For example, a sterile aqueous solution or suspension can be prepared with a non-toxic parenterally-acceptable diluent or solvent, such as, for example, 1,3-butane diol; and a sterile oleaginous suspension can be prepared with a sterile non-toxic acceptable solvent or suspending medium, such as, for example, sterile fixed oils, e.g., synthetic mono- or diglycerides; and fatty acids, such as, for example, oleic acid.

Pharmaceutically acceptable carriers, adjuvants, and vehicles that may be used in the pharmaceutical compositions of this invention include, but are not limited to, ion exchangers, alumina, aluminum stearate, lecithin, self-emulsifying drug delivery systems (SEDDS) such as d-alpha-tocopherol polyethyleneglycol 1000 succinate, surfactants used in pharmaceutical dosage forms such as Tweens, polyethoxylated castor oil such as CREMOPHOR surfactant (BASF), or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

The pharmaceutically active compounds of this invention can be processed in accordance with conventional methods of pharmacy to produce medicinal agents for administration to patients, including humans and other mammals. The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The amounts of compounds that are administered and the dosage regimen for treating a disease condition with the compounds and/or compositions of this invention depends on a variety of factors, including the age, weight, sex, the medical condition of the subject, the type of disease, the severity of the disease, the route and frequency of administration, and the particular compound employed. Thus, the dosage regimen may vary widely, but can be determined routinely using standard methods. A daily dose of about 0.001 to 100 mg/kg body weight, preferably between about 0.0025 and about 50 mg/kg body weight and most preferably between about 0.005 to 10 mg/kg body weight, may be appropriate. The daily dose can be administered in one to four doses per day. Other dosing schedules include one dose per week and one dose per two day cycle.

For therapeutic purposes, the active compounds of this invention are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

Pharmaceutical compositions of this invention comprise at least one compound of Formula (I) and optionally an additional agent selected from any pharmaceutically acceptable carrier, adjuvant, and vehicle. Alternate compositions of this invention comprise a compound of the Formula (I) described herein, or a prodrug thereof, and a pharmaceutically acceptable carrier, adjuvant, or vehicle.

Pharmaceutical compositions of this invention comprise at least one compound of Formula (II) and optionally an additional agent selected from any pharmaceutically acceptable carrier, adjuvant, and vehicle. Alternate compositions of this invention comprise a compound of the Formula (II) described herein, or a prodrug thereof, and a pharmaceutically acceptable carrier, adjuvant, or vehicle.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a cardiovascular disorder, diuresis, and/or natriuresis. In another embodiment, the package insert states that the pharmaceutical composition can be used in combination (as defined previously) with a second therapeutic agent to treat cardiovascular disorder, diuresis, and/or natriuresis. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, or other written sheet that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic) on which the desired information has been formed (e.g., printed or applied).

Methods of Preparation

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below.

The reactions and techniques described in this section are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al. (*Protective Groups in Organic Synthesis*, Third Edition, Wiley and Sons (1999)).

Scheme 1 outlines another potential path towards compounds of the general formula 1 starting from an appropriately substituted dichloropyridine 2a-1. Pyridine 2a-1 may be reacted with a variety of amines to afford intermediate 2a-2. Further reaction of 2a-1 using standard cross coupling methodologies may provide the 2-aryl substituted intermediate 2a-3. The nitro group of 2a-3 may be reduced to the amine with a suitable reagent, such as hydrogen in the presence of a palladium catalyst, to provide the amine 2a-4. The final compound may be prepared by heating 2a-4, in a suitable solvent such as NMP or DMA, to temperatures that could affect cyclization, typically >120° C.

cyclize to afford the tricyclic 2b-6. The tricyclic bromide may be reacted with a cyanide transfer reagent to afford 2b-7 and then further reacted with a chlorinating reagent, such as $POCl_3$, to afford 2b-8. Treatment with a variety of nucleophilic amines may provide intermediates such as 2b-9 and the ester functionality may be hydrolyzed using standard saponification conditions to afford 2b-10. Treatment of this acid intermediate with various amines in the presence of amide bond coupling reagents, such as HATU, may provide compounds of the general formula I.

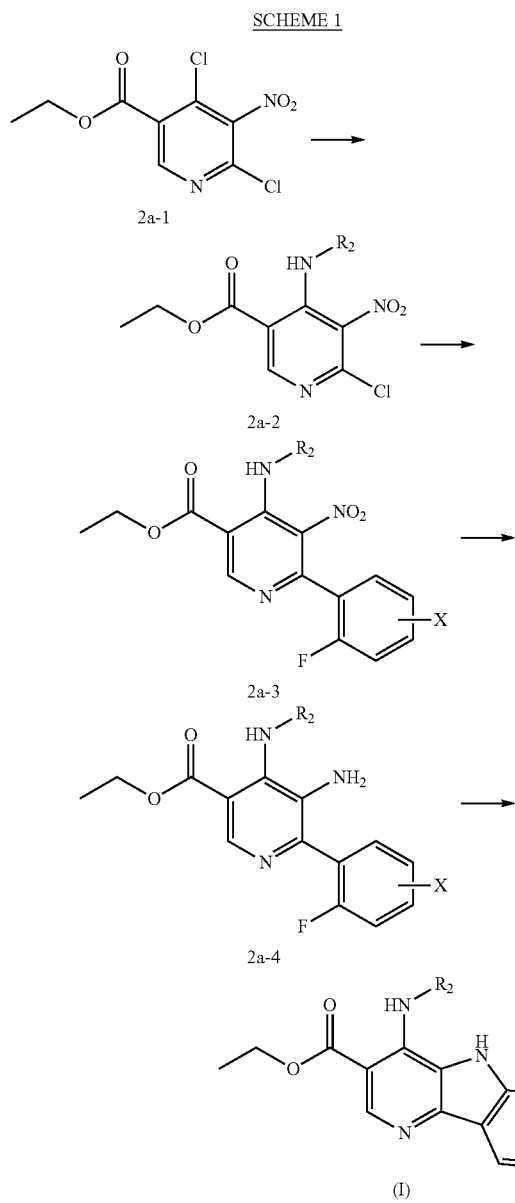

SCHEME 1

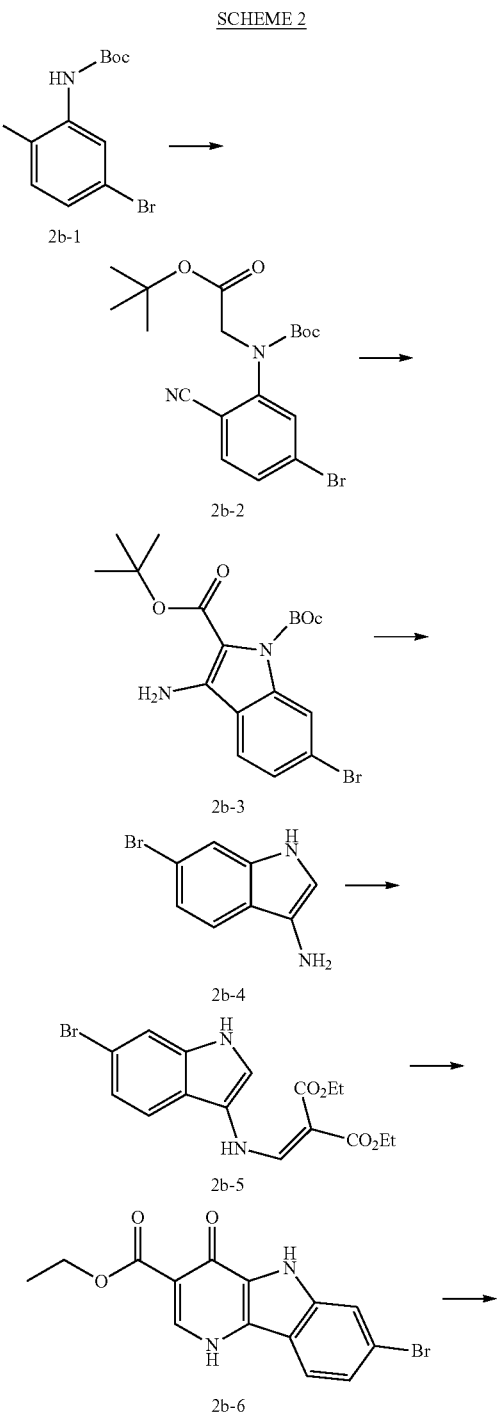

SCHEME 2

Additional compounds of the general formula may be prepared according to the process outlined in Scheme 2. The Boc-amino bromide 2b-1 may be alkylated with a suitable base and alkylating reagent to provide 2b-2. Cyclization of 2b-2 to 2b-3 may be initiated upon reaction with a strong base, such as potassium tert-butoxide in an appropriate solvent such as THF. Decarboxylation to 2b-4 may be affected in the presence of a strong acid such as TFA. Further reaction with diethyl 2-(ethoxymethylene)malonate may afford 2b-5 which upon treatment at high temperatures may

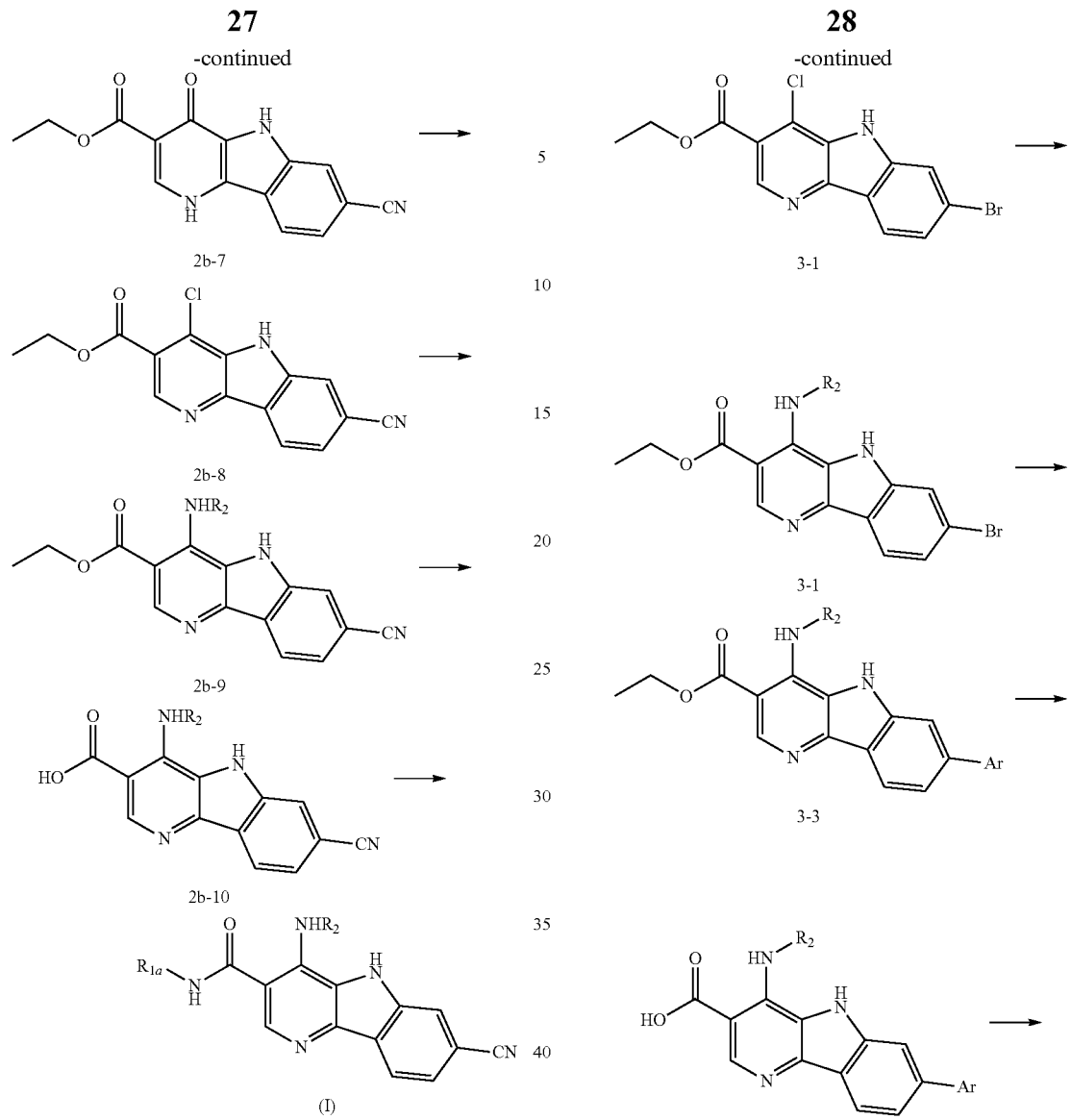

Alternatively, as outlined in Scheme 3, Intermediate 2b-6, may be converted to the chloride 3-1 upon treatment with a chlorinating reagent such as POCl₃ and then further reacted with amines to afford intermediates such as 3-2. Reaction of 3-2 with a variety of aryl cross coupling reagents, such as pyrazole-3-boronic acid, in the presence of a cross coupling catalyst, may afford intermediates such as 3-3. Hydrolysis to 3-4 along the lines as previously described and coupling with an amine for form the amide bond may provide additional compound of the general formula I.

SCHEME 3

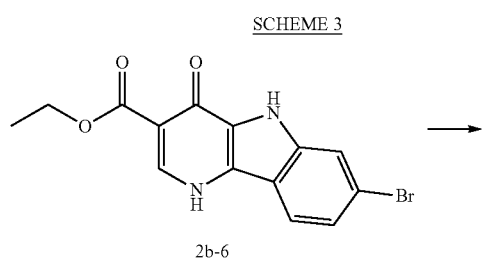

An additional description for the preparation of compounds of the general formula I is outlined in Scheme 4. The nitro azaindole, 4-1, can be reacted with a reducing agent, such as Zn and $NH_4C_1$, to provide the amine 4-2. The amine can be treated with diethyl 2-(ethoxymethylene)malonate to afford 4-3 which may be further cyclized to 4-4 upon heating in the presence of a strong acid, such as PPA. Sequential chlorination and amine displacement may afford intermediates such as 4-5 which can be further reacted with a cyanide transfer reagent to afford intermediate 4-6. Hydrolysis to 4-7 and amide bond forming reaction with a variety of amines may afford additional compounds of the general formula (I).

SCHEME 4

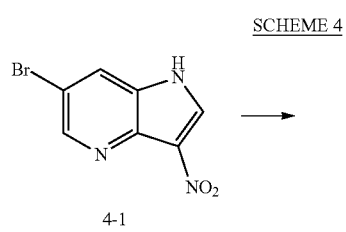

4-1

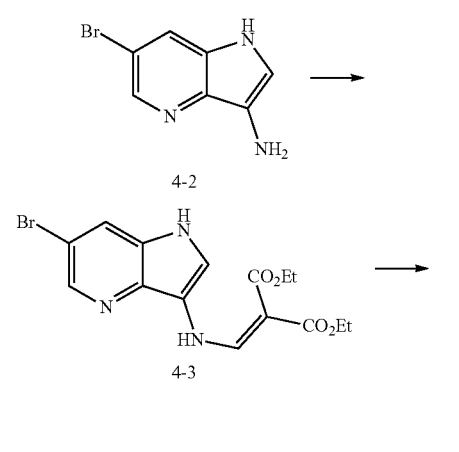

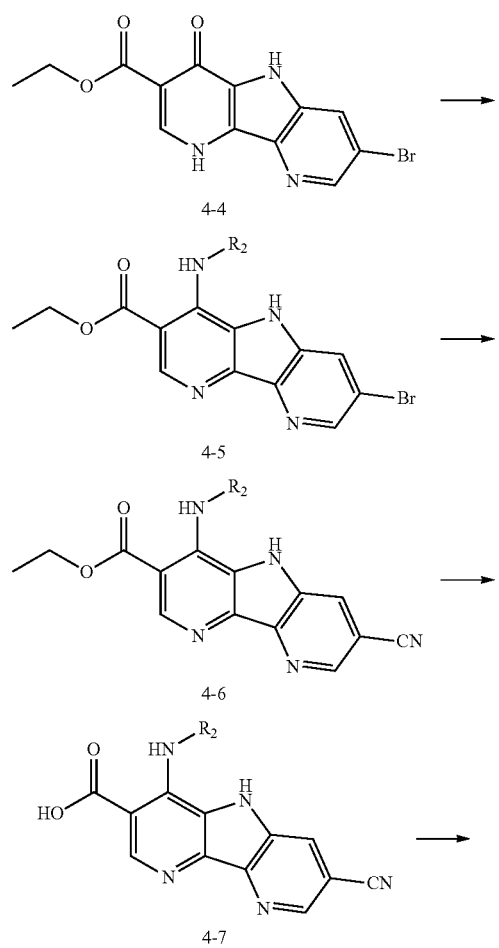

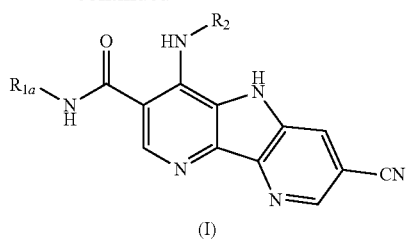

(I)

Scheme 5 highlights the synthesis of 1,2,4 triazole analogs from the acid intermediate 5-1, previously described in the schemes above. Briefly, 5-1 may be reacted with a variety of substituted alkyl imidates followed by hydrazine to afford the triazoles of the general formula (I)

SCHEME 5

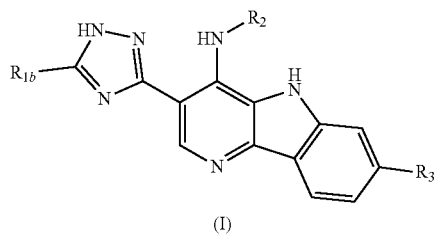

5-1

(I)

Esters of the general intermediate structure 6-1 may be converted to the aldehyde 6-2 with an appropriate reducing agent, such as DIBAL-H, and then further reacted to the alkyne 6-3 using standard methods available in the literature. Treatment of 6-3 with an appropriately substituted azido compound, such as cyclopropyl methyl azide, in the presence of a copper catalyst, may provide compounds of the general formula (I).

SCHEME 6

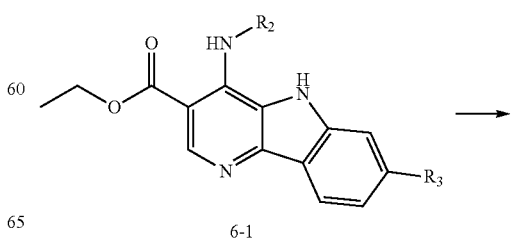

6-1

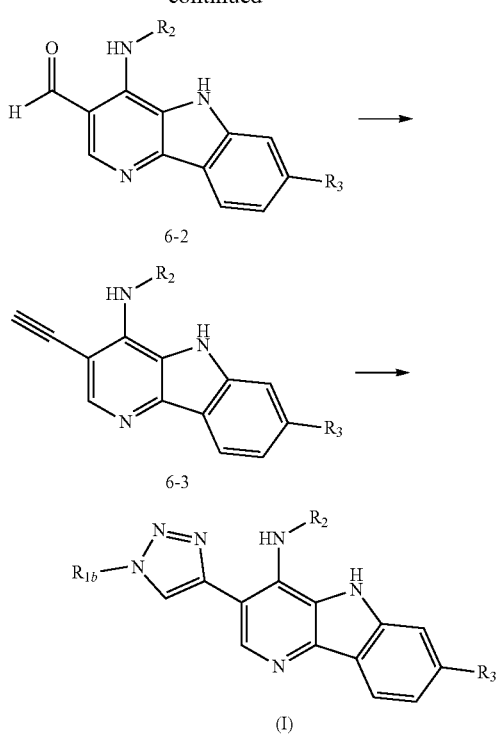

Alternatively, intermediate 6-3, as in Scheme 7, may be reacted with an alkyl chlorooxime in the presence of an amine, such as TEA, to afford additional compounds of the general formula I.

SCHEME 7

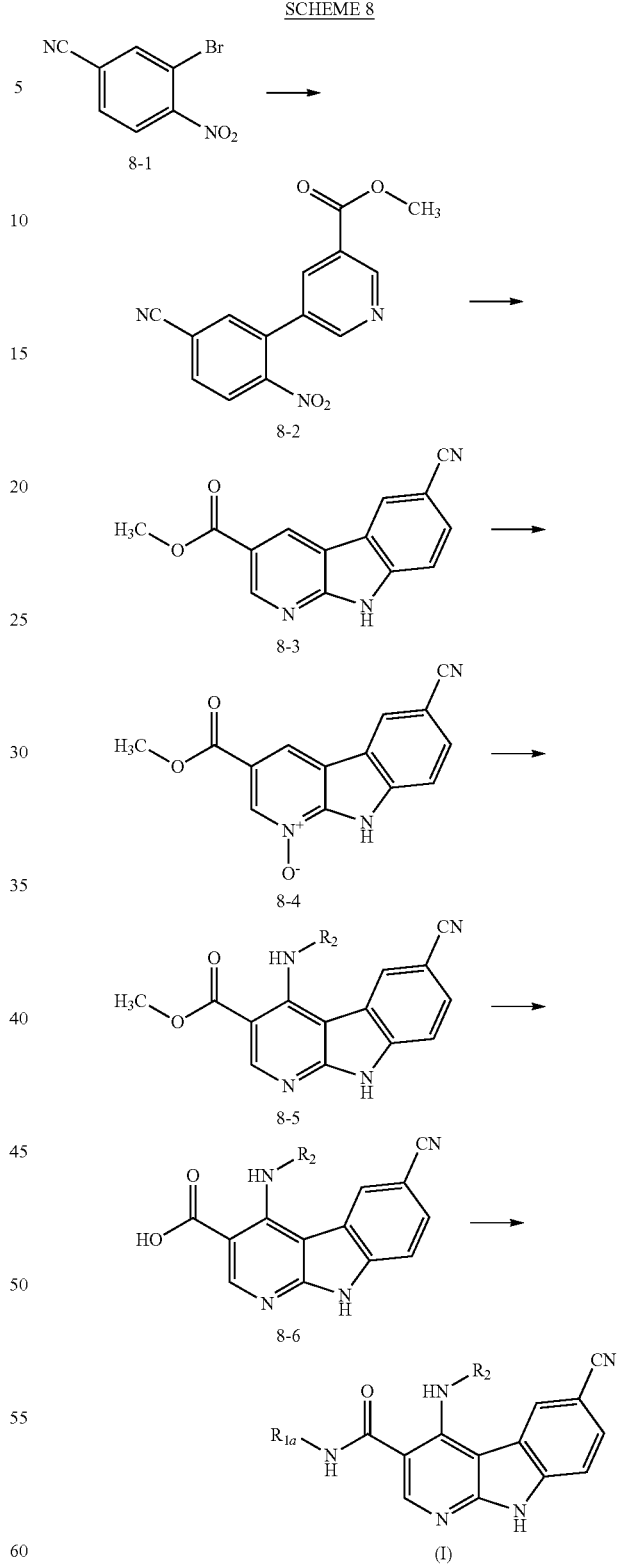

An additional series of compounds may be prepared according the methods outlined in Scheme 8. Aryl bromide 8-1 may be reacted with an appropriately substituted pyridine boronic ester to afford intermediate 8-2. Heating 8-2 in a solvent, such as dichlorobenzene in the presence of DPPE, may afford the cyclized intermediate 8-3. Treatment of 8-3 with an oxidizing agent, such as hydrogen peroxide, may afford N-oxide 8-4 which upon treatment with an amine at elevated temperature may afford 8-5. Hydrolysis to 8-6 and amide bond formation with standard amines may afford additional compound of the general formula (I).

EXAMPLES

Compounds of the current invention and intermediates used in the preparation of compounds of the current invention can be prepared using procedures shown in the following examples and related procedures. The methods and conditions used in these examples, and the actual compounds prepared in these examples, are not meant to be limiting, but are meant to demonstrate how the compounds of the current invention can be prepared. Starting materials and reagents used in these examples, when not prepared by a procedure described herein, are generally either commercially available, or are reported in the chemical literature, or may be prepared by using procedures described in the chemical literature. The invention is further defined in the following Examples. It should be understood that the Examples are given by way of illustration only. From the above discussion and the Examples, one skilled in the art can ascertain the essential characteristics of the invention, and without departing from the spirit and scope thereof, can make various changes and modifications to adapt the invention to various uses and conditions. As a result, the invention is not limited by the illustrative examples set forth herein below, but rather defined by the claims appended hereto.

In the examples given, the phrase "dried and concentrated" generally refers to drying of a solution in an organic solvent over either sodium sulfate or magnesium sulfate, followed by filtration and removal of the solvent from the filtrate (generally under reduced pressure and at a temperature suitable to the stability of the material being Column chromatography was performed with pre-packed silica gel cartridges using an Isco medium pressure chromatography apparatus (Teledyne Corporation), eluting with the solvent or solvent mixture indicated. Preparative high performance liquid chromatography (HPLC) was performed using a reverse phase column (Waters Sunfire $C_{18}$, Waters Xbridge $C_{18}$, PHENOMENEX® Axia $C_{18}$, YMC S5 ODS or the like) of a size appropriate to the quantity of material being separated, generally eluting with a gradient of increasing concentration of methanol or acetonitrile in water, also containing 0.05% or 0.1% trifluoroacetic acid or 10 mM ammonium acetate, at a rate of elution suitable to the column size and separation to be achieved. Chemical names were determined using ChemDraw Ultra, version 9.0.5 (CambridgeSoft). The following abbreviations are used:

aq. aqueous
$BOC_2O$ di-tert-butyl dicarbonate
BOP benzotriazol-1-yloxytris-(dimethylamino)-phosphonium hexafluorophosphate
brine saturated aqueous sodium chloride
DCE dichloroethane
DCM dichloromethane
DIBAL-H diisobutylaluminium hydride
DMA N,N-dimethylacetamide
DMAP dimethylaminopyridine
DMF N,N-dimethylformamide
DMSO dimethyl sulfoxide
DPPF 1,1'-bis(diphenylphosphino)ferrocene
EtOAc ethyl acetate
EtOH ethanol
g gram(s)
h hour(s)
HATU O-(7-azabenzotriazol-1-yl)-N, N, N', N'-tetramethyluronium hexafluorophosphate
HPLC High Performance Liquid Chromatography
LCMS Liquid Chromatography-Mass Spectroscopy
LDA lithium diisopropylamide
MeCN acetonitrile
MeOH methanol
$NH_4OAc$ ammonium acetate
NMP N-methylpyrrolidinone $Pd_2(dba)_3$ tris-(dibenzylideneacetone)dipalladium
$PdCl_2(dppf)$ [1,1'-bis(diphenylphosphino)ferrocene]dichloropalladium(II)
$Pd(PPh_3)_4$ tetrakis(triphenylphosphine)palladium
pet ether petroleum ether
PPA polyphosphoric acid
t-BuOH tert-butanol
TEA triethylamine
TFA trifluoroacetic acid
THF tetrahydrofuran Example 1

(R)-7-cyano-N-(2-fluoro-3-hydroxy-3-methylbutyl)-4-(isopropylamino)-5H-pyrido [3,2-b]indole-3-carboxamide

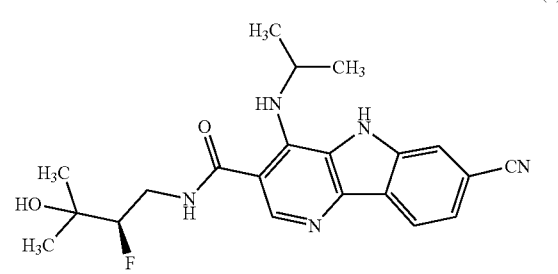

(1)

Method 1

Intermediate 1A: Ethyl 6-chloro-4-(isopropylamino)-5-nitronicotinate

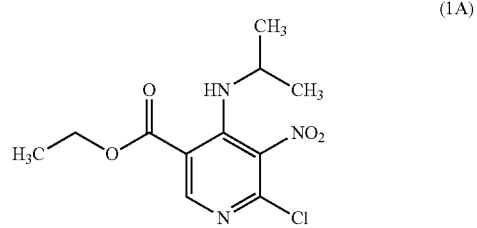 [SMILES: CCOC(=O)c1cnc(Cl)c([N+](=O)[O-])c1NC(C)C]

(1A)

A solution of ethyl 4,6-dichloro-5-nitronicotinate (0.28 g, 1.06 mmol), propan-2-amine (0.066 g, 1.11 mmol), and triethylamine (0.294 mL, 2.11 mmol) in acetonitrile (5 mL) was stirred at room temperature for 2 h. The reaction mixture was diluted with EtOAc, washed with water, dried ($MgSO_4$), and concentrated. The crude material was purified using ISCO flash chromatography (silica gel/hexanes/ethyl acetate 100:0 to 0:100 gradient) to afford ethyl 6-chloro-4-(isopropylamino)-5-nitronicotinate (0.297 g, 98% yield) as a yellow oil. $^1$H NMR (400 MHz, CHLOROFORM-d) δ 8.92 (d, J=7.7 Hz, 1H), 8.73 (s, 1H), 4.39 (q, J=7.1 Hz, 2H), 3.65-3.50 (m, 1H), 1.45-1.38 (m, 3H), 1.25 (d, J=6.2 Hz, 6H). LCMS m/z 288.2 (M+1).

Intermediate 1B: Ethyl 6-(4-cyano-2-fluorophenyl)-4-(isopropylamino)-5-nitronicotinate

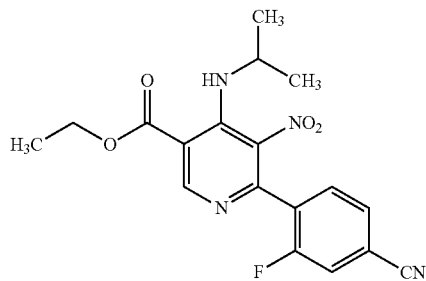

(1B)

A mixture of ethyl 6-chloro-4-(isopropylamino)-5-nitronicotinate (67 mg, 0.23 mmol), (4-cyano-2-fluorophenyl) boronic acid (42.2 mg, 0.26 mmol), sodium carbonate (49.4 mg, 0.47 mmol), and bis(triphenylphosphine)palladium(II) dichloride (16.4 mg, 0.023 mmol) in EtOH (1.5 mL) and toluene (2 mL) was degassed with nitrogen and stirred at 80° C. overnight. The reaction mixture was concentrated, diluted with EtOAc, washed with water, and the organic layer was dried (MgSO$_4$), and concentrated. The crude was purified using ISCO flash chromatography (silica gel/hexanes/ethyl acetate 100:0 to 50:50 gradient) to afford ethyl 6-(4-cyano-2-fluorophenyl)-4-(isopropylamino)-5-nitronicotinate (50.7 mg, 59% yield) as a yellowish brown solid. $^1$H NMR (400 MHz, CHLOROFORM-d) δ 9.03-8.95 (m, 2H), 7.57-7.43 (m, 3H), 4.43 (q, J=7.1 Hz, 2H), 3.54 (dt, J=8.8, 6.3 Hz, 1H), 1.47-1.41 (m, 3H), 1.28-1.22 (m, 6H). LCMS m/z 373.1 (M+1).

Intermediate 1C: Ethyl 5-amino-6-(4-cyano-2-fluorophenyl)-4-(isopropylamino) nicotinate

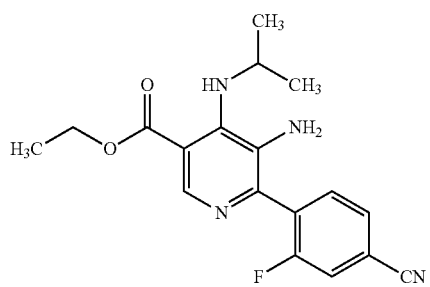

(1C)

A mixture of ethyl 6-(4-cyano-2-fluorophenyl)-4-(isopropylamino)-5-nitronicotinate (50 mg, 0.134 mmol) and iron (30 mg, 0.537 mmol) in acetic acid (4 mL) was stirred at 80° C. for 1 h. The mixture was cooled to room temperature, filtered through a pad of celite and concentrated. The concentrated filtrate was diluted with EtOAc, washed with saturated NaHCO$_3$, water, and the organic layer was dried (MgSO$_4$), and concentrated to afford the crude ethyl 5-amino-6-(4-cyano-2-fluorophenyl)-4-(isopropylamino) nicotinate (40.6 mg, 88% yield) as a brown gum. $^1$H NMR (400 MHz, CHLOROFORM-d) δ 8.65 (s, 1H), 7.75-7.67 (m, 1H), 7.60 (dd, J=7.9, 1.5 Hz, 1H), 7.51 (dd, J=9.2, 1.3 Hz, 1H), 7.05-6.93 (m, 1H), 4.40 (q, J=7.2 Hz, 2H), 4.06-3.88 (m, 1H), 1.42 (t, J=7.1 Hz, 3H), 1.21 (d, J=6.4 Hz, 6H). LCMS m/z 343.2 (M+1).

Intermediate 1D: Ethyl 7-cyano-4-(isopropylamino)-5H-pyrido[3,2-b]indole-3-carboxylate

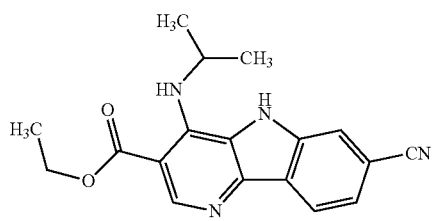

(1D)

A mixture of ethyl 5-amino-6-(4-cyano-2-fluorophenyl)-4-(isopropylamino) nicotinate (40 mg, 0.117 mmol) and potassium carbonate (64.6 mg, 0.467 mmol) in DMA (0.5 mL) was stirred at 140° C. overnight. The mixture was cooled to room temperature and diluted with EtOAc. The organic component was washed with saturated NaHCO$_3$ and water, then the organic layer was dried (MgSO$_4$), and concentrated. The crude product was purified using preparative HPLC (Phen Luna Axia C18 5 μm; 30×100 mm Column; detection at 220 nm; flow rate=40 mL/min; continuous gradient from 20% B to 100% B over 10 min+5 min hold at 100% B, where A=10:90:0.1 MeOH—H$_2$O-TFA and B=90:10:0.1 MeOH—H$_2$O-TFA) to afford ethyl 7-cyano-4-(isopropylamino)-5H-pyrido[3,2-b]indole-3-carboxylate, TFA (9.6 mg, 19% yield) as an off-white solid. $^1$H NMR (400 MHz, DMSO-d$_6$) δ 11.99 (br s, 1H), 8.97 (s, 1H), 8.43 (d, J=8.6 Hz, 1H), 8.19 (s, 1H), 7.70 (d, J=8.3 Hz, 1H), 4.62 (br s, 1H), 4.41 (q, J=7.0 Hz, 2H), 1.49-1.32 (m, 9H). LCMS m/z 323.2 (M+1).

Method 2

Intermediate 1E: Tert-butyl (5-bromo-2-cyanophenyl)carbamate

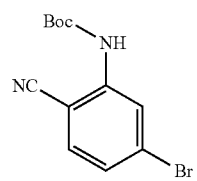

(1E)

A mixture of 2-amino-4-bromobenzonitrile (5 g, 25.4 mmol), di-tert-butyl dicarbonate (6.65 g, 30.5 mmol), DMAP (3.10 g, 25.4 mmol), and triethylamine (3.54 mL, 25.4 mmol) in DCM (100 mL) was stirred at room temperature overnight. Mono and bis-Boc products as well as starting material were observed by LCMS. An additional 0.5 equivalent BOC$_2$O (3 g) was added and stirring was continued for an additional 18 h. The reaction mixture was then washed with water, dried (MgSO$_4$), and concentrated. The crude material was purified using ISCO flash chromatogra-

Intermediate 1F: Tert-butyl N-(5-bromo-2-cyanophenyl)-N-(tert-butoxycarbonyl) glycinate

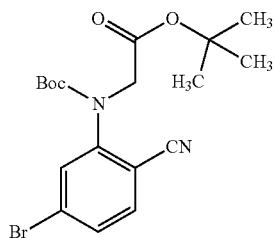
(1F)

To a suspension of 60% NaH (0.727 g, 18.2 mmol in DMF (80 mL) was added a solution of tert-butyl (5-bromo-2-cyanophenyl)carbamate (4.5 g, 15.1 mmol in DMF (20 mL) followed by tert-butyl 2-bromoacetate (2.407 mL, 16.7 mmol). The reaction mixture was stirred at room temperature for 20 min. The reaction was quenched with water. The mixture was extracted with EtOAc, and the organic layer was further washed with saturated NaHCO$_3$ and water. The organic layer was dried (MgSO$_4$), and concentrated and the crude material was purified using ISCO flash chromatography (silica gel/hexanes/ethyl acetate 100:0 to 50:50 gradient) to afford tert-butyl N-(5-bromo-2-cyanophenyl)-N-(tert-butoxycarbonyl) glycinate (6.05 g, 78% yield) as a yellow oil. The product solidified while standing.

Intermediate 1G: Di-tert-butyl 3-amino-6-bromo-1H-indole-1,2-dicarboxylate

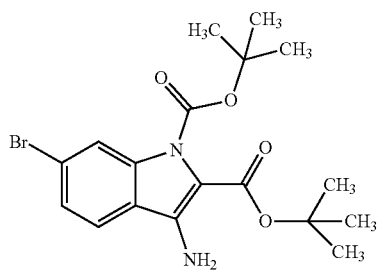
(1G)

To a solution of tert-butyl 2-((5-bromo-2-cyanophenyl)(tert-butoxycarbonyl) amino)acetate (6 g, 14.6 mmol in THF (100 mL) was added potassium tert-butoxide (1.80 g, 16.1 mmol) in two portions. The reaction mixture was stirred at room temperature for 30 min. LCMS showed the reaction was complete. The mixture was poured into water, extracted with EtOAc, dried (MgSO$_4$), and concentrated. The crude was dissolved in DCM and sonicated upon which a white precipitate formed. The solids were collected to afford di-tert-butyl 3-amino-6-bromo-1H-indole-1,2-dicarboxylate (2.06 g, 34% yield) as a white solid. $^1$H NMR (400 MHz, DMSO-d$_6$) δ 7.98 (d, J=1.6 Hz, 1H), 7.88 (d, J=8.4 Hz, 1H), 7.44 (dd, J=8.4, 1.7 Hz, 1H), 6.28-6.23 (m, 2H), 1.54 (d, J=5.6 Hz, 18H).

Intermediate 1H: 6-Bromo-1H-indol-3-amine

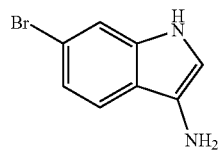
(1H)

A solution of di-tert-butyl 3-amino-6-bromo-1H-indole-1,2-dicarboxylate (2.06 g, 5.0 mmol) and TFA (5 mL, 65 mmol) in DCM (10 mL) was stirred at room temperature for 3 h. The reaction mixture was concentrated, diluted with EtOAc, and washed with saturated NaHCO$_3$ then water. The organic layer was dried (MgSO$_4$), and concentrated to afford 6-bromo-1H-indol-3-amine (1.06 g, 100% yield) as a yellow solid. $^1$H NMR (400 MHz, METHANOL-d$_4$) δ 7.49-7.38 (m, 2H), 7.06 (dd, J=8.4, 1.7 Hz, 1H), 6.80 (s, 1H). LCMS m/z 211 (M+2).

Intermediate 1I: Diethyl 2-(((6-bromo-1H-indol-3-yl)amino)methylene)malonate

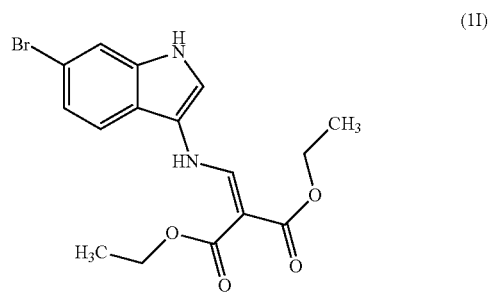 [SMILES: CCOC(=O)C(=CNc1c[nH]c2cc(Br)ccc12)C(=O)OCC]
(1I)

A solution of 6-bromo-1H-indol-3-amine (1 g, 4.74 mmol) and diethyl 2-(ethoxymethylene)malonate (1.025 g, 4.74 mmol) in DMF (20 mL) was stirred at 80° C. for 45 min. The reaction mixture was cooled to room temperature, diluted with EtOAc and washed with water (3×). The organic layer was dried (MgSO$_4$) and concentrated to afford the crude diethyl 2-(((6-bromo-1H-indol-3-yl)amino)methylene)malonate (1.18 g, 65% yield) as a brown solid. LCMS m/z 383 (M+2).

Intermediate 1J: Ethyl 7-bromo-4-oxo-4,5-dihydro-1H-pyrido[3,2-b]indole-3-carboxylate

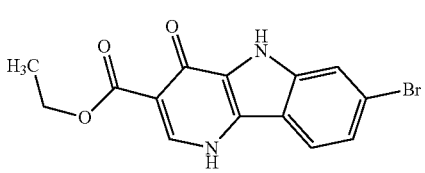
(1J)

Diethyl 2-(((6-bromo-1H-indol-3-yl)amino)methylene) malonate (1.18 g, 3.1 mmol) in diphenyl ether (10 mL) was stirred at 250-255° C. for 15 min and then cooled to room temperature. The mixture was diluted with 1:1 ether/hexanes and stirred for 10 min. The solids were collected by filtration and washed with hexanes to afford ethyl 7-bromo-4-oxo-4,5-dihydro-1H-pyrido[3,2-b]indole-3-carboxylate (1.17 g, 113% yield) as a dark brown solid. LCMS m/z 335 (M+2).

Intermediate 1K: Ethyl 7-cyano-4-oxo-4,5-dihydro-1H-pyrido[3,2-b]indole-3-carboxylate

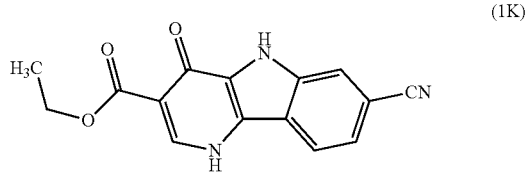 [SMILES: CCOC(=O)c1c[nH]c2c([nH]c3cc(C#N)ccc32)c1=O]

(1K)

A mixture of ethyl 7-bromo-4-oxo-4,5-dihydro-1H-pyrido[3,2-b]indole-3-carboxylate (1.1 g, 3.28 mmol), zinc (0.150 g, 2.3 mmol), zinc cyanide (0.347 g, 2.95 mmol), and Pd$_2$(dba)$_3$ (0.150 g, 0.164 mmol) in DMF (12 mL) was degassed with nitrogen and then tri-tert-butylphosphine (0.088 mL, 0.328 mmol) was added. The reaction mixture was stirred at 120° C. for 2 h then cooled to room temperature. The mixture was filtered through a pad of celite and washed with DMF. The filtrate was diluted with water (80 mL) and the solids were collected by filtration, washed with water followed by ether to afford the crude ethyl 7-cyano-4-oxo-4,5-dihydro-1H-pyrido[3,2-b] indole-3-carboxylate (1.11 g, 84% yield) as a dark brown solid. $^1$H NMR (400 MHz, DMSO-d$_6$) δ 12.42 (s, 1H), 8.54 (s, 1H), 8.28 (d, J=8.3 Hz, 1H), 7.96-7.90 (m, 1H), 7.56 (dd, J=8.4, 1.4 Hz, 1H), 4.26 (q, J=7.1 Hz, 2H), 1.31 (t, J=7.1 Hz, 3H). LCMS m/z 282 (M+1).

Alternate preparation: A suspension of ethyl 7-bromo-4-oxo-4,5-dihydro-1H-pyrido[3,2-b]indole-3-carboxylate (2.35 g, 7.01 mmol) and copper(I) cyanide (0.942 g, 10.52 mmol) in NMP (15 mL) was purged with nitrogen and stirred at 170° C. overnight. The mixture was cooled to room temperature and poured into ice-cold water and stirred for 15 min. The solids were collected by filtration, washed with water and ether to afford the crude ethyl 7-cyano-4-oxo-4,5-dihydro-1H-pyrido[3,2-b]indole-3-carboxylate (1.8 g, 5.12 mmol, 73% yield) as a brown solid. LCMS m/z 282 (M+1).

Intermediate 1L: ethyl 4-chloro-7-cyano-5H-pyrido[3,2-b]indole-3-carboxylate

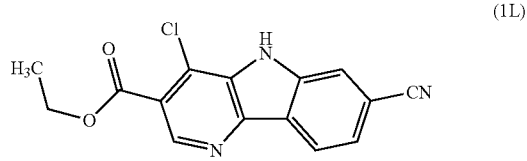 [SMILES: CCOC(=O)c1cnc2c([nH]c3cc(C#N)ccc32)c1Cl]

(1L)

A suspension of ethyl 7-cyano-4-oxo-4,5-dihydro-1H-pyrido[3,2-b]indole carboxylate (1.11 g, 3.95 mmol), N,N-dimethylaniline (0.335 g, 2.76 mmol), and POCl$_3$ (0.368 mL, 3.95 mmol) was heated at 70° C. overnight. The reaction was completion concentrated, POCl$_3$ (0.368 mL, 3.95 mmol) was added and the reaction mixture was heated at 90° C. for 5 h. After cooling, the mixture was concentrated, diluted with EtOAc, and washed with saturated NaHCO$_3$ then water. The organic layer was dried (MgSO$_4$), and concentrated. The crude was purified using ISCO flash chromatography (silica gel/hexanes/ethyl acetate 100:0 to 0:100 gradient) to afford ethyl 4-chloro-7-cyano-5H-pyrido[3,2-b]indole-3-carboxylate (0.386 g, 33% yield) as a light brown solid. $^1$H NMR (400 MHz, DMSO-d$_6$) δ 12.68 (s, 1H), 8.95 (s, 1H), 8.43 (d, J=8.2 Hz, 1H), 8.12-8.08 (m, 1H), 7.71 (dd, J=8.2, 1.3 Hz, 1H), 4.43 (q, J=7.1 Hz, 2H), 1.39 (t, J=7.1 Hz, 3H). LCMS m/z 300 (M+1).

Intermediate 1M: Ethyl 7-cyano-4-(isopropylamino)-5H-pyrido[3,2-b]indole-3-carboxylate

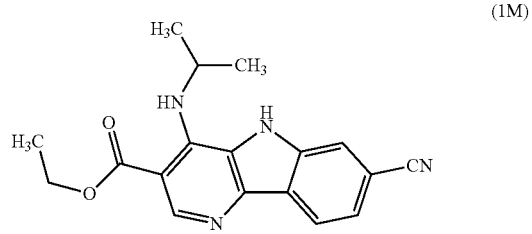 [SMILES: CCOC(=O)c1cnc2c([nH]c3cc(C#N)ccc32)c1NC(C)C]

(1M)

A solution of ethyl 4-chloro-7-cyano-5H-pyrido[3,2-b]indole-3-carboxylate (0.230 g, 0.77 mmol), propan-2-amine (0.136 g, 2.3 mmol), and triethylamine (0.535 mL, 3.84 mmol) in DMA (3 mL) was stirred at 100° C. for 6 h. The mixture was then cooled to room temperature, diluted with EtOAc then washed with water and saturated NaHCO$_3$. The organic layer was dried (MgSO$_4$) and concentrated to afford the crude ethyl 7-cyano-4-(isopropylamino)-5H-pyrido[3,2-b]indole-3-carboxylate (0.244 g, 99% yield) as a brown solid. $^1$H NMR (400 MHz, DMSO-d$_6$) δ 11.47 (s, 1H), 8.84 (s, 1H), 8.61 (br d, J=8.9 Hz, 1H), 8.27 (d, J=8.6 Hz, 1H), 8.06 (dd, J=1.3, 0.7 Hz, 1H), 7.57 (dd, J=8.2, 1.3 Hz, 1H), 4.60-4.44 (m, 1H), 4.35 (q, J=7.2 Hz, 2H), 1.41-1.28 (m, 9H). LCMS m/z 323.2 (M+1).

Intermediate 1N: 7-Cyano-4-(isopropylamino)-5H-pyrido[3,2-b]indole-3-carboxylic acid

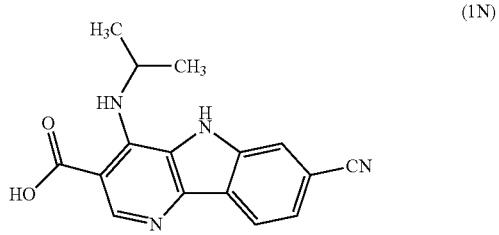 [SMILES: CC(C)Nc1c(C(=O)O)cnc2c1[nH]c1cc(C#N)ccc12]

(1N)

A solution of ethyl 7-cyano-4-(isopropylamino)-5H-pyrido[3,2-b]indole-3-carboxylate (92 mg, 0.29 mmol) and 1N NaOH (0.86 mL, 0.86 mmol) in dioxane (2 mL) was stirred at 80° C. overnight. The mixture was cooled to room temperature and acidified to pH ~6. The mixture was filtered and concentrated to afford the crude product as brown solid contaminated with 1 equivalent of sodium chloride. LCMS m/z 295.1 (M+1).

Example 1

A solution of 7-cyano-4-(isopropylamino)-5H-pyrido[3,2-b]indole-3-carboxylic acid (6 mg, 0.020 mmol) (from Method 1), BOP (9.0 mg, 0.02 mmol), (R)-4-amino-3-fluoro-2-methylbutan-2-ol (2.47 mg, 0.02 mmol), and triethylamine (0.014 mL, 0.102 mmol) in DMF (0.5 mL) was stirred at room temperature for 1 h. The crude was purified directly using preparative HPLC (Phen Luna Axia C18 5 µm; 21.2×100 mm Column; detection at 220 nm; flow rate=40 mL/min; continuous gradient from 20% B to 100% B over 10 min+5 min hold at 100% B, where A=10:90:0.1 MeOH—H$_2$O-TFA and B=90:10:0.1 MeOH—H$_2$O-TFA) to afford (R)-7-cyano-N-(2-fluoro-3-hydroxy-3-methylbutyl)-4-(isopropylamino)-5H-pyrido[3,2-b]indole-3-carboxamide, TFA (1.9 mg, 18% yield) as an off-white solid. $^1$H NMR (400 MHz, CHLOROFORM-d) δ 11.36 (br. s., 1H), 10.21 (br. s., 1H), 8.45 (s, 1H), 8.14 (d, J=8.3 Hz, 2H), 7.87 (s, 1H), 7.39-7.34 (m, 1H), 4.70-4.52 (m, 1H), 4.43-4.31 (m, 1H), 4.12-3.95 (m, 1H), 3.78-3.62 (m, 1H), 1.48 (dd, J=10.9, 6.2 Hz, 6H), 1.44-1.37 (m, 6H). LCMS m/z 398.2 (M+1).

TABLE 2

| Ex. No. | Structure | HPLC RT (min) | HPLC cond. | LCMS | Method |
|---|---|---|---|---|---|
| 2 | 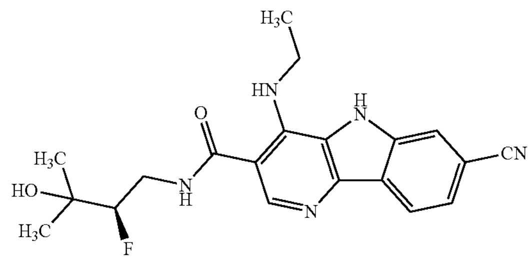 [SMILES: CCNc1c(C(=O)NC[C@@H](F)C(C)(C)O)cnc2c1[nH]c1cc(C#N)ccc12] | 0.63 | C | 384.2 | 1 |
| 3 | 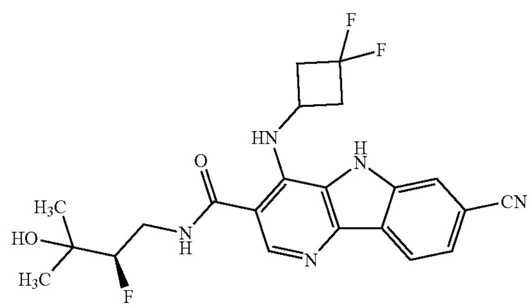 [SMILES: CC(C)(O)[C@H](F)CNC(=O)c1cnc2c([nH]c3cc(C#N)ccc32)c1NC1CC(F)(F)C1] | 1.25 | B | 446.2 | 2 |
| 4 | 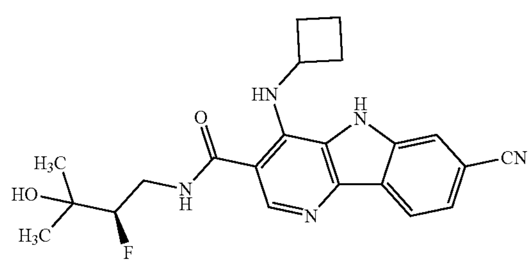 [SMILES: CC(C)(O)[C@H](F)CNC(=O)c1cnc2c([nH]c3cc(C#N)ccc32)c1NC1CCC1] | 1.63 | A | 409.9 | 2 |
| 5 | 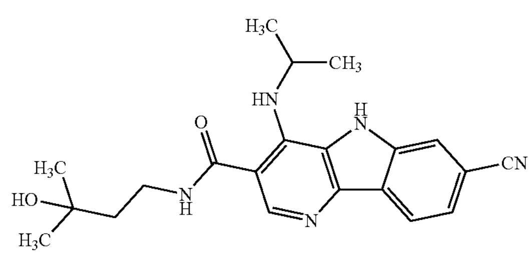 [SMILES: CC(C)Nc1c(C(=O)NCCC(C)(C)O)cnc2c1[nH]c1cc(C#N)ccc12] | 1.5 | A | 379.9 | 2 |
| 6 | 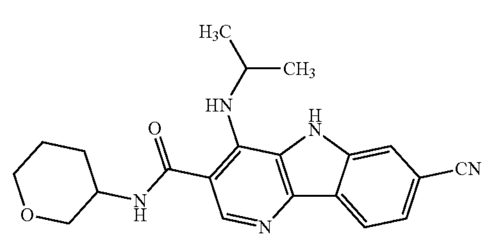 [SMILES: CC(C)Nc1c(C(=O)NC2CCCOC2)cnc2c1[nH]c1cc(C#N)ccc12] | 1.22 | B | 378.2 | 2 |

TABLE 2-continued

| Ex. No. | Structure | HPLC RT (min) | HPLC cond. | LCMS | Method |
|---|---|---|---|---|---|
| 7 | 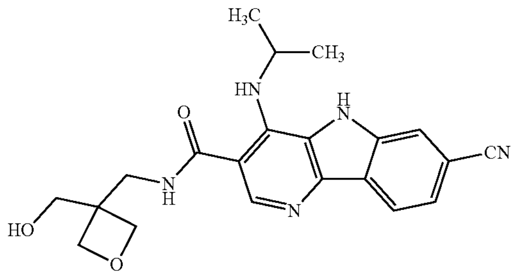 [SMILES: CC(C)Nc1c(C(=O)NCC2(CO)COC2)cnc2c1[nH]c1cc(C#N)ccc12] | 0.97 | B | 394.0 | 2 |
| 8 | 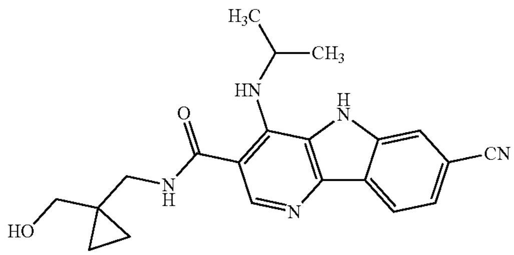 [SMILES: CC(C)Nc1c(C(=O)NCC2(CO)CC2)cnc2c1[nH]c1cc(C#N)ccc12] | 1.27 | B | 377.9 | 2 |
| 9 | 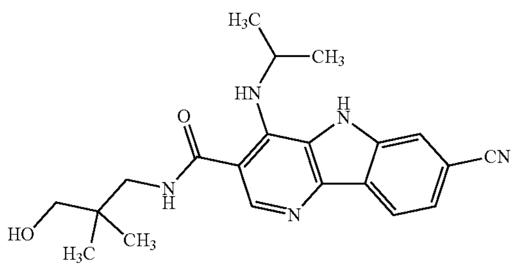 [SMILES: CC(C)Nc1c(C(=O)NCC(C)(C)CO)cnc2c1[nH]c1cc(C#N)ccc12] | 1.34 | B | 380.0 | 2 |
| 10 | 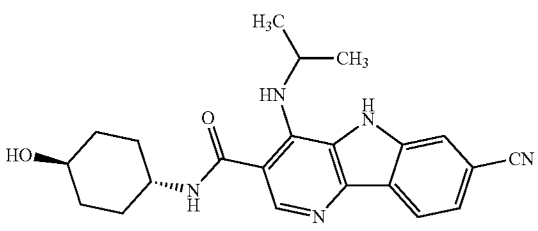 [SMILES: CC(C)Nc1c(C(=O)N[C@H]2CC[C@H](O)CC2)cnc2c1[nH]c1cc(C#N)ccc12] | 1.43 | A | 392.0 | 2 |
| 11 | 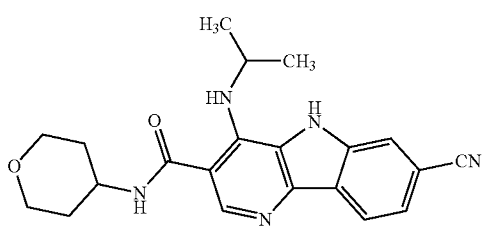 [SMILES: CC(C)Nc1c(C(=O)NC2CCOCC2)cnc2c1[nH]c1cc(C#N)ccc12] | 1.22 | B | 378.2 | 2 |
| 12 | 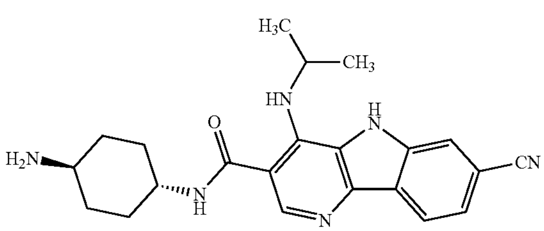 [SMILES: CC(C)Nc1c(C(=O)N[C@H]2CC[C@H](N)CC2)cnc2c1[nH]c1cc(C#N)ccc12] | 0.99 | A | 391.4 | 2 |

TABLE 2-continued

| Ex. No. | Structure | HPLC RT (min) | HPLC cond. | LCMS | Method |
|---|---|---|---|---|---|
| 13 | 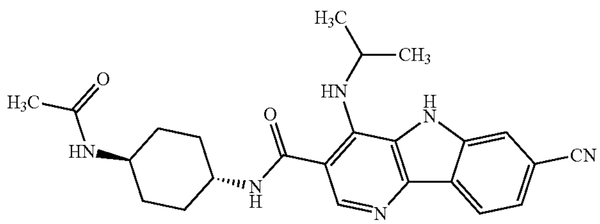 [SMILES: CC(=O)N[C@H]1CC[C@H](NC(=O)c2cnc3c([nH]c4cc(C#N)ccc43)c2NC(C)C)CC1] | 1.38 | A | 432.9 | 2 |
| 14 | 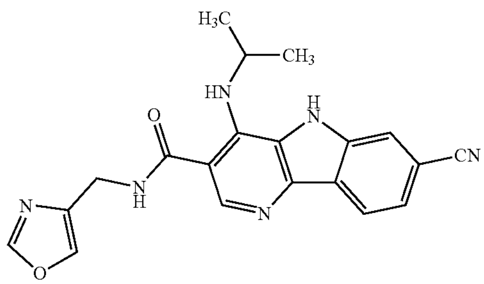 [SMILES: CC(C)Nc1c(C(=O)NCc2cocn2)cnc2c1[nH]c1cc(C#N)ccc12] | 1.41 | A | 375.1 | 2 |
| 15 | 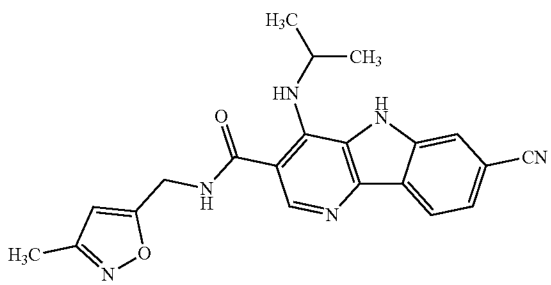 [SMILES: Cc1cc(CNC(=O)c2cnc3c([nH]c4cc(C#N)ccc43)c2NC(C)C)on1] | 1.37 | B | 389.2 | 2 |
| 16 | 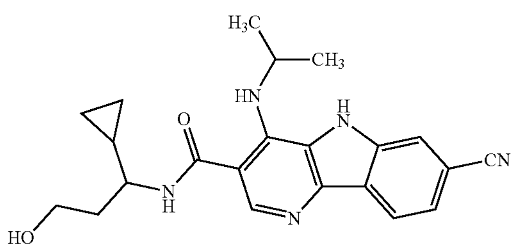 [SMILES: CC(C)Nc1c(C(=O)NC(CCO)C2CC2)cnc2c1[nH]c1cc(C#N)ccc12] | 1.15 | B | 392.2 | 2 |
| 17 | 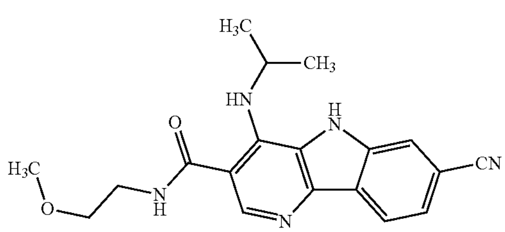 [SMILES: COCCNC(=O)c1cnc2c([nH]c3cc(C#N)ccc32)c1NC(C)C] | 1.08 | B | 351.8 | 2 |
| 18 | 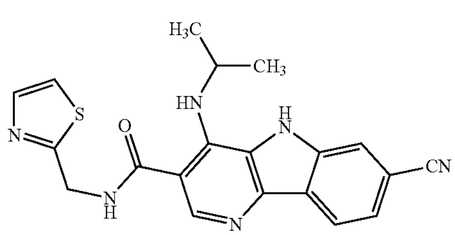 [SMILES: CC(C)Nc1c(C(=O)NCc2nccs2)cnc2c1[nH]c1cc(C#N)ccc12] | 1.14 | B | 391.2 | 2 |

TABLE 2-continued

| Ex. No. | Structure | HPLC RT (min) | HPLC cond. | LCMS | Method |
|---|---|---|---|---|---|
| 19 | 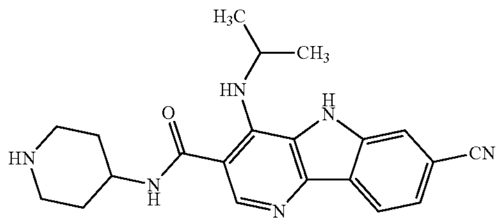 [SMILES: CC(C)Nc1c(C(=O)NC2CCNCC2)cnc2c1[nH]c1cc(C#N)ccc12] | 0.82 | B | 377.2 | 2 |
| 20 | 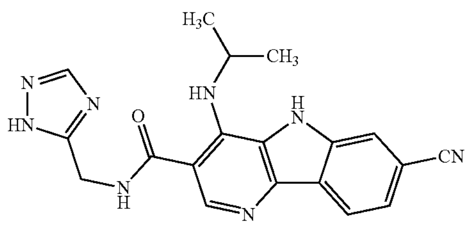 [SMILES: CC(C)Nc1c(C(=O)NCc2ncn[nH]2)cnc2c1[nH]c1cc(C#N)ccc12] | 1.07 | B | 375.1 | 2 |
| 21 | 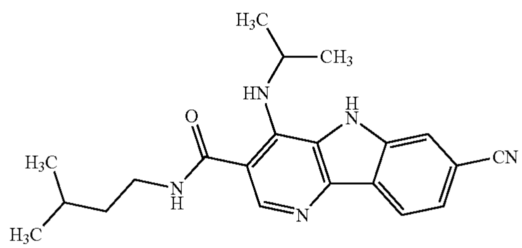 | 1.92 | A | 364.0 | 2 |
| 22 | 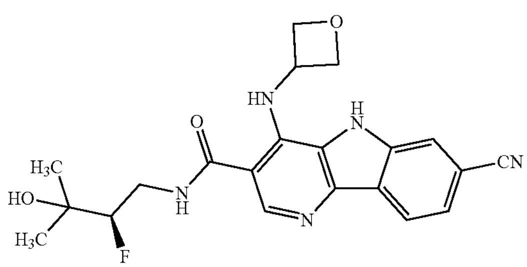 [SMILES: CC(C)(O)[C@H](F)CNC(=O)c1cnc2c([nH]c3cc(C#N)ccc32)c1NC1COC1] | 1.11 | B | 412.2 | 2 |
| 23 | 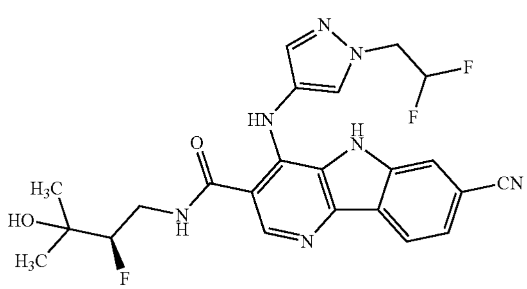 [SMILES: CC(C)(O)[C@H](F)CNC(=O)c1cnc2c([nH]c3cc(C#N)ccc32)c1Nc1cnn(CC(F)F)c1] | 1.28 | A | 486.2 | 2 |
| 24 | 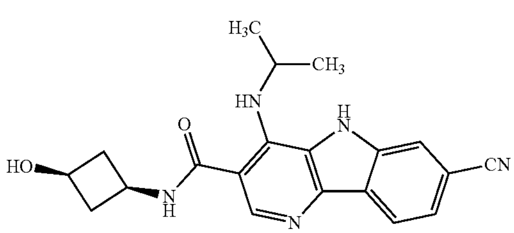 [SMILES: CC(C)Nc1c(C(=O)N[C@H]2C[C@@H](O)C2)cnc2c1[nH]c1cc(C#N)ccc12] | 1.02 | B | 364.2 | 2 |

TABLE 2-continued

| Ex. No. | Structure | HPLC RT (min) | HPLC cond. | LCMS | Method |
|---|---|---|---|---|---|
| 25 | 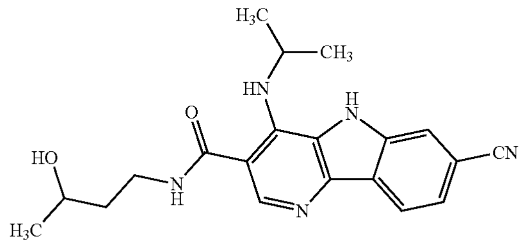 [SMILES: CC(O)CCNC(=O)c1cnc2c([nH]c3cc(C#N)ccc32)c1NC(C)C] | 1.05 | B | 366.3 | 2 |
| 26 | 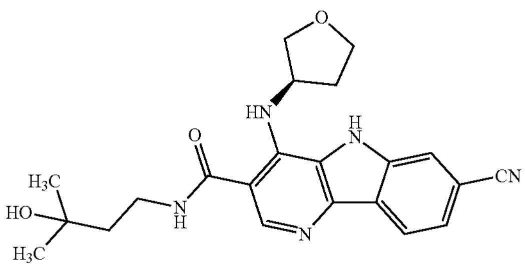 [SMILES: CC(C)(O)CCNC(=O)c1cnc2c([nH]c3cc(C#N)ccc32)c1N[C@@H]1CCOC1] | 1.15 | A | 407.8 | 2 |
| 27 | 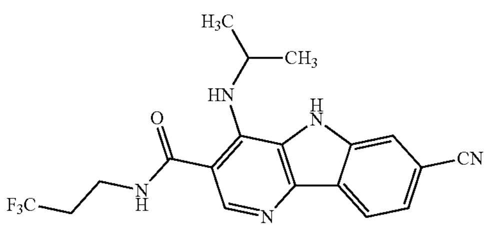 [SMILES: CC(C)Nc1c(C(=O)NCCC(F)(F)F)cnc2c1[nH]c1cc(C#N)ccc12] | 1.32 | B | 390.1 | 2 |
| 28 | 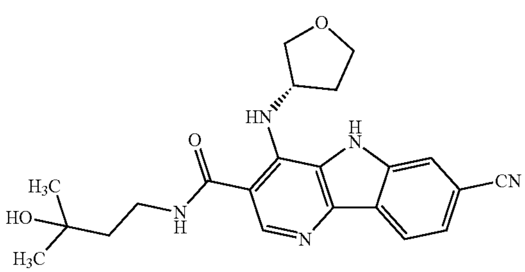 [SMILES: CC(C)(O)CCNC(=O)c1cnc2c([nH]c3cc(C#N)ccc32)c1N[C@H]1CCOC1] | 1.19 | A | 408.2 | 2 |
| 29 | 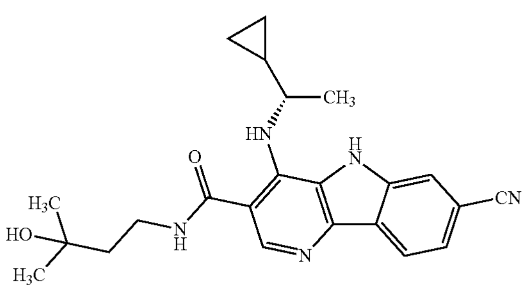 [SMILES: C[C@H](Nc1c(C(=O)NCCC(C)(C)O)cnc2c1[nH]c1cc(C#N)ccc12)C1CC1] | 1.53 | A | 406.2 | 2 |
| 30 | 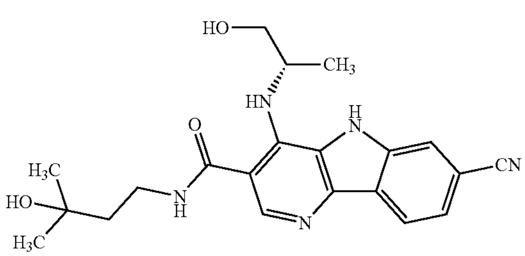 [SMILES: C[C@@H](CO)Nc1c(C(=O)NCCC(C)(C)O)cnc2c1[nH]c1cc(C#N)ccc12] | 0.9 | B | 396.1 | 2 |

TABLE 2-continued

| Ex. No. | Structure | HPLC RT (min) | HPLC cond. | LCMS | Method |
|---|---|---|---|---|---|
| 31 | 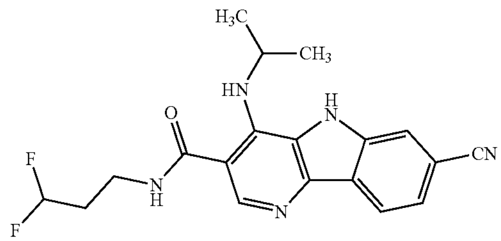 [SMILES: CC(C)Nc1c(C(=O)NCCC(F)F)cnc2c1[nH]c1cc(C#N)ccc12] | 1.57 | A | 372.1 | 2 |
| 32 | 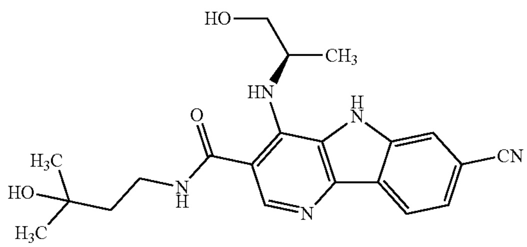 [SMILES: C[C@H](CO)Nc1c(C(=O)NCCC(C)(C)O)cnc2c1[nH]c1cc(C#N)ccc12] | 0.9 | B | 396.0 | 2 |
| 33 | 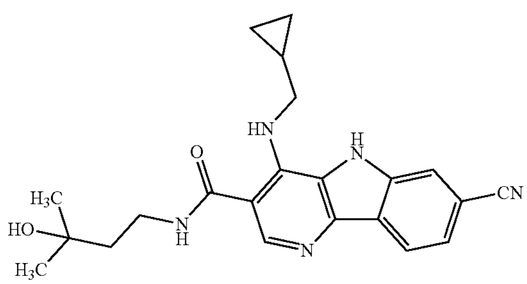 [SMILES: CC(C)(O)CCNC(=O)c1cnc2c([nH]c3cc(C#N)ccc32)c1NCC1CC1] | 1.45 | A | 392.0 | 2 |
| 34 | 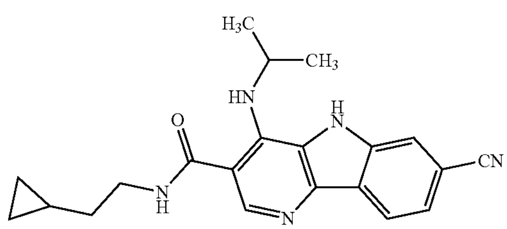 [SMILES: CC(C)Nc1c(C(=O)NCCC2CC2)cnc2c1[nH]c1cc(C#N)ccc12] | 1.75 | A | 362.2 | 2 |
| 35 | 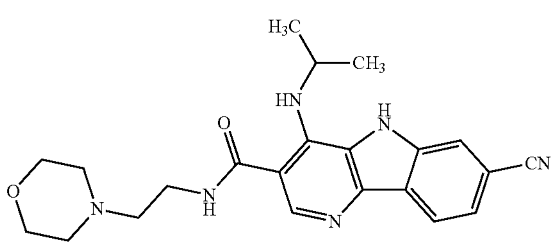 [SMILES: CC(C)Nc1c(C(=O)NCCN2CCOCC2)cnc2c1[nH]c1cc(C#N)ccc12] | 0.82 | B | 407.3 | 2 |
| 36 | 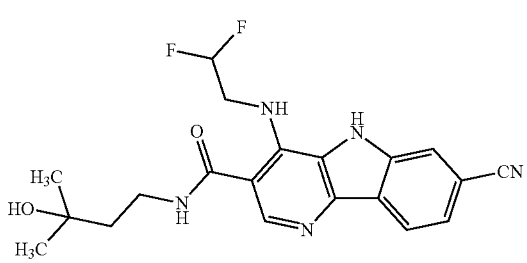 [SMILES: CC(C)(O)CCNC(=O)c1cnc2c([nH]c3cc(C#N)ccc32)c1NCC(F)F] | 1.27 | A | 402.1 | 2 |

TABLE 2-continued

| Ex. No. | Structure | HPLC RT (min) | HPLC cond. | LCMS | Method |
|---|---|---|---|---|---|
| 37 | 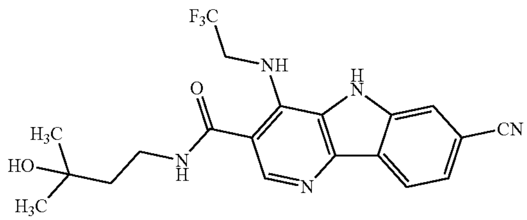 [SMILES: CC(C)(O)CCNC(=O)c1cnc2c([nH]c3cc(C#N)ccc32)c1NCC(F)(F)F] | 0.68 | C | 420.2 | 2 |
| 38 | 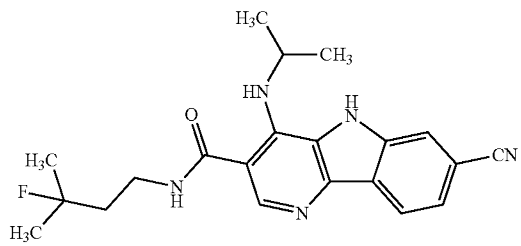 [SMILES: CC(C)Nc1c(C(=O)NCCC(C)(C)F)cnc2c1[nH]c1cc(C#N)ccc12] | 0.78 | C | 382.2 | 2 |
| 39 | 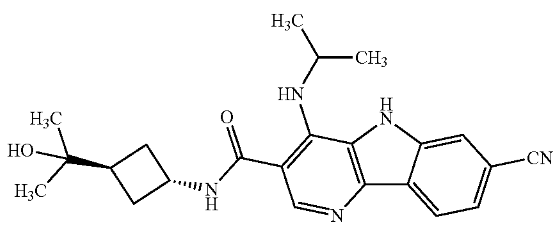 [SMILES: CC(C)Nc1c(C(=O)N[C@H]2C[C@H](C(C)(C)O)C2)cnc2c1[nH]c1cc(C#N)ccc12] | 1.18 | B | 406.1 | 2 |
| 40 | 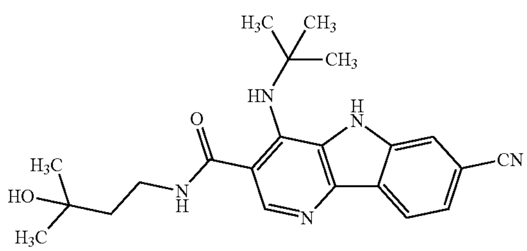 [SMILES: CC(C)(O)CCNC(=O)c1cnc2c([nH]c3cc(C#N)ccc32)c1NC(C)(C)C] | 1.4 | A | 393.8 | 2 |
| 41 | 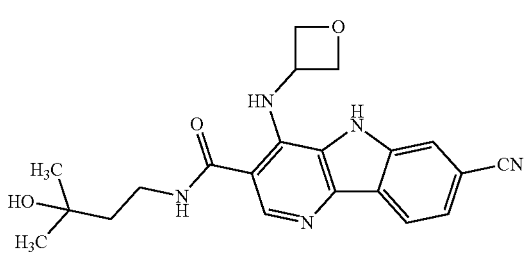 [SMILES: CC(C)(O)CCNC(=O)c1cnc2c([nH]c3cc(C#N)ccc32)c1NC1COC1] | 1.05 | A | 394.0 | 2 |
| 42 | 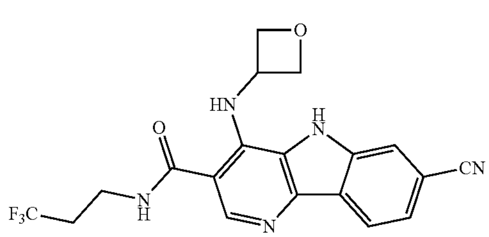 [SMILES: N#Cc1ccc2c(c1)[nH]c1c(NC3COC3)c(C(=O)NCCC(F)(F)F)cnc12] | 1.3 | A | 404.2 | 2 |

TABLE 2-continued

| Ex. No. | Structure | HPLC RT (min) | HPLC cond. | LCMS | Method |
|---|---|---|---|---|---|
| 43 | 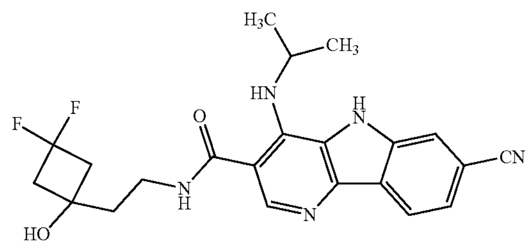 [SMILES: CC(C)Nc1c(C(=O)NCCC2(O)CC(F)(F)C2)cnc2c1[nH]c1cc(C#N)ccc12] | 1.51 | A | 428.1 | 2 |
| 44 | 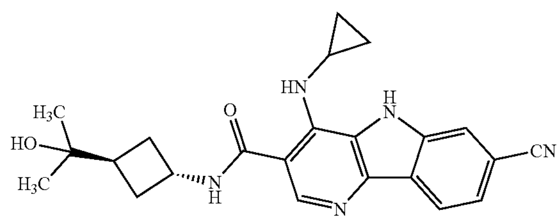 [SMILES: CC(C)(O)[C@H]1C[C@H](NC(=O)c2cnc3c([nH]c4cc(C#N)ccc43)c2NC2CC2)C1] | 1.15 | B | 404.1 | 2 |
| 45 | 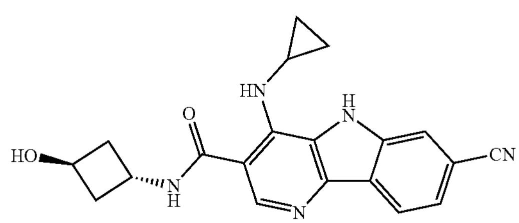 [SMILES: N#Cc1ccc2c(c1)[nH]c1c(NC3CC3)c(C(=O)N[C@H]3C[C@H](O)C3)cnc12] | 1.19 | A | 362.2 | 2 |
| 46 | 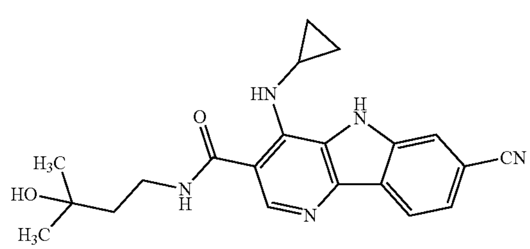 [SMILES: CC(C)(O)CCNC(=O)c1cnc2c([nH]c3cc(C#N)ccc32)c1NC1CC1] | 1.22 | B | 378.2 | 2 |
| 47 | 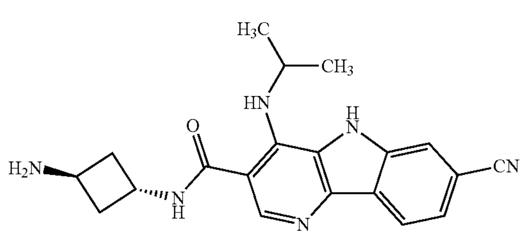 [SMILES: CC(C)Nc1c(C(=O)N[C@H]2C[C@H](N)C2)cnc2c1[nH]c1cc(C#N)ccc12] | 1.02 | A | 363.2 | 2 |
| 48 | 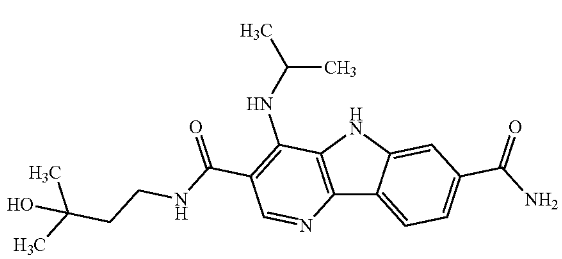 [SMILES: CC(C)Nc1c(C(=O)NCCC(C)(C)O)cnc2c1[nH]c1cc(C(N)=O)ccc12] | 1.1 | A | 397.9 | 2 |

TABLE 2-continued
| Ex. No. | Structure | HPLC RT (min) | HPLC cond. | LCMS | Method |
|---|---|---|---|---|---|
| 49 | 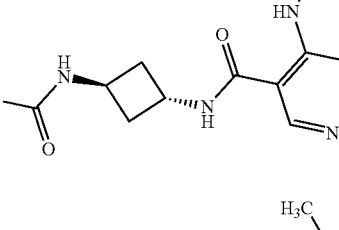 | 1.28 | A | 404.9 | 2 |
| 50 | 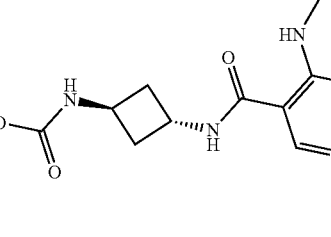 | 1.43 | A | 421.0 | 2 |
| 51 | 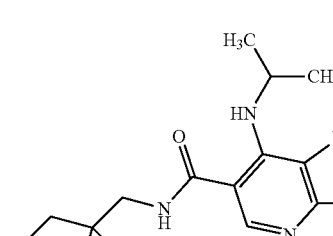 | 0.79 | B | 387.1 | 2 |
| 52 | 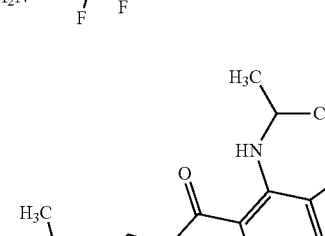 | 1.16 | A | 379.2 | 2 |
| 53 | 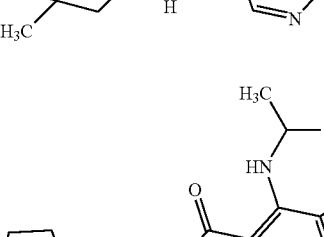 | 1.13 | A | 377.3 | 2 |
| 54 | 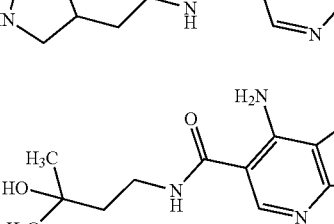 | 1.01 | B | 338.1 | 2 |

TABLE 2-continued

| Ex. No. | Structure | HPLC RT (min) | HPLC cond. | LCMS | Method |
|---|---|---|---|---|---|
| 55 | 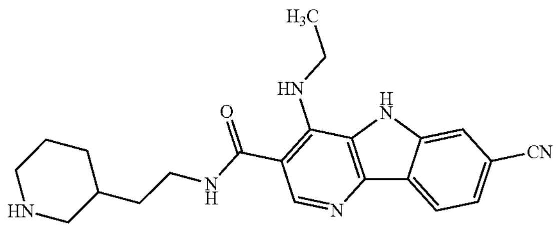 [SMILES: CCNc1c(C(=O)NCCC2CCCNC2)cnc2c1[nH]c1cc(C#N)ccc12] | 1.3 | A | 391.0 | 2 |
| 56 | 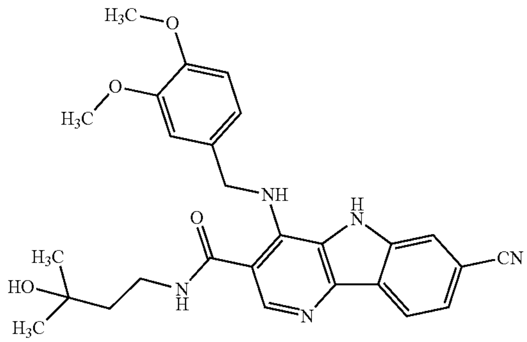 [SMILES: COc1ccc(CNc2c(C(=O)NCCC(C)(C)O)cnc3c2[nH]c2cc(C#N)ccc23)cc1OC] | 1.49 | A | 488.0 | 2 |
| 57 | 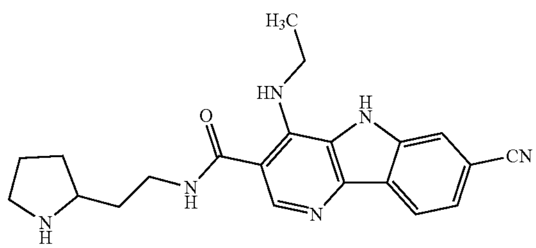 [SMILES: CCNc1c(C(=O)NCCC2CCCN2)cnc2c1[nH]c1cc(C#N)ccc12] | 1.09 | A | 377.2 | 2 |
| 58 | 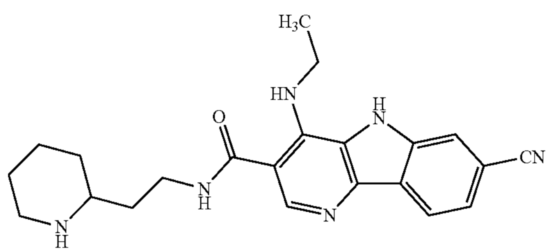 [SMILES: CCNc1c(C(=O)NCCC2CCCCN2)cnc2c1[nH]c1cc(C#N)ccc12] | 0.99 | B | 391.2 | 2 |
| 59 | 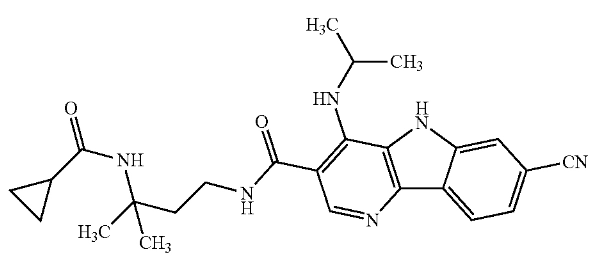 [SMILES: CC(C)Nc1c(C(=O)NCCC(C)(C)NC(=O)C2CC2)cnc2c1[nH]c1cc(C#N)ccc12] | 1.51 | A | 447.2 | 2 |
| 60 | 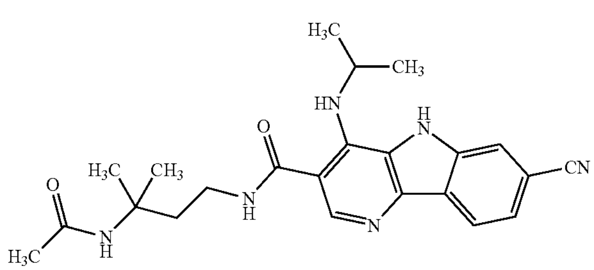 [SMILES: CC(=O)NC(C)(C)CCNC(=O)c1cnc2c([nH]c3cc(C#N)ccc32)c1NC(C)C] | 1.18 | B | 421.0 | 2 |

TABLE 2-continued

| Ex. No. | Structure | HPLC RT (min) | HPLC cond. | LCMS | Method |
|---|---|---|---|---|---|
| 61 | 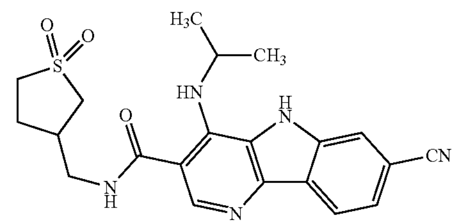 [SMILES: CC(C)Nc1c(C(=O)NCC2CCS(=O)(=O)C2)cnc2c1[nH]c1cc(C#N)ccc12] | 1.31 | A | 426.2 | 2 |
| 62 | 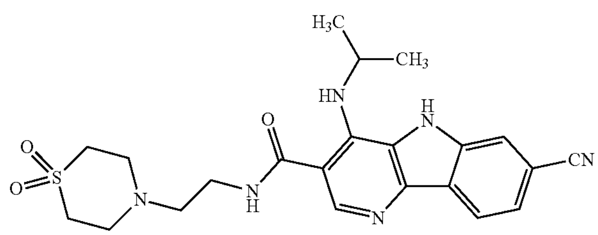 [SMILES: CC(C)Nc1c(C(=O)NCCN2CCS(=O)(=O)CC2)cnc2c1[nH]c1cc(C#N)ccc12] | 1.24 | A | 455.0 | 2 |
| 63 | 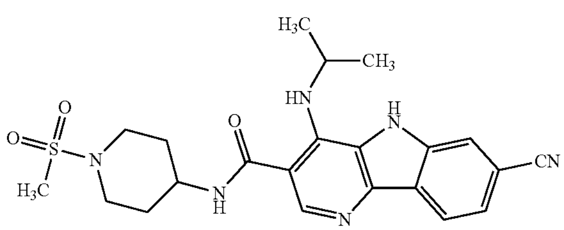 [SMILES: CC(C)Nc1c(C(=O)NC2CCN(S(C)(=O)=O)CC2)cnc2c1[nH]c1cc(C#N)ccc12] | 1.4 | A | 455.3 | 2 |
| 64 | 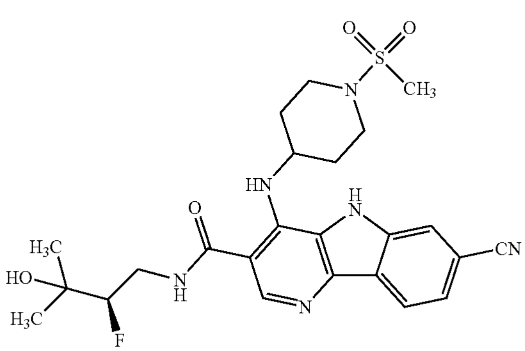 [SMILES: CC(C)(O)[C@H](F)CNC(=O)c1cnc2c([nH]c3cc(C#N)ccc32)c1NC1CCN(S(C)(=O)=O)CC1] | 1.21 | A | 517.4 | 2 |
| 65 | 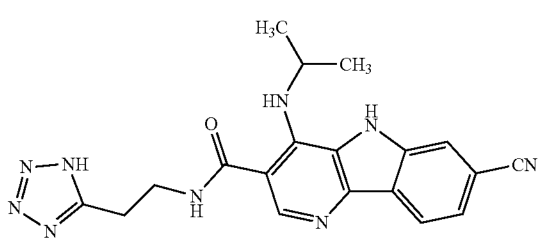 [SMILES: CC(C)Nc1c(C(=O)NCCc2nnn[nH]2)cnc2c1[nH]c1cc(C#N)ccc12] | 0.95 | A | 390.0 | 2 |

Example 66

(R)—N-(2-fluoro-3-hydroxy-3-methylbutyl)-4-(isopropylamino)-7-(thiazol-5-yl)-5H-pyrido[3,2-b]indole-3-carboxamide

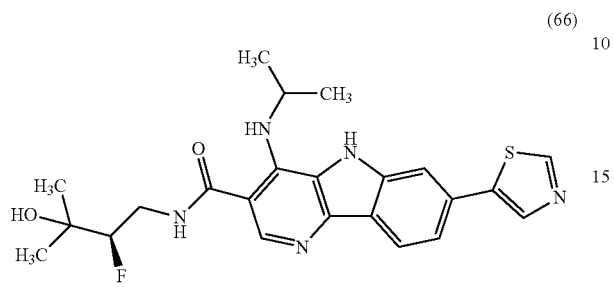

(66)

Intermediate 66A: ethyl 7-bromo-4-chloro-5H-pyrido[3,2-b]indole-3-carboxylate

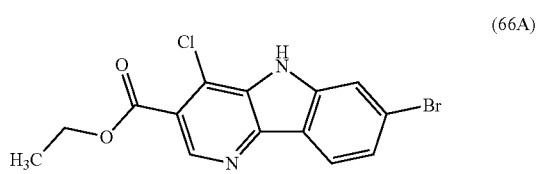 [SMILES: CCOC(=O)c1cnc2c([nH]c3cc(Br)ccc32)c1Cl]

(66A)

A suspension of ethyl 7-bromo-4-oxo-4,5-dihydro-1H-pyrido[3,2-b]indole carboxylate (1.7 g, 5.07 mmol) and POCl₃ (5 mL, 53.6 mmol) in toluene (15 mL) was stirred at 110° C. for 10 h. The reaction mixture was cooled to room temperature and concentrated. The mixture was diluted with EtOAc, washed with 1.5 M potassium phosphate, dried (MgSO₄), and concentrated. The crude product was purified using ISCO flash chromatography (silica gel/hexanes/ethyl acetate with 10% ammonium hydroxide 100:0 to 0:100 gradient) to afford ethyl 7-bromo-4-chloro-5H-pyrido[3,2-b]indole-3-carboxylate (1.11 g, 62% yield) as a dark brown solid. LCMS m/z 355.0 (M+2).

Intermediate 66B: Ethyl 7-bromo-4-(isopropylamino)-5H-pyrido[3,2-b]indole-3-carboxylate

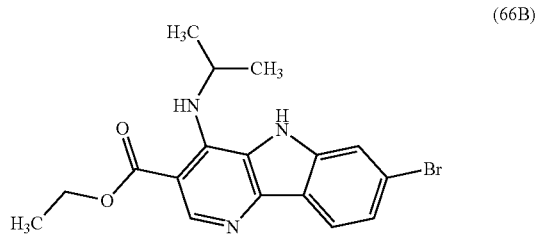 [SMILES: CCOC(=O)c1cnc2c([nH]c3cc(Br)ccc32)c1NC(C)C]

(66B)

A solution of ethyl 7-bromo-4-chloro-5H-pyrido[3,2-b]indole-3-carboxylate (0.4 g, 1.13 mmol), propan-2-amine (0.134 g, 2.26 mmol), and triethylamine (0.47 mL, 3.4 mmol) in DMA (4 mL) was stirred at 110° C. overnight. The mixture was cooled to room temperature, diluted with EtOAc, and washed with saturated NH₄Cl and water. The organic layer was dried (MgSO₄), and concentrated to afford the crude ethyl 7-bromo-4-(isopropylamino)-5H-pyrido[3,2-b]indole-3-carboxylate (0.412 g, 97% yield) as a brown solid. LCMS m/z 378.0 (M+2).

Intermediate 66C: Ethyl 4-(isopropylamino)-7-(thiazol-5-yl)-5H-pyrido[3,2-b]indole-3-carboxylate, TFA

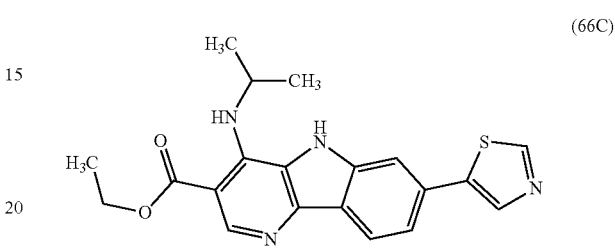

(66C)

A mixture of ethyl 7-bromo-4-(isopropylamino)-5H-pyrido[3,2-b]indole carboxylate (50 mg, 0.133 mmol), sodium carbonate (42.3 mg, 0.4 mmol), bis(triphenylphosphine)palladium(II) dichloride (9.33 mg, 0.013 mmol), and thiazole boronic acid pinacol ester (33.7 mg, 0.16 mmol) in THF (1.5 mL) and water (0.2 mL) was purged with nitrogen and stirred at 70° C. for 3 days. The mixture was diluted with EtOAc, washed with water, dried (MgSO₄), and concentrated. The crude was purified using preparative HPLC (Phen Luna Axia C18 5μ; 30×100 mm Column; detection at 220 nm; flow rate=40 mL/min; continuous gradient from 40% B to 100% B over 10 min+5 min hold at 100% B, where A=10:90:0.1 MeOH—H₂O-TFA and B=90:10:0.1 MeOH—H₂O-TFA) to afford ethyl 4-(isopropylamino)-7-(thiazol-5-yl)-5H-pyrido[3,2-b] indole-3-carboxylate, TFA (11.8 mg, 17.96% yield) as a light brown solid. ¹H NMR (400 MHz, CHLOROFORM-d) δ 11.48 (br s, 1H), 9.66 (d, J=8.2 Hz, 1H), 8.89-8.82 (m, 1H), 8.43 (s, 1H), 8.10 (s, 1H), 7.90 (d, J=8.4 Hz, 1H), 7.52 (s, 1H), 7.22 (dd, J=8.5, 1.4 Hz, 1H), 4.63-4.50 (m, 1H), 4.18 (q, J=7.1 Hz, 2H), 1.50 (d, J=6.2 Hz, 6H), 1.41-1.33 (m, 3H). LCMS m/z 381.1 (M+1).

Intermediate 66D: Ethyl 4-(isopropylamino)-7-(thiazol-5-yl)-5H-pyrido[3,2-b]indole-3-carboxylate, TFA

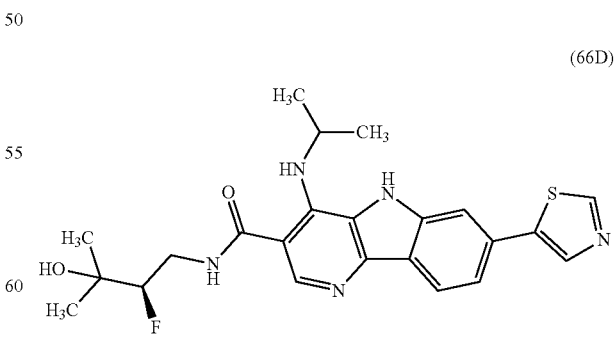

(66D)

A solution of ethyl 4-(isopropylamino)-7-(thiazol-5-yl)-5H-pyrido[3,2-b]indole-3-carboxylate, TFA (11.8 mg, 0.024 mmol) and 1 N NaOH (0.119 mL, 0.119 mmol) in dioxane (1 mL) was stirred at 75° C. overnight. An additional 0.1 mL 1N NaOH was added and heating was continued for 1 h. The mixture was cooled to room temperature and acidified using 1 N HCl and concentrated (contaminated with 1 eq. NaCl). The crude was dissolved in DMF and (R)-4-amino-3-fluoro-2-methylbutan-2-ol (2.89 mg, 0.024 mmol), BOP (10.55 mg, 0.024 mmol), and triethylamine (9.98 μL, 0.072 mmol) were added. The reaction mixture was stirred for 45 min, filtered and concentrated. The filtrate was diluted with EtOAc, washed with water, dried (MgSO$_4$), and concentrated. The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 10-60% B over 20 minutes, then a 5-minute hold at 100% B; Flow: 20 mL/min. Fractions containing the product were combined and dried via centrifugal evaporation to afford (R)—N-(2-fluoro-3-hydroxy-3-methylbutyl) (isopropylamino)-7-(thiazol-5-yl)-5H-pyrido[3,2-b]indole-3-carboxamide (2.0 mg, 18% yield). $^1$H NMR (500 MHz, DMSO-d$_6$) δ 11.12 (br s, 1H), 9.28-9.08 (m, 1H), 8.73 (br s, 1H), 8.46 (br d, J=8.7 Hz, 2H), 8.19 (br d, J=6.6 Hz, 1H), 7.86 (s, 1H), 7.60 (br s, 1H), 4.49-4.30 (m, 2H), 3.83-3.65 (m, 1H), 1.27 (dd, J=5.9, 2.1 Hz, 6H), 1.19 (br d, J=6.5 Hz, 6H). One proton was buried under water peak. LCMS m/z 456.1 (M+1).

TABLE 3

| Ex. No. | Structure | HPLC rt (min) | HPLC cond. | LCMS |
|---|---|---|---|---|
| 67 | 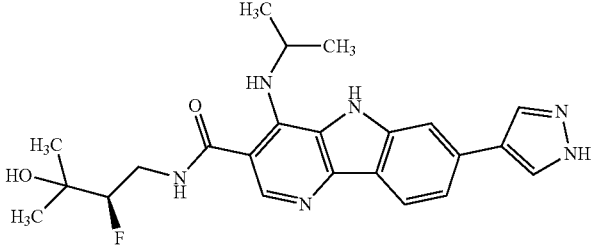 [SMILES: CC(C)Nc1c(C(=O)NC[C@@H](F)C(C)(C)O)cnc2c1[nH]c1cc(-c3cn[nH]c3)ccc12] | 1.34 | A | 439.2 |
| 68 | 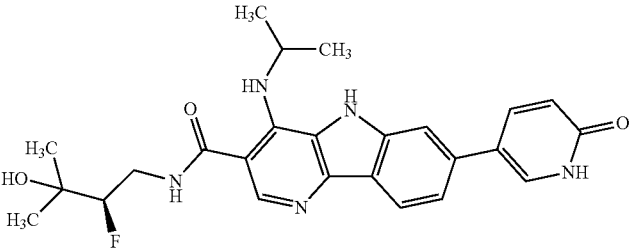 [SMILES: CC(C)Nc1c(C(=O)NC[C@@H](F)C(C)(C)O)cnc2c1[nH]c1cc(-c3ccc(=O)[nH]c3)ccc12] | 1.06 | A | 466.3 |

Example 69

(R)-7-cyano-N-(2-fluoro-3-hydroxy-3-methylbutyl)-4-(isopropylamino)-5H-pyrrolo [3,2-b:4,5-b']dipyridine-3-carboxamide

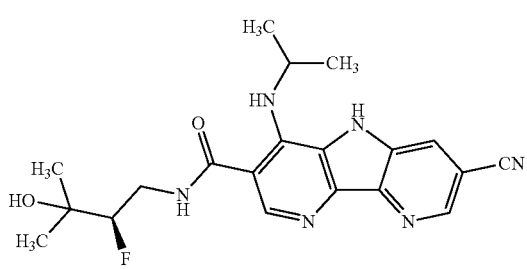
(69)

Intermediate 69A: 6-Bromo-3-nitro-1H-pyrrolo[3,2-b]pyridine

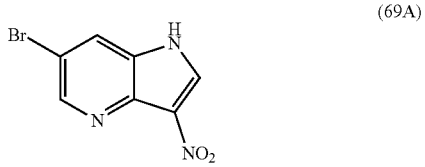 [SMILES: O=[N+]([O-])c1c[nH]c2cc(Br)cnc12]
(69A)

Fuming nitric acid (0.25 mL, 5.58 mmol) was added at 0° C. to a suspension of 6-bromo-1H-pyrrolo[3,2-b]pyridine (1 g, 5.08 mmol) in sulfuric acid (15 mL) at 0° C. The reaction mixture was stirred at 0° C. for 1.5 h. Ice-cold water (20 mL) was added and pH was adjusted to ~pH 7-8 using 5 N NaOH. The solids were collected by filtration and washed with water. The product was azeotroped from MeOH to afford the crude 6-bromo-3-nitro-1H-pyrrolo[3,2-b]pyridine (1.21 g, 99% yield) as an orange-yellow solid. $^1$H NMR (400 MHz, METHANOL-$d_4$) δ 8.48 (s, 1H), 8.34 (d, J=2.0 Hz, 1H), 7.96 (d, J=2.0 Hz, 1H). LCMS m/z 242.0 (M+2).

Intermediate 69B: 6-Bromo-1H-pyrrolo[3,2-b]pyridin-3-amine

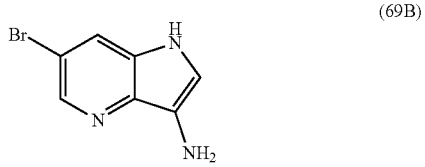
(69B)

A mixture of 6-bromo-3-nitro-1H-pyrrolo[3,2-b]pyridine (1.2 g, 4.96 mmol), zinc (1.62 g, 24.8 mmol), and ammonium chloride (1.33 g, 24.8 mmol) in MeOH (9 mL) and water (1 mL) was heated to reflux for 1 min and then stirred at room temperature for 30 min. The mixture was filtered and concentrated and diluted with EtOAc and filtered again to remove the black insoluble solid. The filtrate was then washed with saturated NaHCO$_3$, and the aqueous layer was extracted with EtOAc (3×). The combined organic layers were dried (MgSO$_4$) and concentrated to afford the crude 6-bromo-1H-pyrrolo[3,2-b]pyridin-3-amine (1.12 g, 100% yield) as a dark brown solid. LCMS m/z 211.9 (M+1).

Intermediate 69C: Diethyl 2-(((6-bromo-1H-pyrrolo[3,2-b]pyridin-3-yl)amino) methylene)malonate

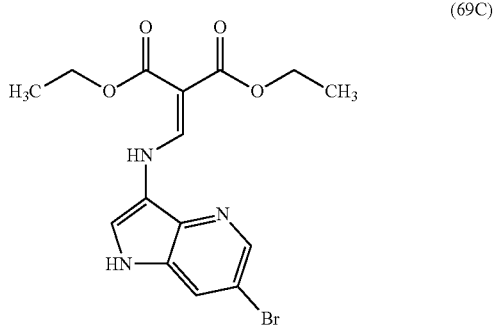 [SMILES: CCOC(=O)C(=CNc1c[nH]c2cc(Br)cnc12)C(=O)OCC]
(69C)

A suspension of 6-bromo-1H-pyrrolo[3,2-b]pyridin-3-amine (1.1 g, 5.2 mmol) and diethyl 2-(ethoxymethylene) malonate (1.12 g, 5.2 mmol) was heated at 120° C. for 1 h. The reaction mixture was cooled to room temperature and diluted with 10% ether/hexanes and stirred overnight. The resulting solids were collected by filtration to afford the crude diethyl 2-(((6-bromo-1H-pyrrolo[3,2-b]pyridin-3-yl)amino)methylene) malonate.

Intermediate 69D: ethyl 7-bromo-4-oxo-4,5-dihydro-1H-pyrrolo[3,2-b:4,5-b']dipyridine-3-carboxylate, TFA (69D)

A mixture of diethyl 2-(((6-bromo-1H-pyrrolo[3,2-b]pyridin-3-yl)amino) methylene)malonate and PPA (0.485 mL) was stirred at 110° C. overnight. The reaction mixture was cooled to room temperature, neutralized using 2 M NaOH and extracted with EtOAc (3×). The organic extracts were dried (MgSO$_4$), and concentrated. The crude material was purified using ISCO flash chromatography (silica gel/hexanes/ethyl acetate/MeOH 100:0 to 0:90:10 gradient). The product was re-purified using preparative HPLC (Phen Luna Axia C18 5 μm; 30×100 mm Column; detection at 220 nm; flow rate=40 mL/min; continuous gradient from 20% B to 100% B over 10 min+5 min hold at 100% B, where A=10:90:0.1 MeOH—H$_2$O-TFA and B=90:10:0.1 MeOH—H$_2$O-TFA) to afford ethyl 7-bromo-4-oxo-4,5-dihydro-1H-pyrrolo[3,2-b:4,5-b']dipyridine carboxylate, TFA (20.5 mg) as a brown solid. $^1$H NMR (400 MHz, DMSO-$d_6$) δ 12.32 (s, 1H), 8.65 (d, J=2.0 Hz, 1H), 8.38 (s, 1H), 8.12 (d, J=2.0 Hz, 1H), 4.25 (d, J=7.1 Hz, 2H), 1.31 (t, J=7.1 Hz, 3H). LCMS m/z 338.0 (M+2).

Intermediate 69E: Ethyl 7-bromo-4-chloro-5H-pyrrolo[3,2-b:4,5-b']dipyridine carboxylate

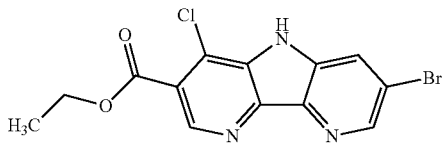

(69E)

A solution of ethyl 7-bromo-4-oxo-4,5-dihydro-1H-pyrrolo[3,2-b:4,5-b'] dipyridine-3-carboxylate (0.103 g, 0.306 mmol) and POCl$_3$ (1.5 mL, 16.1 mmol) was stirred at 90° C. overnight. The mixture was concentrated, diluted with EtOAc, and washed with saturated NaHCO$_3$ and water. The organic layer was dried (MgSO$_4$), and concentrated to afford the crude ethyl 7-bromo-4-chloro-5H-pyrrolo[3,2-b:4,5-b'] dipyridine-3-carboxylate (0.106 g, 98% yield) as a brown solid.

Intermediate 69F: ethyl 7-bromo-4-(isopropylamino)-5H-pyrrolo[3,2-b:4,5-b']dipyridine-3-carboxylate

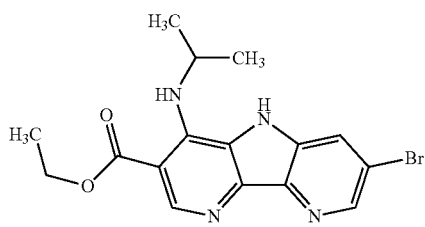

(69F)

A solution of ethyl 7-bromo-4-chloro-5H-pyrrolo[3,2-b: 4,5-b']dipyridine-3-carboxylate (0.1 g, 0.28 mmol), propan-2-amine (0.050 g, 0.85 mmol), and triethylamine (0.2 mL, 1.41 mmol) in DMA (1 mL) was stirred at 120° C. for 4 h. The reaction mixture was cooled to room temperature, diluted with EtOAc, and washed with water and 10% LiCl. The organic layer was dried (MgSO$_4$) and concentrated to afford the crude ethyl 7-bromo-4-(isopropylamino)-5H-pyrrolo[3,2-b:4,5-b']dipyridine-3-carboxylate as a brown solid.

Intermediate 69G: Ethyl 7-cyano-4-(isopropylamino)-5H-pyrrolo[3,2-b:4,5-b']dipyridine-3-carboxylate, TFA

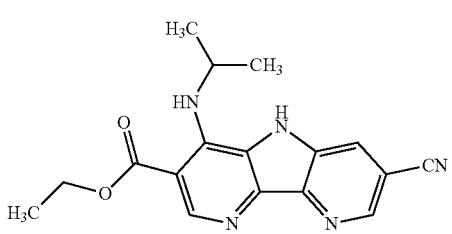

(69G)

A mixture of ethyl 7-bromo-4-(isopropylamino)-5H-pyrrolo[3,2-b:4,5-b'] dipyridine-3-carboxylate (80 mg, 0.212 mmol), zinc cyanide (50 mg, 0.42 mmol), and Pd(Ph$_3$P)$_4$ (24.5 mg, 0.021 mmol) in DMA (1.5 mL) was purged with nitrogen and stirred at 120° C. overnight. The reaction mixture was cooled to room temperature, diluted with EtOAc and washed with saturated NH$_4$Cl and water. The organic layer was dried (MgSO$_4$), and concentrated. The crude was purified using preparative HPLC (Phen Luna Axia C18 5 μm; 30×100 mm Column; detection at 220 nm; flow rate=40 mL/min; continuous gradient from 20% B to 100% B over 10 min+2 min hold at 100% B, where A=10:90:0.1 MeOH—H$_2$O-TFA and B=90:10:0.1 MeOH—H$_2$O-TFA) to afford ethyl 7-cyano-4-(isopropylamino)-5H-pyrrolo[3,2-b: 4,5-b']dipyridine-3-carboxylate, TFA (16.4 mg, 18% yield) as a brown solid. LCMS m/z 324.1 (M+1).

Intermediate 69H: 7-Cyano-4-(isopropylamino)-5H-pyrrolo[3,2-b:4,5-b']dipyridine-3-carboxylic acid

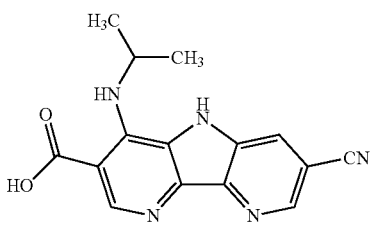

(69H)

A mixture of ethyl 7-cyano-4-(isopropylamino)-5H-pyrrolo[3,2-b:4,5-b'] dipyridine-3-carboxylate, TFA (16.4 mg, 0.037 mmol) and LiOH (0.19 mL, 0.19 mmol) in 1,4-dioxane (1.2 mL) was stirred at 90° C. for 5 h. The reaction mixture was cooled to room temperature and acidified with 1 N HCl and concentrated. The crude was purified using preparative HPLC (Phen Luna Axia C18 5 μm; 30×100 mm Column; detection at 220 nm; flow rate=40 mL/min; continuous gradient from 10% B to 100% B over 10 min+2 min hold at 100% B, where A=10:90:0.1 MeOH—H$_2$O-TFA and B=90:10:0.1 MeOH—H$_2$O-TFA) to afford the acid as a yellow solid. LCMS m/z 296.1 (M+1).

Example 69

A solution of 7-cyano-4-(isopropylamino)-5H-pyrrolo[3, 2-b:4,5-b']dipyridine carboxylic acid, TFA (8 mg, 0.020 mmol), (R)-4-amino-3-fluoro-2-methylbutan-2-ol (2.4 mg, 0.020 mmol), and BOP (8.64 mg, 0.020 mmol), and triethylamine (0.014 mL, 0.1 mmol) in DMF (0.5 mL) was stirred at room temperature for 30 min. The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 10-50% B over 20 minutes, then a 4-minute hold at 100% B; Flow: 20 mL/min. Fractions containing the product were combined and dried via centrifugal evaporation. $^1$H NMR (500 MHz, DMSO-d$_6$) δ 8.84-8.74 (m, 2H), 8.57 (s, 1H), 8.46 (d, J=1.2 Hz, 1H), 8.41 (br d, J=9.2 Hz, 1H), 4.49 (br d, J=4.0 Hz, 1H), 4.46-4.30 (m, 1H), 3.79-3.38 (m, 2H), 1.29-1.22 (m, 6H), 1.17 (br d, J=5.5 Hz, 6H). LCMS m/z 399.2 (M+1).

Example 70

3-(5-isobutyl-1H-1,2,4-triazol-3-yl)-4-(isopropylamino)-5H-pyrido[3,2-b]indole-7-carbonitrile, TFA

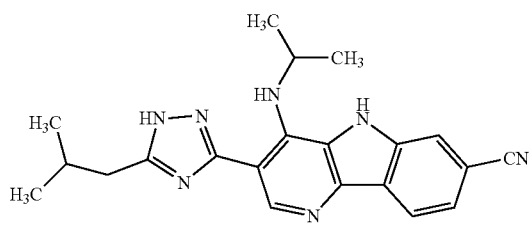

(70)

A solution of 7-cyano-4-(isopropylamino)-5H-pyrido[3,2-b]indole-3-carboxylic acid, HCl (20 mg, 0.06 mmol), ethyl 3-methylbutanimidate hydrochloride (15 mg, 0.091 mmol), BOP (29.4 mg, 0.067 mmol), and N-methylmorpholine (0.033 mL, 0.30 mmol) in DMF (1 mL) was stirred at room temperature overnight. Hydrazine (5.7 µL, 0.18 mmol) was then added and the reaction turned cloudy. The mixture was stirred for 1 h at room temperature and then at 50° C. for 2 h. The mixture was cooled to room temperature and purified using preparative HPLC (Phen Luna Axia C18 5 µm; 30×100 mm Column; detection at 220 nm; flow rate=40 mL/min; continuous gradient from 10% B to 100% B over 10 min+5 min hold at 100% B, where A=10:90:0.1 MeOH—H$_2$O-TFA and B=90:10:0.1 MeOH—H$_2$O-TFA) to afford 3-(5-isobutyl-1H-1,2,4-triazol-3-yl) (isopropylamino)-5H-pyrido[3,2-b]indole-7-carbonitrile, TFA (1.2 mg, 4% yield) as a colorless gum. $^1$H NMR (400 MHz, METHANOL-d$_4$) δ 9.09 (s, 1H), 8.35 (dd, J=8.4, 0.7 Hz, 1H), 8.18 (t, J=1.0 Hz, 1H), 7.68 (dd, J=8.3, 1.3 Hz, 1H), 4.79-4.70 (m, 1H), 2.83-2.76 (m, 2H), 2.21 (dt, J=13.6, 6.8 Hz, 1H), 1.57 (d, J=6.4 Hz, 6H), 1.08-1.02 (m, 6H). LCMS m/z 374.1 (M+1).

TABLE 4

| Ex. No. | Structure | HPLC rt (min) | HPLC cond. | LCMS |
|---|---|---|---|---|
| 71 | 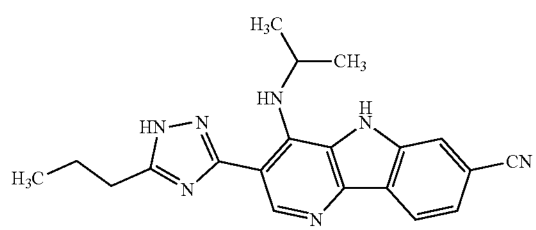 [SMILES: CCCc1nc(-c2cnc3c([nH]c4cc(C#N)ccc43)c2NC(C)C)n[nH]1] | 0.75 | C | 360.1 |

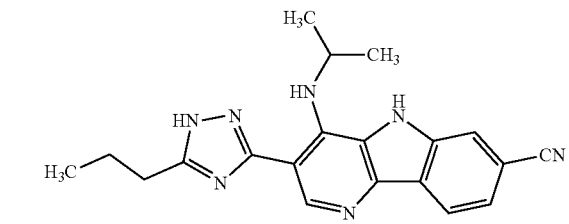

Example 72

4-(isopropylamino)-3-(3-propyl-1,2,4-oxadiazol-5-yl)-5H-pyrido[3,2-b]indole-7-carbonitrile

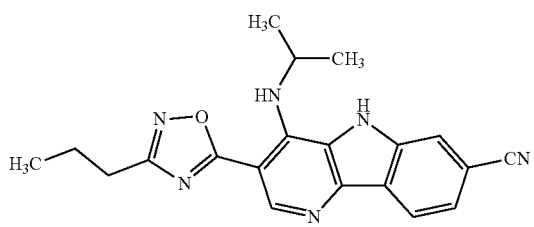

(72)

A solution of 7-cyano-4-(isopropylamino)-5H-pyrido[3,2-b]indole-3-carboxylic acid, TFA (16 mg, 0.04 mmol), N-hydroxybutyrimidamide (4.80 mg, 0.047 mmol), BOP (18.20 mg, 0.041 mmol), and N-methylmorpholine (0.013 mL, 0.118 mmol) in DMF (0.8 mL) was stirred at room temperature for 2.5 h. The mixture was diluted with EtOAc, washed with water (2×) then dried (MgSO$_4$) and concentrated. The crude residue was taken in toluene (0.8 mL) and heated at 100° C. for 1 h. The reaction mixture was concentrated and the crude was purified using preparative HPLC (Phen Luna Axia C18 5 μm; 30×100 mm Column; detection at 220 nm; flow rate=40 mL/min; continuous gradient from 10% B to 100% B over 10 min+5 min hold at 100% B, where A=10:90:0.1 MeOH—H$_2$O-TFA and B=90:10:0.1 MeOH—H$_2$O-TFA) to afford 4-(isopropylamino)-3-(3-propyl-1,2,4-oxadiazol-5-yl)-5H-pyrido[3,2-b]indole carbonitrile, TFA (1.3 mg, 6% yield) as a light yellow solid. $^1$H NMR (400 MHz, METHANOL-d$_4$) δ 9.09 (s, 1H), 8.39 (dd, J=8.4, 0.7 Hz, 1H), 8.22-8.15 (m, 1H), 7.68 (dd, J=8.4, 1.3 Hz, 1H), 4.75 (dt, J=12.6, 6.3 Hz, 1H), 2.95-2.83 (m, 2H), 1.90 (sxt, J=7.4 Hz, 2H), 1.58 (d, J=6.2 Hz, 6H), 1.09 (t, J=7.4 Hz, 3H). LCMS m/z 361.1 (M+1).

Example 73

3-(1-isopentyl-1H-1,2,3-triazol-4-yl)-4-(isopropylamino)-5H-pyrido[3,2-b]indole-7-carbonitrile

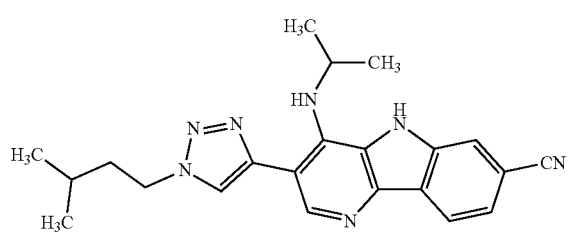

(73)

Intermediate 73A: 7-Bromo-4-(isopropylamino)-5H-pyrido[3,2-b]indole-3-carbaldehyde

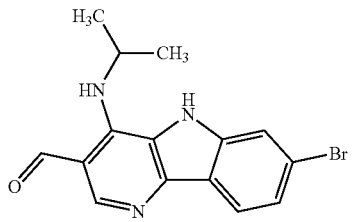

(73A)

A solution of ethyl 7-bromo-4-(isopropylamino)-5H-pyrido[3,2-b]indole-3-carboxylate (0.264 g, 0.70 mmol in DCM (8 mL was cooled to −78° C. and DIBAL-H (1 M in toluene) (1.368 mL, 1.368 mmol was added dropwise. The reaction mixture was stirred at −78° C. for 2 h. An additional aliquot of DIBAL-H (0.702 mL, 0.702 mmol) was added, and the reaction mixture was stirred at −78° C. for 30 min and warmed up to 0° C. for 30 min. The reaction was quenched with MeOH. The reaction mixture was diluted with DCM and saturated NH$_4$Cl and stirred for 15 min. The quenched mixture was extracted with DCM (2×), dried (MgSO$_4$), and concentrated. The residue was dissolved in DCE (10 mL) and manganese dioxide (0.305 g, 3.51 mmol) was added and stirred at 40° C. overnight. The mixture was cooled and filtered through a pad of celite and concentrated. The crude was purified using ISCO flash chromatography (silica gel/hexanes/ethyl acetate 100:0 to 0:100 gradient) to afford 7-bromo-4-(isopropylamino)-5H-pyrido[3,2-b]indole-3-carbaldehyde (125 mg, 54% yield) as a pale yellow solid. LCMS m/z 333.7 (M+2).

Intermediate 73B: 7-Bromo-3-ethynyl-N-isopropyl-5H-pyrido[3,2-b]indol-4-amine

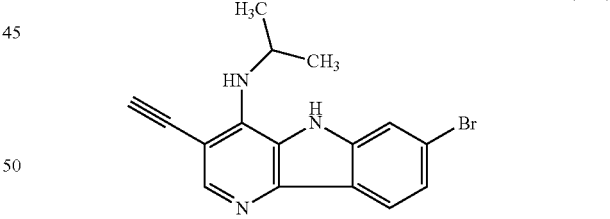

(73B)

Freshly prepared LDA in THF (0.5 mL) was cooled to −78° C. and (trimethylsilyl) diazomethane (2 M in ether) (0.09 mL, 0.181 mmol) was added dropwise over 5 min. The mixture was stirred for 30 min and a solution of 7-bromo-4-(isopropylamino)-5H-pyrido[3,2-b]indole-3-carbaldehyde (50 mg, 0.151 mmol) in THF (1.5 mL) was added slowly. The reaction mixture was allowed to come to room temperature slowly and stirred overnight. Reaction was ~40% complete (monitored by LCMS). The mixture was quenched with water, extracted with EtOAc, dried (MgSO$_4$), and concentrated. The crude was purified using ISCO flash chromatography (silica gel/hexanes/ethyl acetate 100:0 to 0:100 gradient) to afford 7-bromo-3-ethynyl-N-isopropyl-5H-pyrido[3,2-b]indol-4-amine (9 mg, 18% yield) as a light brown solid. $^1$H NMR (400 MHz, METHANOL-$d_4$) δ 8.21 (s, 1H), 8.05 (dd, J=8.4, 0.5 Hz, 1H), 7.72 (dd, 0.5 Hz, 1H), 7.34 (dd, J=8.4, 1.7 Hz, 1H), 4.71 (dt, J=12.7, 6.3 Hz, 1H), 3.95-3.92 (m, 1H), 1.38-1.33 (m, 6H). LCMS m/z 328.0, 330.0 (M+1).

Intermediate 73C: 7-bromo-3-(1-isopentyl-1H-1,2,3-triazol-4-yl)-N-isopropyl-5H-pyrido[3,2-b]indol-4-amine

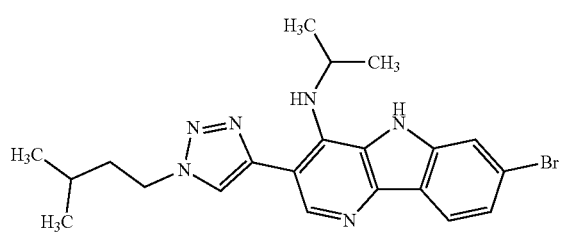

(73C)

A solution of 7-bromo-3-ethynyl-N-isopropyl-5H-pyrido[3,2-b]indol-4-amine (15 mg, 0.046 mmol), 1-azido-3-methylbutane (6.72 mg, 0.06 mmol), sodium ascorbate (3.62 mg, 0.018 mmol), and copper(II) sulfate (1.46 mg, 9.14 µmol) in t-BuOH (0.5 mL) and water (0.5 mL) was heated at 60° C. for 1.5 h. The reaction mixture was cooled, diluted with EtOAc and washed with water. The organic layer was dried (MgSO$_4$) and concentrated to afford the crude 7-bromo-3-(1-isopentyl-1H-1,2,3-triazol-4-yl)-N-isopropyl-5H-pyrido[3,2-b]indol-4-amine (23 mg, 100% yield) as a brown gum. LCMS m/z 443.0 (M+2).

Example 73

A mixture of 7-bromo-3-(1-isopentyl-1H-1,2,3-triazol-4-yl)-N-isopropyl-5H-pyrido[3,2-b]indol-4-amine (21 mg, 0.048 mmol), zinc cyanide (11.17 mg, 0.095 mmol), and Pd(Ph$_3$P)$_4$ (5.5 mg, 4.76 µmol) in DMA (0.8 mL) was stirred at 100° C. overnight. LCMS indicated that reaction was complete. The mixture was cooled and filtered and the filtrate was diluted with EtOAc, washed with saturated NH$_4$C$_1$, water, dried (MgSO$_4$), and concentrated. The crude material was purified via preparative LC/MS with the following conditions: Column: XBridge C18, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 40-80% B over 19 minutes, then a 5-minute hold at 100% B; Flow: 20 mL/min. Fractions containing the product were combined and dried via centrifugal evaporation to afford 3-(1-isopentyl-1H-1,2,3-triazol-4-yl)-4-(isopropylamino)-5H-pyrido[3,2-b]indole-7-carbonitrile (8.6 mg, 44.3% yield). $^1$H NMR (500 MHz, METHANOL-$d_4$) δ 8.57-8.52 (m, 2H), 8.34 (d, J=8.1 Hz, 1H), 7.98 (d, J=0.9 Hz, 1H), 7.52 (dd, J=8.1, 1.4 Hz, 1H), 4.59-4.51 (m, 2H), 4.42 (quin, J=6.3 Hz, 1H), 1.95-1.87 (m, 2H), 1.63 (dt, J=13.4, 6.7 Hz, 1H), 1.37 (d, J=6.3 Hz, 6H), 1.02 (d, J=6.6 Hz, 6H). LCMS m/z 388.2 (M+1).

TABLE 5

| Ex. No. | Structure | HPLC rt (min) | HPLC cond. | LCMS |
|---|---|---|---|---|
| 74 | 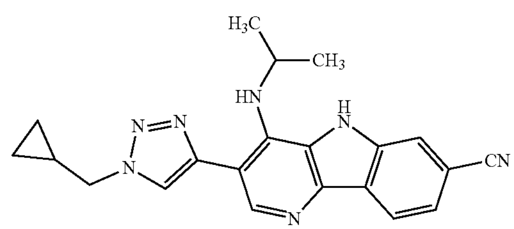 [SMILES: CC(C)Nc1c(-c2cn(CC3CC3)nn2)cnc2c1[nH]c1cc(C#N)ccc12] | 1.81 | A | 372.0 |
| 75 | 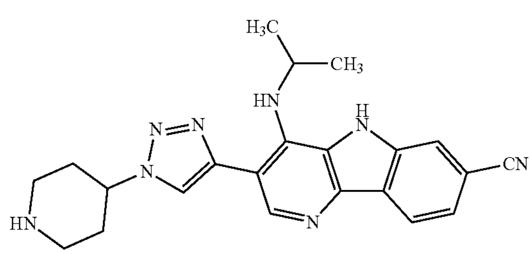 [SMILES: CC(C)Nc1c(-c2cn(C3CCNCC3)nn2)cnc2c1[nH]c1cc(C#N)ccc12] | 1.15 | A | 401.1 |

Example 76

4-(isopropylamino)-3-(3-(piperidin-4-yl)isoxazol-5-yl)-5H-pyrido[3,2-b]indole-7-carbonitrile

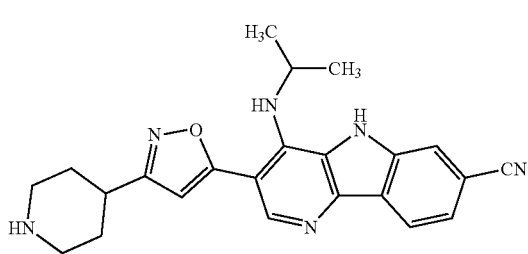

(76)

Intermediate 76A: Tert-butyl 4-(5-(7-bromo-4-(isopropylamino)-5H-pyrido[3,2-b]indol-3-yl)isoxazol-3-yl)piperidine-1-carboxylate, TFA

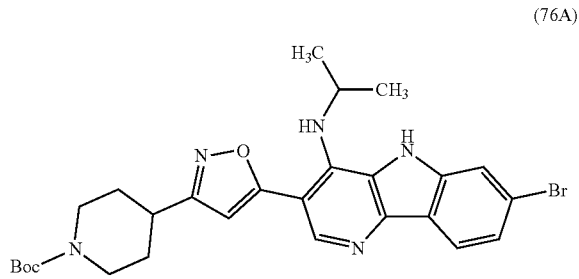 [SMILES: CC(C)Nc1c(-c2cc(C3CCN(C(=O)OC(C)(C)C)CC3)no2)cnc2c1[nH]c1cc(Br)ccc12]

(76A)

A solution of 7-bromo-3-ethynyl-N-isopropyl-5H-pyrido[3,2-b]indol-4-amine (16.5 mg, 0.05 mmol), tert-butyl 4-(chloro(hydroxyimino)methyl)piperidine-1-carboxylate (39.6 mg, 0.151 mmol), and triethylamine (0.028 mL, 0.20 mmol) in DCE (1.2 mL) was heated at 60° C. for 18 h. LCMS showed small amount of regioisomer. The mixture was cooled to room temperature, diluted with DCM, washed with water, dried (MgSO$_4$), and concentrated. The crude was purified using preparative HPLC (Phen Luna Axia C18 5 μm; 21.2×100 mm Column; detection at 220 nm; flow rate=40 mL/min; continuous gradient from 20% B to 100% B over 12 min+2 min hold at 100% B, where A=10:90:0.05 MeOH—H$_2$O-TFA and B=90:10:0.05 MeOH—H$_2$O-TFA) to afford tert-butyl 4-(5-(7-bromo-4-(isopropylamino)-5H-pyrido[3,2-b]indol-3-yl) isoxazol-3-yl)piperidine-1-carboxylate, TFA (8.7 mg, 26% yield) as a brown gum.

Intermediate 76B: Tert-butyl 4-(5-(7-bromo-4-(isopropylamino)-5H-pyrido[3,2-b]indol-3-yl)isoxazol-3-yl)piperidine-1-carboxylate

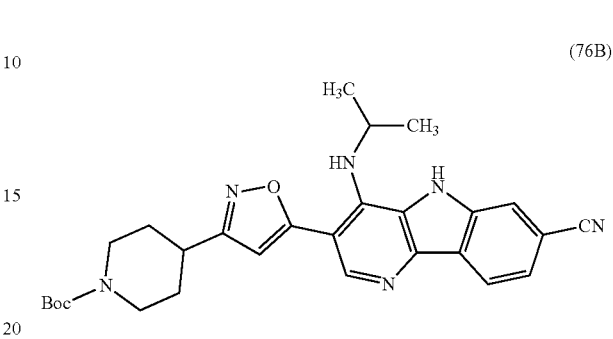

(76B)

A mixture of tert-butyl 4-(5-(7-bromo-4-(isopropylamino)-5H-pyrido[3,2-b]indol-3-yl)isoxazol-3-yl)piperidine-1-carboxylate, TFA (8.7 mg, 0.013 mmol), zinc cyanide (3.06 mg, 0.026 mmol) in DMA (0.5 mL) was purged with nitrogen and stirred at 90° C. for 18 h. Additional zinc cyanide (3.06 mg, 0.026 mmol) and Pd(Ph$_3$P)$_4$ (1.504 mg, 1.301 μmol) was added. The reaction mixture was heated at 120° C. for 24 h. Product was observed by LCMS. The reaction mixture was cooled to room temperature, filtered, diluted with EtOAc, washed with saturated NH$_4$C$_1$, water, dried (MgSO$_4$), and concentrated to afford the crude tert-butyl 4-(5-(7-cyano-4-(isopropylamino)-5H-pyrido[3,2-b]indol-3-yl)isoxazol-3-yl)piperidine-1-carboxylate.

Example 71

A solution of tert-butyl 4-(5-(7-cyano-4-(isopropylamino)-5H-pyrido[3,2-b] indol-3-yl)isoxazol-3-yl)piperidine-1-carboxylate was stirred in TFA (0.5 mL, 6.49 mmol) and DCM (0.5 mL) for 15 min and concentrated. The crude was purified using preparative HPLC (Phen Luna Axia C18 5 μm; 21.2×100 mm Column; detection at 220 nm; flow rate=40 mL/min; continuous gradient from 10% B to 100% B over 10 min+2 min hold at 100% B, where A=10:90:0.1 MeOH—H$_2$O-TFA and B=90:10:0.1 MeOH—H$_2$O-TFA) to afford 4-(isopropylamino)-3-(3-(piperidin-4-yl)isoxazol-5-yl)-5H-pyrido[3,2-b]indole-7-carbonitrile, 2 TFA (3 mg, 36% yield). $^1$H NMR (400 MHz, METHANOL-d$_4$) δ 8.53 (s, 1H), 8.37 (dd, J=8.4, 0.6 Hz, 1H), 8.19 (s, 1H), 7.69 (dd, J=8.4, 1.3 Hz, 1H), 6.92 (s, 1H), 4.15 (d, J=6.1 Hz, 1H), 3.53 (dt, J=13.0, 3.6 Hz, 2H), 3.29-3.17 (m, 3H), 2.36 (dd, J=14.7, 3.2 Hz, 2H), 2.14-1.98 (m, 2H), 1.41 (d, J=6.4 Hz, 6H). LCMS m/z 401.1

TABLE 6

| Ex. No. | Structure | HPLC rt (min) | HPLC cond. | LCMS |
|---|---|---|---|---|
| 77 | (structure shown) | 1.72 | A | 402.0 |

TABLE 6-continued

| Ex. No. | Structure | HPLC rt (min) | HPLC cond. | LCMS |
|---|---|---|---|---|
| 78 | 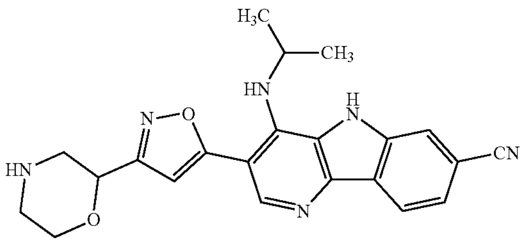 [SMILES: CC(C)Nc1c(-c2cc(C3CNCCO3)no2)cnc2c1[nH]c1cc(C#N)ccc12] | 1.31 | A | 403.1 |
| 79 | 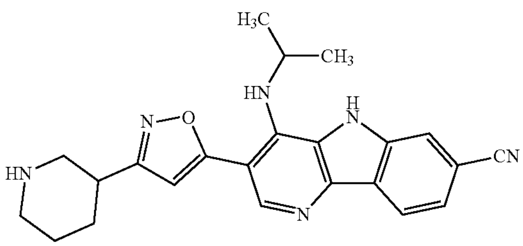 [SMILES: CC(C)Nc1c(-c2cc(C3CCCNC3)no2)cnc2c1[nH]c1cc(C#N)ccc12] | 0.86 | B | 401.2 |
| 80 | 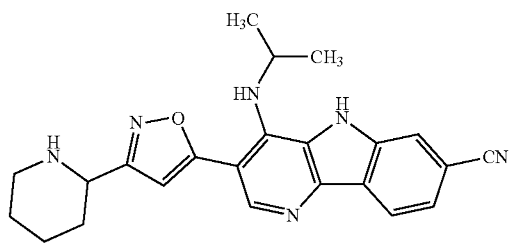 [SMILES: CC(C)Nc1c(-c2cc(C3CCCCN3)no2)cnc2c1[nH]c1cc(C#N)ccc12] | 0.61 | C | 401.2 |

Example 81

(R)-6-cyano-N-(2-fluoro-3-hydroxy-3-methylbutyl)-4-(isopropylamino)-9H-pyrido [2,3-b]indole-3-carboxamide

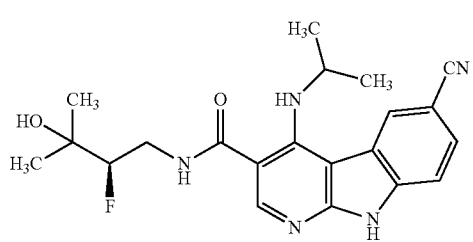
(81)

Intermediate 81A: Methyl 5-(5-cyano-2-nitrophenyl)nicotinate

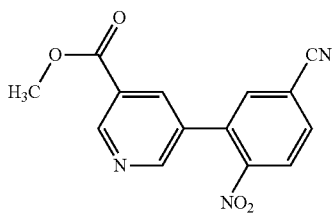
(81A)

A mixture of 3-bromo-4-nitrobenzonitrile (0.59 g, 2.6 mmol), methyl 5-(4,4,5,5-tetramethyl-1,3,2-dioxaborolan-2-yl)nicotinate (0.684 g, 2.6 mmol), potassium phosphate tribasic (1.66 g, 7.8 mmol), and bis(triphenylphosphine)palladium(II) chloride (0.091 g, 0.13 mmol) in THF (15 mL) and water (3 mL) was stirred at 90° C. for 5 h. The reaction mixture was diluted with EtOAc, washed with saturated sodium bicarbonate, dried (MgSO$_4$), and concentrated. The crude product was subjected to ISCO flash chromatography (silica gel/hexane-EtOAc 100:0 to 0:100 gradient) to afford methyl 5-(5-cyano-2-nitrophenyl)nicotinate (370 mg, 50% yield). LCMS m/z 284.0 (M+1).

Intermediates 81B and 81C: Methyl 8-cyano-5H-pyrido[4,3-b]indole-4-carboxylate and methyl 6-cyano-9H-pyrido[2,3-b]indole-3-carboxylate

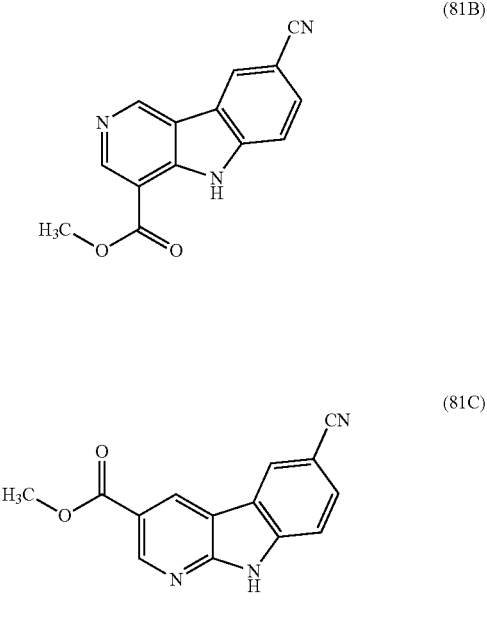

A mixture of methyl 5-(5-cyano-2-nitrophenyl)nicotinate (370 mg, 1.31 mmol), DPPF (651 mg, 1.63 mmol in 1,2-dichlorobenzene (1.5 mL, 13.1 mmol was flushed with nitrogen and stirred at 150° C. for 1 h. The reaction mixture was cooled and concentrated and the residue was recrystallized from DMF to afford methyl 6-cyano-9H-pyrido[2,3-b]indole-3-carboxylate (130 mg, 40% yield) as the major product. $^1$H NMR (400 MHz, DMSO-$d_6$) δ 12.80 (br s, 1H), 9.22 (d, J=2.0 Hz, 1H), 9.07 (d, J=2.1 Hz, 1H), 8.93 (s, 1H), 7.89 (br d, J=8.4 Hz, 1H), 7.69 (d, J=8.4 Hz, 1H), 3.93 (s, 3H). LCMS m/z 250.0 (M+1).

Intermediate 81D: 6-Cyano-3-(methoxycarbonyl)-9H-pyrido[2,3-b]indole 1-oxide

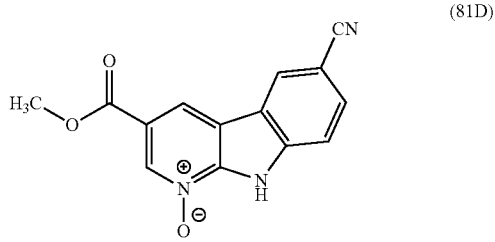 [SMILES: COC(=O)c1cc2c3cc(C#N)ccc3[nH]c2[n+]([O-])c1]

Hydrogen peroxide (30%, 453 µL, 5.17 mmol) was added in 3 portions over 2 h to a stirred suspension of methyl 6-cyano-9H-pyrido[2,3-b]indole-3-carboxylate (130 mg, 0.517 mmol) in acetic acid (3 mL) in a sealed vial with septum at 90° C. The mixture was concentrated and the residue was sonicated with half saturated NaHCO$_3$ solution. A white solid was isolated by filtration; washed with water, dried to afford the crude 6-cyano-3-(methoxycarbonyl)-9H-pyrido[2,3-b]indole 1-oxide (130 mg, 94% yield). $^1$H NMR (400 MHz, DMSO-$d_6$) δ 9.01 (d, J=1.0 Hz, 1H), 8.90 (d, J=1.2 Hz, 1H), 8.80 (d, J=1.2 Hz, 1H), 7.96 (dd, J=8.4, 1.6 Hz, 1H), 7.74 (d, J=8.4 Hz, 1H), 3.95 (s, 3H). LCMS m/z 267.8 (M+1).

Intermediates 81E and 81F: Methyl 4-chloro-6-cyano-9H-pyrido[2,3-b]indole-3-carboxylate and Methyl 2-chloro-6-cyano-9H-pyrido[2,3-b]indole-3-carboxylate

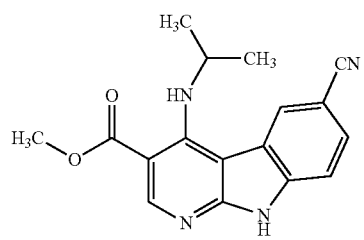

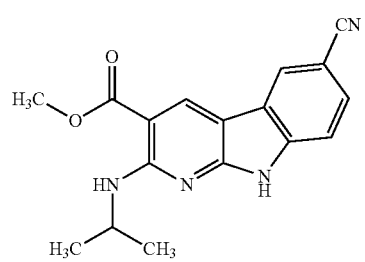

POCl$_3$ (91 µL, 0.97 mmol) was added to a stirred suspension of 6-cyano-3-(methoxycarbonyl)-9H-pyrido[2,3-b]indole 1-oxide (130 mg, 0.49 mmol) in DMF (4 mL) at 4° C. and allowed to warm to room temperature and stirred for 4 h. The mixture was concentrated and the residue was suspended in half saturated NaHCO$_3$, sonicated and filtered. The solid was washed with water and dried to afford 130 mg of 1.6:1 mixture methyl 4-chloro-6-cyano-9H-pyrido[2,3-b]indole-3-carboxylate and methyl 2-chloro-6-cyano-9H-pyrido[2,3-b]indole-3-carboxylate.

A mixture of the chlorides and propan-2-amine (26.9 mg, 0.455 mmol) in acetonitrile (2 mL) was stirred at 90° C. for 5 h and concentrated. The crude product was subjected to preparative HPLC (ODS column/water-CH$_3$OH-TFA 90:10:0.05 to 10:90:0.05 gradient) to afford in the order of elution: methyl 6-cyano-4-(isopropylamino)-9H-pyrido[2,3-b]indole-3-carboxylate, TFA (22 mg, 11% yield). $^1$H NMR (400 MHz, DMSO-$d_6$) δ 12.66 (s, 1H), 8.85 (s, 1H), 8.12 (s, 1H), 8.04 (d, J=10.4 Hz, 1H), 7.80 (dd, J=8.4, 1.2 Hz, 1H), 7.64 (d, J=8.3 Hz, 1H), 4.29-4.12 (m, 1H), 3.88 (s, 3H). LCMS m/z 308.9 (M+1) and methyl 2-chloro-6-cyano-9H-pyrido[2,3-b]indole-3-carboxylate, TFA, (52 mg, 27% yield); $^1$H NMR at 100° C. (400 MHz, DMSO-$d_6$) δ 11.69 (br. s., 1H), 8.87 (s, 1H), 8.34 (d, J=1.2 Hz, 1H), 7.59 (dd, J=8.3, 1.6 Hz, 1H), 7.47 (d, J=8.3 Hz, 1H), 4.40 (spt, J=6.5 Hz, 1H), 3.90 (s, 3H), 1.31 (d, J=6.5 Hz, 6H); LCMS m/z 308.9 (M+1).

Intermediate 81G: 6-cyano-4-(isopropylamino)-9H-pyrido[2,3-b]indole-3-carboxylic acid

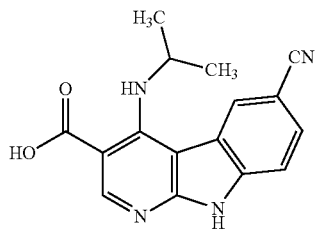

(81G)

A mixture of methyl 6-cyano-4-(isopropylamino)-9H-pyrido[2,3-b]indole-3-carboxylate (16 mg, 0.052 mmol) and 0.5 N lithium hydroxide (156 µL, 0.078 mmol) in dioxane (0.75 mL) was heated at 90° C. in a sealed vial for 5 h. The mixture was diluted with water (1 mL), washed with ether and the aqueous layer was concentrated. The residue was taken in 1N HCl (0.45 mL), sonicated and concentrated. The crude product was triturated with water to afford 6-cyano-4-(isopropylamino)-9H-pyrido[2,3-b]indole-3-carboxylic acid, HCl (14 mg, 82% yield). LCMS m/z 295.1 (M+1).

Example 81

A mixture of (R)-4-amino-3-fluoro-2-methylbutan-2-ol, 6-cyano-4-(isopropylamino)-9H-pyrido[2,3-b]indole-3-carboxylic acid, HCl (7 mg, 0.021 mmol), BOP (11.23 mg, 0.025 mmol) and TEA (8.85 µL, 0.063 mmol) in DMF (0.3 mL) was stirred at room temperature for 5 h. The reaction mixture was diluted with methanol and concentrated. The crude product was subjected to preparative HPLC (ODS column/water-MeOH-TFA 90:10:0.1 to 10:90:0.1 gradient) to afford (R)-6-cyano-N-(2-fluoro-3-hydroxy-3-methylbutyl)-4-(isopropylamino)-9H-pyrido[2,3-b]indole carboxamide, TFA (7.4 mg, 65% yield). $^1$H NMR (400 MHz, METHANOL-$d_4$) δ 8.47 (s, 1H), 8.37 (s, 1H), 7.83 (dd, J=8.4, 1.5 Hz, 1H), 7.75 (dd, J=8.4, 0.5 Hz, 1H), 4.55-4.32 (m, 2H), 3.91 (ddd, J=36.4, 14.3, 2.0 Hz, 1H), 3.55 (ddd, J=15.6, 14.6, 9.5 Hz, 1H), 1.44 (d, J=2.7 Hz, 3H), 1.42 (d, J=2.7 Hz, 3H), 1.30 (s, 3H), 1.30 (s, 3H). LCMS m/z 398.2 (M+1).

| Ex. No. | Structure | HPLC rt (min) | HPLC cond. | LCMS |
|---|---|---|---|---|
| 82 | 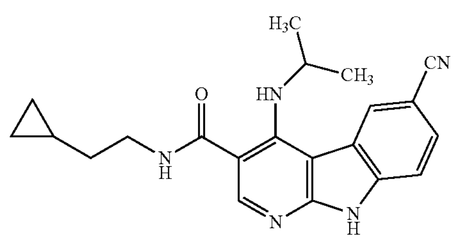 [SMILES: CC(C)Nc1c(C(=O)NCCC2CC2)cnc2[nH]c3ccc(C#N)cc3c12] | 0.92 | A | 362.2 |

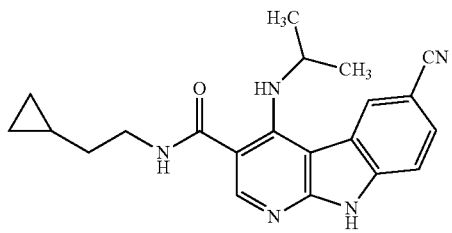

HPLC Conditions:

Method A: Waters Acquity UPLC BEH C18, 2.1×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm.

Method B: Waters Acquity UPLC BEH C18, 2.1×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm.

Method C: Waters Acquity UPLC BEH C18 2.1×50 mm, 1.7 µm; Mobile Phase A: 2:98 acetonitrile:water with 0.0.05% trifluoroacetic acid; Mobile Phase B: 98:2 acetonitrile:water with 0.05% trifluoroacetic acid; Temperature: 50° C.; Gradient: 0-100% B over 1 minutes, then a 0.50-minute hold at 100% B; Flow: 1.0 mL/min; Detection: UV at 220 nm.

Biological Assays

The pharmacological properties of the compounds of this invention may be confirmed by a number of biological assays. The exemplified biological assays, which follow, have been carried out with compounds of the invention.

IRAK4 Inhibition Assay

The assays were performed in U-bottom 384-well plates. The final assay volume was 30 µL prepared from 15 µL additions of enzyme and substrates (fluoresceinated peptide and ATP) and test compounds in assay buffer (20 mM HEPES pH 7.2, 10 mM $MgCl_2$, 0.015% Brij 35 and 4 mM DTT). The reaction was initiated by the combination of IRAK4 with substrates and test compounds. The reaction mixture was incubated at room temperature for 60 min. and terminated by adding 45 µL of 35 mM EDTA to each sample. The reaction mixture was analyzed on the Caliper LABCHIP® 3000 (Caliper, Hopkinton, MA) by electrophoretic separation of the fluorescent substrate and phosphorylated product. Inhibition data were calculated by comparison to no enzyme control reactions for 100% inhibition and vehicle-only reactions for 0% inhibition. The final concentrations of reagents in the assays are ATP, 500 µM; FL-IPTSPITTTYFFFKKK peptide 1.5 µM; IRAK4, 0.6 nM; and DMSO, 1.6%.

IRAK4 Whole Blood Assay

Human whole blood containing the anti-coagulant ACD-A was plated in 384-well plate (25 µL/well) and incubated with compounds for 60 minutes at 37° C. in a 5% $CO_2$ incubator. The blood was stimulated with a TLR2 agonist, 10 µg/mL final concentration of lipoteichoic acid (Invivogen, San Diego, CA) in 25 µL RPMI (Gibco) for 5 hours in a 5% $CO_2$ incubator. At the end of the incubation, plates were centrifuged at 2300 rpm for 5 minutes. Supernatants were harvested and analyzed for IL-6 levels by Flow Cytometry beads assay (BD Biosciences, San Jose, CA).

TABLE 7

IRAK4 Inhibition Data

| Example No. | IRAK4 $IC_{50}$ (µM) | Whole Blood $EC_{50}$ (µM) |
|---|---|---|
| 1 | 0.0020 | 0.43 |
| 2 | 0.0016 | 1.30 |
| 3 | 0.019 | 2.47 |
| 4 | 0.0020 | 1.99 |
| 5 | 0.0038 | 1.44 |
| 6 | 0.037 | — |
| 7 | 0.17 | — |
| 8 | 0.33 | — |
| 9 | 0.33 | — |
| 10 | 0.012 | 2.89 |
| 11 | 0.027 | — |
| 12 | 0.0086 | 2.72 |
| 13 | 0.0037 | 2.21 |
| 14 | 0.019 | 3.50 |
| 15 | 0.016 | 1.45 |
| 16 | 0.31 | — |
| 17 | 0.013 | 4.73 |
| 18 | 0.017 | 8.17 |
| 19 | 0.020 | — |
| 20 | 0.014 | 1.05 |
| 21 | 0.0021 | 1.34 |
| 22 | 0.0021 | 0.23 |
| 23 | 0.015 | >10 |
| 24 | 0.12 | |
| 25 | 0.0035 | 1.50 |
| 26 | 0.033 | — |
| 27 | 0.013 | >10 |
| 28 | 0.048 | — |
| 29 | 0.011 | — |
| 30 | 0.0053 | 3.38 |
| 31 | 0.0095 | >20 |
| 32 | 0.015 | >20 |
| 33 | 0.0308 | — |
| 34 | 0.0034 | 0.58 |
| 35 | 0.0030 | 0.77 |
| 36 | 0.0091 | 3.32 |
| 37 | 0.014 | — |
| 38 | 0.0031 | 0.51 |
| 39 | 0.0039 | >20 |
| 40 | 0.0063 | 1.60 |
| 41 | 0.0092 | — |
| 42 | 0.024 | — |
| 43 | 0.0025 | 0.74 |
| 44 | 0.0031 | 0.51 |
| 45 | 0.033 | — |
| 46 | 0.0026 | 0.74 |
| 47 | 0.040 | — |
| 48 | 0.24 | — |
| 49 | 0.022 | — |
| 50 | 0.033 | — |
| 51 | 0.016 | 1.55 |
| 52 | 0.0033 | — |
| 53 | 0.0019 | — |
| 54 | 0.014 | >10 |
| 55 | 0.0028 | — |
| 56 | 0.51 | — |
| 57 | 0.018 | 0.61 |
| 58 | 0.024 | — |
| 59 | 0.0054 | >10 |
| 60 | 0.0038 | >20 |
| 61 | 0.0072 | >20 |
| 62 | 0.0033 | 12.3 |
| 63 | 0.0071 | >20 |
| 64 | 0.053 | — |
| 65 | 0.10 | — |
| 66 | 0.0086 | 1.24 |
| 67 | 0.030 | — |
| 68 | 0.58 | — |
| 69 | 0.54 | — |
| 70 | 1.7 | — |
| 71 | 0.50 | — |
| 72 | 0.36 | — |
| 73 | 0.0015 | — |
| 74 | 0.0092 | >10 |
| 75 | 0.0015 | 0.93 |

TABLE 7-continued

IRAK4 Inhibition Data

| Example No. | IRAK4 IC$_{50}$ (μM) | Whole Blood EC$_{50}$ (μM) |
|---|---|---|
| 76 | 0.0023 | 0.82 |
| 77 | 0.011 | 0.99 |
| 78 | 0.026 | — |
| 79 | 0.022 | — |
| 80 | 0.018 | 3.31 |
| 81 | 0.17 | — |
| 82 | 0.65 | — |

What is claimed is:

1. A compound of Formula (I) or Formula (II):

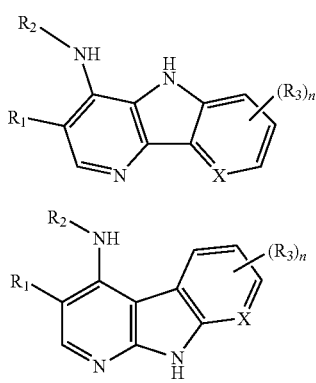

or a salt thereof, wherein:

X is $CR_{3a}$ or N;

$R_1$ is:
(i) —C(O)NR$_x$R$_{1a}$; or
(ii) pyrazolyl, imidazolyl, isoxazolyl, oxazolyl, oxadiazolyl, triazolyl, or thiadiazolyl, each substituted with zero to 2 R$_{1b}$;

$R_{1a}$ is:
(i) C$_{1-6}$ alkyl substituted with zero to 6 R$_w$; or
(ii) —(CR$_x$R$_x$)$_{0-3}$R$_{1c}$;

each R$_w$ is independently F, Cl, —CN, —OH, —OCH$_3$, —NR$_x$R$_x$, —NR$_x$C(O)(C$_{1-3}$ alkyl), —NR$_x$C(O)(C$_{3-6}$ cycloalkyl), or C$_{3-6}$ cycloalkyl;

each R$_{1b}$ is independently —CR$_x$R$_x$(C$_{3-6}$ cycloalkyl), tetrahydrofuranyl, pyrrolidinyl, tetrahydropyranyl, piperidinyl, piperazinyl, morpholinyl, or C$_{1-6}$ alkyl substituted with zero to 6 R$_w$;

$R_{1c}$ is C$_{3-6}$ cycloalkyl, oxetanyl, pyrrolidinyl, piperidinyl, piperazinyl, morpholinyl, tetrahydropyranyl, dioxidotetrahydrothiophenyl, dioxidothiomorpholinyl, isoxazolyl, oxazolyl, thiazolyl, oxadiazolyl, triazolyl, or tetrazolyl, each substituted with zero to 3 substituents independently selected from F, Cl, —CN, —OH, —NR$_x$R$_x$, C$_{1-3}$ alkyl, C$_{1-3}$ fluoroalkyl, C$_{1-3}$ hydroxyalkyl, —NR$_x$C(O)(C$_{1-3}$ alkyl), —NR$_x$C(O)O(C$_{1-3}$ alkyl), and —S(O)$_2$(C$_{1-2}$ alkyl);

$R_2$ is:
(i) hydrogen;
(ii) C$_{1-6}$ alkyl substituted with zero to 4 substituents independently selected from F, Cl, —OH, —CN, C$_{3-6}$ cycloalkyl, and dimethoxyphenyl; or
(ii) a cyclic group selected from C$_{3-6}$ cycloalkyl, oxetanyl, tetrahydrofuranyl, tetrahydropyranyl, piperidinyl, pyrazolyl, and thiazolyl, wherein said cyclic group is substituted with zero to 3 substituents independently selected from F, Cl, —OH, —CN, C$_{1-2}$ alkyl, C$_{1-2}$ fluoroalkyl, C$_{1-2}$ hydroxyalkyl, and —S(O)$_2$(C$_{1-2}$ alkyl);

$R_3$ is —CN, —C(O)NR$_x$R$_x$, or a cyclic group selected from phenyl, pyrazolyl, imidazolyl, triazolyl, pyridinyl, pyridinonyl, and pyrimidinyl, each cyclic group substituted with zero to 3 substituents selected from F, Cl, —OH, —CN, C$_{1-2}$ alkyl, —CF$_3$, and —CH$_2$OH;

$R_{3a}$ is hydrogen or R$_3$;

each R$_x$ is hydrogen or —CH$_3$; and n is zero, 1, or 2.

2. The compound according to claim 1 having the structure of Formula (I) or a salt thereof.

3. The compound according to claim 1 having the structure of Formula (II) or a salt thereof.

4. The compound according to claim 1 having the structure of Formula (Ia) or Formula (IIa):

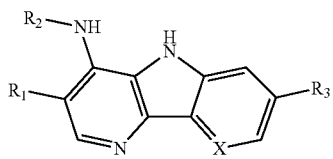
(Ia)

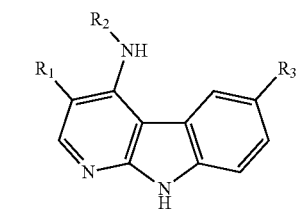
(IIa)

or a salt thereof, wherein:
X is CH or N;
R₁ is:
  (i) —C(O)NHR₁ₐ; or
  (ii) isoxazolyl, oxadiazolyl, or triazolyl, each substituted with R₁ᵦ;
R₁ₐ is —CH₂CH₂CH₃, —CH₂CH(CH₃)₂, —CH₂CH₂CH(CH₃)₂, —CH₂CH₂CHF₂, —CH₂CH₂CF₃, —CH₂CH₂C(CH₃)₂F, —CH₂CH₂CH(CH₃)OH, —CH₂C(CH₃)₂CH₂OH, —CH₂CH₂C(CH₃)₂OH, —CH₂CHFCH(CH₃)OH, —CH₂CHFC(CH₃)₂OH, —CH₂CH₂OCH₃, —CH₂CH₂C(CH₃)₂NH₂, —CH₂CF₂CH₂NH₂, —CH₂CH₂C(CH₃)₂NHC(O)CH₃, —CH(cyclopropyl)CH₂CH₂OH, —CH₂CH₂C(CH₃)₂NHC(O)(cyclopropyl), R₁c, —CH₂R₁c, or —CH₂CH₂R₁c;
R₁ᵦ is —CH₂CH₂CH₃, —CH₂CH(CH₃)₂, —CH₂CH₂CH(CH₃)₂, —CH₂(cyclopropyl), tetrahydropyranyl, piperidinyl, or morpholinyl;
R₁c is cyclopropyl, cyclobutyl, oxetanyl, pyrrolidinyl, piperidinyl, morpholinyl, tetrahydropyranyl, dioxidotetrahydrothiophenyl, dioxidothiomorpholinyl, isoxazolyl, oxazolyl, thiazolyl, triazolyl, or tetrazolyl, each substituted with zero to 3 substituents independently selected from F, —OH, —NH₂, —CH₃, —CH₂OH, —C(CH₃)₂OH, —NHC(O)CH₃, —NHC(O)OCH₃, and —S(O)₂CH₃;
R₂ is hydrogen, —CH₂CH₃—CH(CH₃)₂, —CH(CH₃)CH₂CH₃, —CH₂CHF₂, —CH₂CF₃, —CH(CH₃)CH₂OH, —CH₂(cyclopropyl), —CH(CH₃)(cyclopropyl), —CH₂(dimethoxyphenyl), cyclopropyl, cyclobutyl, difluorocyclobutyl, oxetanyl, tetrahydrofuranyl, (methylsulfonyl)piperidinyl, thiazolyl, or (difluoroethyl)pyrazolyl;
and R₃ is —CN, —C(O)NH₂, pyrazolyl, or pyridinonyl.

5. The compound according to claim 1 or a salt thereof, wherein X is CH.

6. The compound according to claim 1 or a salt thereof, wherein R₁ is —C(O)NR$_x$R₁ₐ.

7. The compound according to claim 1 or a salt thereof, wherein R₁ is pyrazolyl, imidazolyl, isoxazolyl, oxazolyl, oxadiazolyl, triazolyl, or thiadiazolyl, each substituted with R₁ᵦ.

8. A compound or a salt thereof, wherein said compound is:
(R)-7-cyano-N-(2-fluoro-3-hydroxy-3-methylbutyl)-4-(isopropylamino)-5H-pyrido[3,2-b]indole-3-carboxamide (1);
(R)-7-cyano-4-(ethylamino)-N-(2-fluoro-3-hydroxy-3-methylbutyl)-5H-pyrido[3,2-b]indole-3-carboxamide (2);
(R)-7-cyano-4-((3,3-difluorocyclobutyl)amino)-N-(2-fluoro-3-hydroxy-3-methylbutyl)-5H-pyrido[3,2-b]indole-3-carboxamide (3);
(R)-7-cyano-4-(cyclobutylamino)-N-(2-fluoro-3-hydroxy-3-methylbutyl)-5H-pyrido[3,2-b]indole-3-carboxamide (4);
7-cyano-N-(3-hydroxy-3-methylbutyl)-4-(isopropylamino)-5H-pyrido[3,2-b]indole-3-carboxamide (5);
7-cyano-4-(isopropylamino)-N-(tetrahydro-2H-pyran-3-yl)-5H-pyrido[3,2-b]indole-3-carboxamide (6);
7-cyano-N-((3-(hydroxymethyl)oxetan-3-yl)methyl)-4-(isopropylamino)-5H-pyrido[3,2-b]indole-3-carboxamide (7);
7-cyano-N-((1-(hydroxymethyl)cyclopropyl)methyl)-4-(isopropylamino)-5H-pyrido[3,2-b]indole-3-carboxamide (8);
7-cyano-N-(3-hydroxy-2,2-dimethylpropyl)-4-(isopropylamino)-5H-pyrido[3,2-b]indole-3-carboxamide (9);
7-cyano-N-((1R,4R)-4-hydroxycyclohexyl)-4-(isopropylamino)-5H-pyrido[3,2-b]indole-3-carboxamide (10);
7-cyano-4-(isopropylamino)-N-(tetrahydro-2H-pyran-4-yl)-5H-pyrido[3,2-b]indole-3-carboxamide (11);
N-((1R,4R)-4-aminocyclohexyl)-7-cyano-4-(isopropylamino)-5H-pyrido[3,2-b]indole-3-carboxamide (12);
N-((1R,4R)-4-acetamidocyclohexyl)-7-cyano-4-(isopropylamino)-5H-pyrido[3,2-b]indole-3-carboxamide (13);
7-cyano-4-(isopropylamino)-N-(oxazol-4-ylmethyl)-5H-pyrido[3,2-b]indole-3-carboxamide (14);
7-cyano-4-(isopropylamino)-N-((3-methylisoxazol-5-yl)methyl)-5H-pyrido[3,2-b]indole-3-carboxamide (15);
7-cyano-N-(1-cyclopropyl-3-hydroxypropyl)-4-(isopropylamino)-5H-pyrido[3,2-b]indole-3-carboxamide (16);
7-cyano-4-(isopropylamino)-N-(2-methoxyethyl)-5H-pyrido[3,2-b]indole-3-carboxamide (17);
7-cyano-4-(isopropylamino)-N-(thiazol-2-ylmethyl)-5H-pyrido[3,2-b]indole-3-carboxamide (18);
7-cyano-4-(isopropylamino)-N-(piperidin-4-yl)-5H-pyrido[3,2-b]indole-3-carboxamide (19);
N-((1H-1,2,4-triazol-5-yl)methyl)-7-cyano-4-(isopropylamino)-5H-pyrido[3,2-b]indole-3-carboxamide (20);
7-cyano-N-isopentyl-4-(isopropylamino)-5H-pyrido[3,2-b]indole-3-carboxamide (21);
(R)-7-cyano-N-(2-fluoro-3-hydroxy-3-methylbutyl)-4-(oxetan-3-ylamino)-5H-pyrido[3,2-b]indole-3-carboxamide (22);
(R)-7-cyano-4-((1-(2,2-difluoroethyl)-1H-pyrazol-4-yl)amino)-N-(2-fluoro-3-hydroxy-3-methylbutyl)-5H-pyrido[3,2-b]indole-3-carboxamide (23);
7-cyano-N-((1s,3s)-3-hydroxycyclobutyl)-4-(isopropylamino)-5H-pyrido[3,2-b]indole-3-carboxamide (24);
7-cyano-N-(3-hydroxybutyl)-4-(isopropylamino)-5H-pyrido[3,2-b]indole-3-carboxamide (25);
(R)-7-cyano-N-(3-hydroxy-3-methylbutyl)-4-((tetrahydrofuran-3-yl)amino)-5H-pyrido[3,2-b]indole-3-carboxamide (26);
7-cyano-4-(isopropylamino)-N-(3,3,3-trifluoropropyl)-5H-pyrido[3,2-b]indole-3-carboxamide (27);

(S)-7-cyano-N-(3-hydroxy-3-methylbutyl)-4-((tetrahydrofuran-3-yl)amino)-5H-pyrido[3,2-b]indole-3-carboxamide (28);
(S)-7-cyano-4-((1-cyclopropylethyl)amino)-N-(3-hydroxy-3-methylbutyl)-5H-pyrido[3,2-b]indole-3-carboxamide (29);
(S)-7-cyano-N-(3-hydroxy-3-methylbutyl)-4-((1-hydroxypropan-2-yl)amino)-5H-pyrido[3,2-b]indole-3-carboxamide (30);
7-cyano-N-(3,3-difluoropropyl)-4-(isopropylamino)-5H-pyrido[3,2-b]indole-3-carboxamide (31);
(R)-4-(sec-butylamino)-7-cyano-N-(3-hydroxy-3-methylbutyl)-5H-pyrido[3,2-b]indole-3-carboxamide (32);
7-cyano-4-((cyclopropylmethyl)amino)-N-(3-hydroxy-3-methylbutyl)-5H-pyrido[3,2-b]indole-3-carboxamide (33);
7-cyano-N-(2-cyclopropylethyl)-4-(isopropylamino)-5H-pyrido[3,2-b]indole-3-carboxamide (34);
7-cyano-4-(isopropylamino)-N-(2-morpholinoethyl)-5H-pyrido[3,2-b]indole-3-carboxamide (35);
7-cyano-4-((2,2-difluoroethyl)amino)-N-(3-hydroxy-3-methylbutyl)-5H-pyrido[3,2-b]indole-3-carboxamide (36);
7-cyano-N-(3-hydroxy-3-methylbutyl)-4-((2,2,2-trifluoroethyl)amino)-5H-pyrido[3,2-b]indole-3-carboxamide (37);
7-cyano-N-(3-fluoro-3-methylbutyl)-4-(isopropylamino)-5H-pyrido[3,2-b]indole-3-carboxamide (38);
7-cyano-N-((1R,3R)-3-(2-hydroxypropan-2-yl)cyclobutyl)-4-(isopropylamino)-5H-pyrido[3,2-b]indole-3-carboxamide (39);
4-(tert-butylamino)-7-cyano-N-(3-hydroxy-3-methylbutyl)-5H-pyrido[3,2-b]indole-3-carboxamide (40);
7-cyano-N-(3-hydroxy-3-methylbutyl)-4-(oxetan-3-ylamino)-5H-pyrido[3,2-b]indole-3-carboxamide (41);
7-cyano-4-(oxetan-3-ylamino)-N-(3,3,3-trifluoropropyl)-5H-pyrido[3,2-b]indole-3-carboxamide (42);
7-cyano-N-(2-(3,3-difluoro-1-hydroxycyclobutyl)ethyl)-4-(isopropylamino)-5H-pyrido[3,2-b]indole-3-carboxamide (43);
7-cyano-4-(cyclopropylamino)-N-((1R,3R)-3-(2-hydroxypropan-2-yl)cyclobutyl)-5H-pyrido[3,2-b]indole-3-carboxamide (44);
7-cyano-4-(cyclopropylamino)-N-((1R,3R)-3-hydroxycyclobutyl)-5H-pyrido[3,2-b]indole-3-carboxamide (45);
7-cyano-4-(cyclopropylamino)-N-(3-hydroxy-3-methylbutyl)-5H-pyrido[3,2-b]indole-3-carboxamide (46);
N-((1R,3R)-3-aminocyclobutyl)-7-cyano-4-(isopropylamino)-5H-pyrido[3,2-b]indole-3-carboxamide (47);
N3-(3-hydroxy-3-methylbutyl)-4-(isopropylamino)-5H-pyrido[3,2-b]indole-3,7-dicarboxamide (48);
N-((1R,3R)-3-acetamidocyclobutyl)-7-cyano-4-(isopropylamino)-5H-pyrido[3,2-b]indole-3-carboxamide (49);
methyl ((1R,3R)-3-(7-cyano-4-(isopropylamino)-5H-pyrido[3,2-b]indole-3-carboxamido)cyclobutyl)carbamate (50);
N-(3-amino-2,2-difluoropropyl)-7-cyano-4-(isopropylamino)-5H-pyrido[3,2-b]indole-3-carboxamide (51);
N-(3-amino-3-methylbutyl)-7-cyano-4-(isopropylamino)-5H-pyrido[3,2-b]indole-3-carboxamide (52);
7-cyano-4-(isopropylamino)-N-(2-(pyrrolidin-3-yl)ethyl)-5H-pyrido[3,2-b]indole-3-carboxamide (53);
4-amino-7-cyano-N-(3-hydroxy-3-methylbutyl)-5H-pyrido[3,2-b]indole-3-carboxamide (54);
7-cyano-4-(ethylamino)-N-(2-(piperidin-3-yl)ethyl)-5H-pyrido[3,2-b]indole-3-carboxamide (55);
7-cyano-4-((3,4-dimethoxybenzyl)amino)-N-(3-hydroxy-3-methylbutyl)-5H-pyrido[3,2-b]indole-3-carboxamide (56);
7-cyano-4-(ethylamino)-N-(2-(pyrrolidin-2-yl)ethyl)-5H-pyrido[3,2-b]indole-3-carboxamide (57);
7-cyano-4-(ethylamino)-N-(2-(piperidin-2-yl)ethyl)-5H-pyrido[3,2-b]indole-3-carboxamide (58);
7-cyano-N-(3-(cyclopropanecarboxamido)-3-methylbutyl)-4-(isopropylamino)-5H-pyrido[3,2-b]indole-3-carboxamide (59);
N-(3-acetamido-3-methylbutyl)-7-cyano-4-(isopropylamino)-5H-pyrido[3,2-b]indole-3-carboxamide (60);
7-cyano-N-((1,1-dioxidotetrahydrothiophen-3-yl)methyl)-4-(isopropylamino)-5H-pyrido[3,2-b]indole-3-carboxamide (61);
7-cyano-N-(2-(1,1-dioxidothiomorpholino)ethyl)-4-(isopropylamino)-5H-pyrido[3,2-b]indole-3-carboxamide (62);
7-cyano-4-(isopropylamino)-N-(1-(methylsulfonyl)piperidin-4-yl)-5H-pyrido[3,2-b]indole-3-carboxamide (63);
(R)-7-cyano-N-(2-fluoro-3-hydroxy-3-methylbutyl)-4-((1-(methylsulfonyl)piperidin-4-yl) amino)-5H-pyrido[3,2-b]indole-3-carboxamide (64);
N-(2-(1H-tetrazol-5-yl)ethyl)-7-cyano-4-(isopropylamino)-5H-pyrido[3,2-b]indole-3-carboxamide (65);
(R)—N-(2-fluoro-3-hydroxy-3-methylbutyl)-4-(isopropylamino)-7-(thiazol-5-yl)-5H-pyrido[3,2-b]indole-3-carboxamide (66);
(R)—N-(2-fluoro-3-hydroxy-3-methylbutyl)-4-(isopropylamino)-7-(1H-pyrazol-4-yl)-5H-pyrido[3,2-b]indole-3-carboxamide (67);
(R)—N-(2-fluoro-3-hydroxy-3-methylbutyl)-4-(isopropylamino)-7-(6-oxo-1,6-dihydropyridin-3-yl)-5H-pyrido[3,2-b]indole-3-carboxamide (68);
(R)-7-cyano-N-(2-fluoro-3-hydroxy-3-methylbutyl)-4-(isopropylamino)-5H-pyrrolo[3,2-b:4,5-b']dipyridine-3-carboxamide (69);
3-(5-isobutyl-1H-1,2,4-triazol-3-yl)-4-(isopropylamino)-5H-pyrido[3,2-b]indole-7-carbonitrile, TFA (70);
4-(isopropylamino)-3-(5-propyl-1H-1,2,4-triazol-3-yl)-5H-pyrido[3,2-b]indole-7-carbonitrile (71);
4-(isopropylamino)-3-(3-propyl-1,2,4-oxadiazol-5-yl)-5H-pyrido[3,2-b]indole-7-carbonitrile (72);
3-(1-isopentyl-1H-1,2,3-triazol-4-yl)-4-(isopropylamino)-5H-pyrido[3,2-b]indole-7-carbonitrile (73);
3-(1-(cyclopropylmethyl)-1H-1,2,3-triazol-4-yl)-4-(isopropylamino)-5H-pyrido[3,2-b]indole-7-carbonitrile (74);
4-(isopropylamino)-3-(1-(piperidin-4-yl)-1H-1,2,3-triazol-4-yl)-5H-pyrido[3,2-b]indole-7-carbonitrile (75);
4-(isopropylamino)-3-(3-(piperidin-4-yl)isoxazol-5-yl)-5H-pyrido[3,2-b]indole-7-carbonitrile (76);
4-(isopropylamino)-3-(3-(tetrahydro-2H-pyran-4-yl)isoxazol-5-yl)-5H-pyrido[3,2-b]indole-7-carbonitrile (77);
4-(isopropylamino)-3-(3-(morpholin-2-yl)isoxazol-5-yl)-5H-pyrido[3,2-b]indole-7-carbonitrile (78);
4-(isopropylamino)-3-(3-(piperidin-3-yl)isoxazol-5-yl)-5H-pyrido[3,2-b]indole-7-carbonitrile (79);
4-(isopropylamino)-3-(3-(piperidin-2-yl)isoxazol-5-yl)-5H-pyrido[3,2-b]indole-7-carbonitrile (80);

(R)-6-cyano-N-(2-fluoro-3-hydroxy-3-methylbutyl)-4-(isopropylamino)-9H-pyrido[2,3-b]indole-3-carboxamide (81); or 6-cyano-N-(2-cyclopropylethyl)-4-(isopropylamino)-9H-pyrido[2,3-b]indole-3-carboxamide (82).

9. A pharmaceutical composition comprising one or more compounds according to claim 1 and a pharmaceutically acceptable carrier or diluent.

\* \* \* \* \*